(12) United States Patent
Godel et al.

(10) Patent No.: US 6,770,637 B2
(45) Date of Patent: Aug. 3, 2004

(54) SUBSTITUTED 4-PHENYL-PYRIDINE COMPOUNDS WITH ACTIVITY AS ANTAGONISTS OF NEUROKININ 1 RECEPTORS

(75) Inventors: Thierry Godel, Basel (CH); Torsten Hoffmann, Weil am Rhein (DE); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 118 days.

(21) Appl. No.: 09/922,066

(22) Filed: Aug. 3, 2001

(65) Prior Publication Data

US 2002/0040040 A1 Apr. 4, 2002

(30) Foreign Application Priority Data

Aug. 8, 2000 (EP) ............................................. 00117003

(51) Int. Cl.[7] ...................... A61K 31/33; A61K 31/435; C07D 265/30; C07D 403/00; C07D 241/04
(52) U.S. Cl. ............... 514/183; 514/252.13; 514/231.5; 514/235.5; 544/106; 544/111; 544/359; 544/360; 544/372; 544/383; 544/384; 544/386
(58) Field of Search ............................ 514/183, 252.13, 514/231.5, 235, 235.5; 544/106, 111, 359, 360, 372, 383, 384, 386

(56) References Cited

U.S. PATENT DOCUMENTS

| | | | | |
|---|---|---|---|---|
| 4,745,123 A | * | 5/1988 | Butler et al. ................. | 514/356 |
| 5,972,938 A | | 10/1999 | Rupniak et al. ......... | 514/236.2 |
| 6,297,375 B1 | * | 10/2001 | Boes et al. .................... | 544/60 |
| 6,303,790 B1 | * | 10/2001 | Hilpert et al. ............... | 546/308 |

FOREIGN PATENT DOCUMENTS

| | | | |
|---|---|---|---|
| DE | 10008042 | * | 8/2001 |
| EP | 103 545 | | 3/1984 |
| EP | 035 115 | | 9/2000 |
| WO | 95/16679 | | 6/1995 |
| WO | 95/18124 | | 7/1995 |
| WO | 95/23798 | | 9/1995 |
| WO | WO 97/19926 | | 6/1997 |
| WO | 9821185 | * | 5/1998 |
| WO | WO 00/50398 | | 8/2000 |

OTHER PUBLICATIONS

Barker, *Reviews in the Neurosciences*, vol. 7,, No. 3, pp. 187–214 (1996).
Longmore et al., *Can. J. Physiol. Pharmacol.*, vol. 75, pp. 612–621 (1997).
Kramer et al., *Science*, vol. 281, pp. 1640–1645.
Maggi et al., *J. Auton. Pharmacol*, vol. 13, pp. 23–93 (1993).
Navari et al., *The New England Journal of Medicine*, vol. 340, No. 3, pp. 190–195 (1999).
Maggi et al., Neuropeptides, vol. 32(1), pp. 1–49 (1998).
Doi et al., Eur. J. Pharmacol., vol. 383(3), pp. 297–303 (1999).
Ikeura et al., *Chem. Pharm. Bull.*, vol. 45(10), pp. 1642–162 (1997).

* cited by examiner

*Primary Examiner*—Mukund J. Shah
*Assistant Examiner*—Sudhaker B. Patel
(74) *Attorney, Agent, or Firm*—George W. Johnston; Patricia S. Rocha-Tramaloni; Kimberly J. Prior

(57) ABSTRACT

Substituted 4-phenyl-pyridine compounds with activity as antagonists of Neurokinin 1 receptors, methods of making these compounds and preparing.

19 Claims, No Drawings

SUBSTITUTED 4-PHENYL-PYRIDINE COMPOUNDS WITH ACTIVITY AS ANTAGONISTS OF NEUROKININ 1 RECEPTORS

FIELD OF INVENTION

The present invention is generally related to substituted 4-phenyl-pyridine compounds showing activity as Neurokinin 1 Receptors (NK-1, substance P) antagonists and more particularly to the compounds, methods for their synthesis and methods of treatment of disease using these compounds.

BACKGROUND

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors. The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting. In addition, in The New England Journal of Medicine, Vol. 340, No. 3 190–195, 1999 has been described the reduction of cisplatin-induced emesis by a selective neurokinin-1-receptor antagonist. Furthermore, U.S. Pat. No. 5,972,938 describes a method for treating a psychoimmunologic or a psychosomatic disorder by administration of a tachykinin receptor, such as NK-1 receptor antagonist. The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

SUMMARY

The present invention relates to compounds of the formula

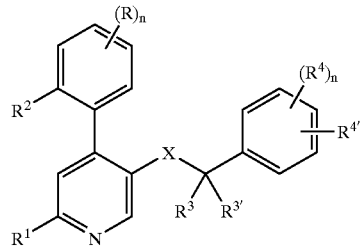

wherein
R is hydrogen or halogen;
$R^1$ is —(C≡C)$_m$R$^{1'}$ or —(CR'=CR")$_m$R$^{1'}$
wherein $R^{1'}$ is
a) hydrogen or halogen,
b) cyano, or the following groups:

c)

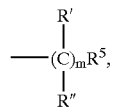

d) —C(O)NR'R",
e) —C(O)O(CH$_2$)$_m$R$^5$,
f) —C(O)R$^5$,
g) —N(OH)—(CH$_2$)$_m$R$^5$,
h) —NR'C(O)—(CH$_2$)$_m$R$^5$,
i) —N[C(O)—R']$_2$,
j) —OR$^6$,
k) —(CH$_2$)$_m$—SR$^6$, —(CH$_2$)$_m$—S(O)R$^6$, or —(CH$_2$)$_m$—S(O)$_2$R$^6$,
l) aryl, unsubstituted or substituted by at least one substituent, selected from halogen, trifluoromethyl, lower alkyl, lower alkoxy, cyano, hydroxy, —NR'R", nitro, —(CH$_2$)$_n$OR', —C(O)NR'R", —C(O)OR' or —C(O)R',
m) is a five or six membered unsubstsituted heteroaryl group, containing one to four heteroatoms, selected from N, O or S or substituted by at least one substituents, selected from halogen, trifluoromethyl, lower alkyl, lower alkoxy, cyano, hydroxy, —NR'R", nitro, —(CH$_2$)$_n$OR', —C(O)OR', —C(O)NR'R" or —C(O)R',
n) is a five or six membered saturated or unsaturated heterocycles

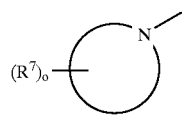

that contain one nitrogen atom or one nitrogen atom and one additional heteroatom, selected from N, O or S,
R'/R" are independently from each other hydrogen, hydroxy, lower alkyl, cycloalkyl or aryl, wherein the lower alkyl, cycloalkyl or aryl group may be optionally substituted by one or more substituents, selected from halogen, trifluoromethyl, lower alkyl, lower alkoxy, cyano, hydroxy, —NR'''R"", nitro, —(CH$_2$)$_n$OR''', —C(O)NR'''R"", —C(O)OR''' or —C(O)R''',
R'''/R"" are independently from each other hydrogen, lower alkyl, cycloalkyl or aryl, $R^5$ is hydrogen, cyano, hydroxy, halogen, trifluoromethyl, —C(O)OR', —OC(O)R' or aryl, unsubstituted or substituted by at least one substituent, selected from halogen, trifluoromethyl, lower alkyl, lower alkoxy, cyano, hydroxy, —NR'R", nitro, —(CH$_2$)$_n$OR', —C(O)NR'R", —C(O)OR' or —C(O)R', or is a five or six membered unsubstituted heteroaryl group, containing one to four heteroatoms, selected from N, or S or a substituted heteroaryl group, containing one to four heteroatoms selected from N, O or S substituted by at least one substituent, selected from halogen, trifluoromethyl, lower alkyl, lower alkoxy, cyano, hydroxy, —NR'R", nitro, —(CH$_2$)$_n$OR', —C(O)NR'R", —C(O)OR' or —C(O)R', $R^6$ is hydrogen, lower alkyl, trifluoromethyl, or aryl, or substituted lower alkyl or aryl group by at least one substituent, selected from halogen, trifluoromethyl, lower alkyl, lower alkoxy, cyano, hydroxy, —NR'R", nitro, —C(O)NR'R", —(CH$_2$)$_n$, OR', —C(O)OR' or —C(O)R', or is a five or six membered aromatic heterocyclic group, containing one to four heteroatoms, selected from N, O or S and unsubstituted or substituted by at least one substituents, selected from halogen, trifluoromethyl, lower alkyl, lower alkoxy, cyano, hydroxy, —NR'R", nitro, —(CH$_2$)$_n$OR', —C(O)NR'R", —C(O)OR' or —C(O)R', $R^7$ is —C(O)—(CH$_2$)$_m$OH or an oxo group;

$R^2$ is hydrogen, lower alkyl, lower alkoxy, halogen or CF$_3$;

$R^3/R^{3'}$ are independently from each other hydrogen, lower alkyl or form together with the carbon atom to which they are attached a cycloalkyl group;

$R^4/R^{4'}$ are independently from each other hydrogen, halogen, CF$_3$, lower alkyl or lower alkoxy;

R and $R^2$ or $R^4$ and $R^{4'}$ may be together —CH=CH—CH=CH—, optionally substituted by one or two substituents selected from lower alkyl, halogen or lower alkoxy;

X is —C(O)N(R$^8$)—, (CH$_2$)$_p$O—, —(CH$_2$)$_p$N(R$^8$)—, —N(R$^8$)C(O)— or —N(R$^8$)—(CH$_2$)$_p$—;

wherein $R^8$ is hydrogen or lower alkyl;

n is 1 or 2;

m is 0, 1, 2, 3 or 4;

o is 1 or 2; and p is 1 or 2;

or a pharmaceutically acceptable acid addition salt thereof.

The compounds of formula I and their salts are characterized by valuable therapeutic properties. It has been surprisingly found that the compounds of the present invention are antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The compounds of formula I can also be used in form of their prodrugs. Examples are esters, N-oxides, phosphate esters, glycoamide esters, glyceride conjugates and the like. The prodrugs may add to the value of the present compounds advantages in adsorption, pharmacokinetics in distribution and transport to the brain.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

DETAILED DESCRIPTION

As used herein, the term "lower alkyl" denotes a saturated straight- or branched-chain alkyl group containing from 1 to 7 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group, containing 3–6 carbon atoms, a preferred cycloalkyl is cyclopropyl.

The term "halogen" denotes chlorine, iodine, fluorine and bromine.

The term "lower alkoxy" denotes a group wherein the alkyl residue is as defined above, and which is attached via an oxygen atom.

The term "five or six membered aromatic heterocycle, containing one to four heteroatoms, selected from N, O or S" denotes, for example, the following groups: pyrrol-1-yl, imidazol-1 or 2-yl, pyrazol-1-yl, pyridin-2, 3 or 4-yl, pyrazinyl, pyrimidinyl, pyridazinyl, isothiazolyl, isoxazolyl, thienyl, 1,2,3-triazolyl, 1,2,4-oxadiazolyl, tetrahydro-pyridinyl, isoxazolyl or furyl and the like.

The term "five or six membered non-aromatic heterocycle having at least one nitrogen atom or one nitrogen atom and a second hetero atom selected from the group nitrogen, sulfur and oxygen." denotes, for example, pyrrolidinyl, imidazolidinyl, pyrazolidinyl, piperidinyl, piperazinyl, morpholinyl, thiomorpholinyl, thiomorpholin-1,1-dioxo or thiomorpholin-1-oxo and the like.

The term "aryl" denotes a monocyclic aromatic hydrocarbon radical or a bicyclic or tricyclic ring system in which at least one ring is aromatic, preferred are phenyl, benzyl or naphthyl rings.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

A preferred compound of formula 1 has the formula

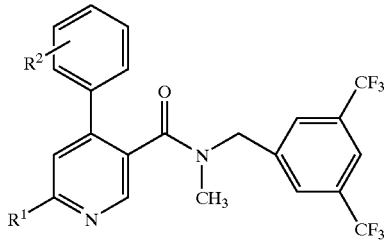

1-100 with R$_1$ and R$^2$ as defined above. R$^2$ is preferred as lower alkyl with 2-methyl being particularly preferred. Also preferred are compounds of formula 1–100 including R$^1$ being an unsubstituted or substituted five or six membered non-aromatic heterocycle of the formula

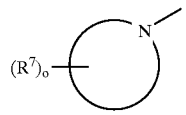

containing at least one nitrogen or one nitrogen and one additional hetero atom selected from N, O or S with R$^7$ and o as defined above. Additional preferred compounds of formula 1–100 when R$^2$ is 2-methyl, include compounds with R$^1$ being a substituted aryl group, an unsubstituted heteroaryl group, a substituted hetero aryl group, cyano,

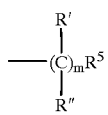

—(CH$_2$)$_m$—S(O)R$^6$ with m and R$^6$ as defined above, —OR$^6$ with R$^6$ as defined above, with R', R", m and R$^5$ as defined above, —(CH$_2$)$_m$—SR$^6$ with m and R$^6$ as defined above or —(CH$_2$)$_m$—S(O)$_2$R$^6$ with R$^6$ and m as defined above. Yet another preferred compound of the formula 1–100 includes R$^1$ and R$^2$ being halogen. Another preferred compound of formula 1 has the formula 1-101

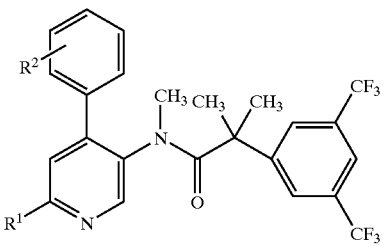

with R$^1$ being halogen, particularly chlorine. Another preferred compound of formula 1–101 includes R$^2$ being halogen or more particularly with R$^2$ being 2-chloro. Further preferred compounds of formula 1–101 include R$^2$ being lower alkyl, particularly 2-methyl. Additional preferred compounds of formula 1–101 when R$^2$ is 2-methyl include R$^1$ being —NR'C(O)—(CH$_2$)$_m$R$^5$ with R', m and R$^5$ defined as above, a five or six membered non-aromatic heterocycle of the formula

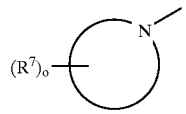

containing at least one nitrogen or one nitrogen and one additional hetero atom selected from N, O or S with R$^7$ and o as defined above. Further preferred compounds of formula 1–101 wherein R$^2$ is 2-methyl include R$^1$ being —N[C(O)—R']$_2$ where R' is as above, —N(OH)—(CH$_2$)$_m$R$^5$ where m and R$^5$ are as above, —(C≡C)$_m$R$^{1'}$ where m and R$^{1'}$ are as above, —C(O)O(CH$_2$)$_m$R$^5$ where m and R$^5$ are as above, —OR$^6$, where R$^6$ is as above or —(CH$_2$)$_m$—S(O)R$^6$, where m and R$^6$ are as above. An additional preferred compound where R$^2$ is 2-methyl include R$^1$ being a five or six membered aromatic heterocycle, containing one to four heteroatoms, selected from N, O or S and, unsubstituted or substituted by one or more substituents, selected from halogen, trifluoromethyl, lower alkyl, lower alkoxy, cyano, hydroxy, —NR'R", nitro, —(CH$_2$)$_n$OR', —C(O)OR', —C(O)NR'R" or —C(O)R', and wherein n, R' and R" are as above.

Preferred are compounds of formula I, in which X is —C(O)N(CH$_3$)— and —(R$^4$)$_n$ is 3,5-di-CF$_3$. Exemplary preferred compounds of this group are those, wherein R$^3$/R$^{3'}$ are both hydrogen and R$^2$ is methyl, for example the following compounds:

N-(3,5-bis-trifluoromethyl-benzyl)-6-(4-hydroxyacetyl-piperazin-1-yl)-N-methyl-4-o-tolyl-nicotinamide, N-(3,5-bis-trifluoromethyl-benzyl)-6-chloro-N-methyl-4-o-tolyl-nicotinamide, N-(3,5-bis-trifluoromethyl-benzyl)-6-cyanomethyl-N-methyl-4-o-tolyl-nicotinamide, N-(3,5-bis-trifluoromethyl-benzyl)-6-iodo-N-methyl-4-o-tolyl-nicotinamide, 4-o-tolyl-[2,4']bipyridinyl-5-carboxylic acid (3,5-bis-trifluoromethyl-benzyl)-methyl-amide, 5-[(3,5-bis-trifluoromethyl-benzyl)-methyl-carbamoyl]-4-o-tolyl-pyridine-2-carboxylic acid methyl ester, N-(3,5-bis-trifluoromethyl-benzyl)-6-hydroxymethyl-N-methyl-4-o-tolyl-nicotinamide, 6-(5-acetyl-thiophen-2-yl)-N-(3,5-bis-trifluoromethyl-benzyl)-N-methyl-4-o-tolyl-nicotinamide, 4-o-tolyl-1',2',3',6'-tetrahydro-[2,4'] bipyridinyl-5-carboxylic acid (3,5-bis-trifluoromethylbenzyl)-methyl-amide, N-(3,5-bis-trifluoromethyl-benzyl)-6-(4-hydroxymethyl-phenyl)-N-methyl-4-o-tolyl-nicotinamide, 2'-methyl-4-o-tolyl-[2,4'] bipyridinyl-5-carboxylic acid (3,5-bis-trifluoromethyl-benzyl)-methyl-amide, N-(3,5-bis-trifluoromethyl-benzyl)-N-methyl-6-(3-methyl-[1,2,4] oxadiazol-5-yl)-4-o-tolyl-nicotinamide, 6-(3-amino-prop-1-ynyl)-N-(3,5-bis-trifluoromethyl-benzyl)-N-methyl-4-o-tolyl-nicotinamide, (RS)-N-(3,5-bis-trifluoromethyl-benzyl)-6-(2-hydroxy-ethanesulfinylmethyl)-N-methyl-4-o-tolyl-nicotinamide, N-(3,5-bis-trifluoromethyl-b enzyl)-N-methyl-6-(1-methyl-1H-imidazol-2-ylsulfanylmethyl)-4-o-tolyl-nicotinamide, (RS)-N-(3,5-bis-trifluoromethyl-benzyl)-N-methyl-6-(pyridine-2-sulfinyl)-4-o-tolyl-nicotinamide, N-(3,5-bis-trifluoromethyl-benzyl)-N-methyl-6-(pyridine-2-sulfonyl)-4-o-tolyl-nicotinamide or N-(3,5-bis-trifluoromethyl-benzyl)-6-(3-hydroxy-propoxy)-N-methyl-4-o-tolyl-nicotinamide.

Further preferred are compounds of formula I, in which X is —N(CH$_3$)C(O)— and —(R$^4$)$_n$ is 3,5-di-CF$_3$. Exemparly preferred compounds of this group are those, wherein R$^3$/R$^{3'}$ are both methyl and R$^2$ is methyl, for example the following compounds:

2-(3,5-bis-trifluoromethyl-phenyl)-N-{6-[hydroxy-(2-hydroxy-ethyl)-amino]-4-o-tolyl-pyridin-3-yl}-N-methyl-isobutyramide, 2-(3,5-bis-trifluoromethyl-phenyl)-N-methyl-N-[6-(3-oxo-morpholin-4-yl)-4-o-tolyl-pyridin-3-yl]-isobutyramide, acetic acid (5-{[2-(3,5-bis-trifluoromethyl-phenyl)-2-methyl-propionyl]-methyl-amino}-4-o-tolyl-pyridin-2-ylcarbamoyl)-methyl ester, 2-(3,5-bis-trifluoromethyl-phenyl)-N-[6-(2-hydroxy-acetylamino)-4-o-tolyl-pyridin-3-yl]-N-methyl-isobutyramide,
2-(3,5-bis-trifluoromethyl-phenyl)-N-[6-(hydroxyacetyl-methyl-amino)-4-o-tolyl-pyridin-3-yl]-N-methyl-isobutyramide,
2-(3,5-bis-trifluoromethyl-phenyl)-N-[6-(2,5-dioxo-pyrrolidin-1-yl)-4-o-tolyl-pyridin-3-yl]-N-methyl-isobutyramide, cyclopropanecarboxylic acid (5-{[2-(3,5-bis-trifluoromethyl-phenyl)-2-methyl-propionyl]-methyl-amino}-4-o-tolyl-pyridin-2-yl)-cyclopropanecarbonyl-amide,
2-(3,5-bis-trifluoromethyl-phenyl)-N-(6-chloro-4-o-tolyl-pyridin-3-yl)-N-methyl-isobutyramide,
2-(3,5-bis-trifluoromethyl-phenyl)-N-[4-(2-chloro-phenyl)-2'-methyl-[2,4']bipyridinyl-5-yl]-N-methyl-isobutyramide,
2-(3,5-bis-trifluoromethyl-phenyl)-N-(6-ethynyl-4-o-tolyl-pyridin-3-yl)-N-methyl-isobutyramide,
2-(3,5-bis-trifluoromethyl-phenyl)-N-[6-(3-hydroxymethyl-isoxazol-5-yl)-4-o-tolyl-pyridin-3-yl]-N-methyl-isobutyramide,
2-(3,5-bis-trifluoromethyl-phenyl)-N-[6-(3-hydroxy-prop-1-ynyl)-4-o-tolyl-pyridin-3-yl]-N-methyl-isobutyramide or
(RS)-2-(3,5-bis-trifluoromethyl-phenyl)-N-[6-(3-methoxy-benzenesulfinyl)-4-o-tolyl-pyridin-3-yl]-N-methyl-isobutyramide.

Preferred compounds of this group are further those, wherein $R^3/R^{3'}$ are both methyl and $R^2$ is chloro, for example the following compounds:
2-(3,5-bis-trifluoromethyl-phenyl)-N-{4-(2-chloro-phenyl)-6-[hydroxy-(2-hydroxy-ethyl)-amino]-pyridin-3-yl}-N-methyl-isobutramide or
2-(3,5-bis-trifluoromethyl-phenyl)-N-[4-(2-chloro-phenyl)-6-(3-oxo-morpholin-4-yl)-pyridin-3-oxo-morpholin-4-yl)-pyridin-3-yl]-N-methyl-isobytyramide.

The present compounds of formula I and their pharmaceutically acceptable salts can be prepared by methods known in the art, for example, by processes described below, which process comprises
reacting a compound of formula

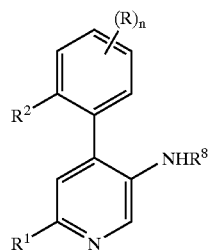

II with a compound of formula

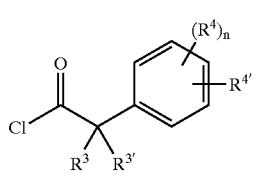

III to a compound of formula

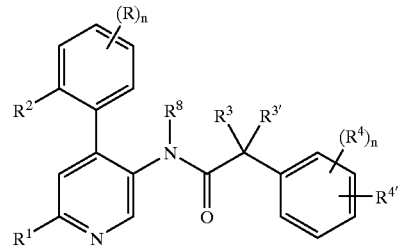

Ia wherein $R^1$–$R^4$, R and n have the significances given above,
or reacting a compound of formula

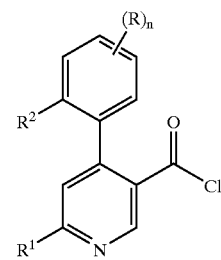

IV with a compound of formula

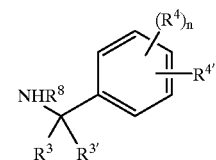

V to give a compound of formula

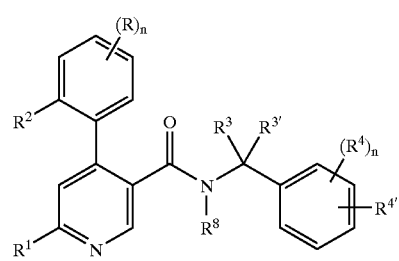

Ib wherein $R^1$–$R^4$, R and n have the significances given above,
or reducing a compound of formula

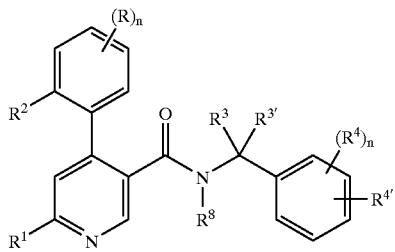

Ib to a compound of formula

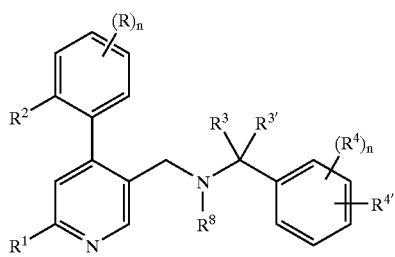

Ic wherein the definition of substituents is given above, or reacting a compound of formula

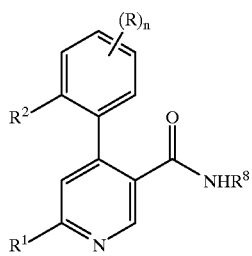

VI with a compound of formula

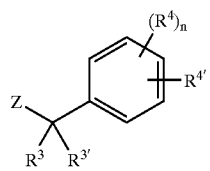

VII to a compound of formula

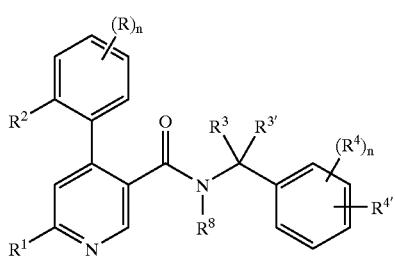

Ib wherein Z is Cl, Br, I, —OS(O)$_2$CH$_3$ or —OS(O)$_2$C$_6$H$_4$CH$_3$ and the other definitions of substituents are given above, or reacting a compound of formula

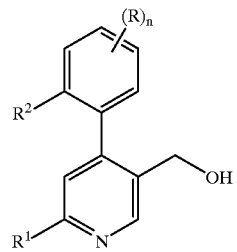

VIII with a compound of formula

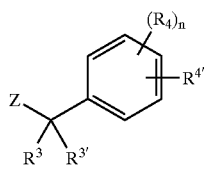

VII to a compound of formula

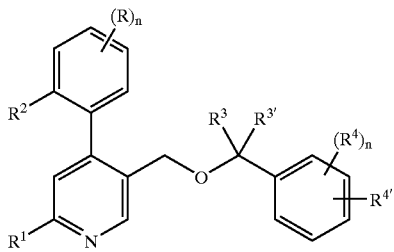

Id wherein Z is Cl, Br, I, —OS(O)$_2$CH$_3$ or —OS(O)$_2$C$_6$H$_4$CH$_3$ and the definition of the other substituents is given above, or reducing a compound of formula

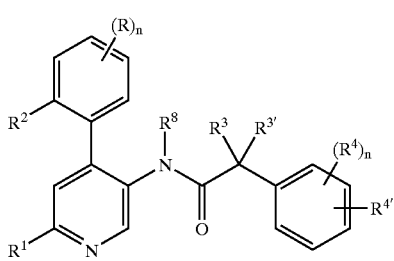

Ia to a compound of formula

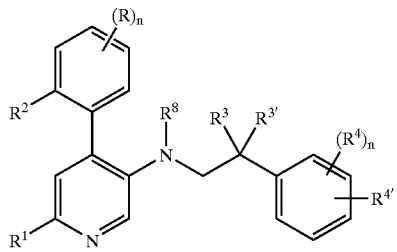

Ie wherein the definition of substituents is given above, or
if desired, converting the compound obtained into a pharmaceutically acceptable acid addition salt.

Furthermore, the substituent $R^1$ may be modified within the definitions given above, for example to the following compounds of formulas I-2, I-4, I-5, I-7, I-8, I-10, I-11, I-12, I-13 or I-14 by:

reacting a compound of formula

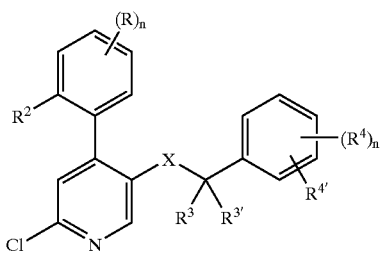

I-1 with a compound of formula $R^1H$
to a compound of formula

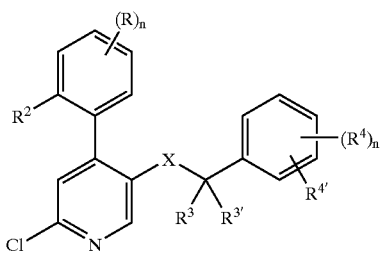

I-2 wherein the substituents are described above, or
reacting a compound of formula

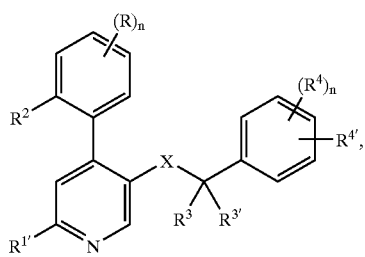

I-3 with a compound of formula $R^6$-Z to give a compound of formula

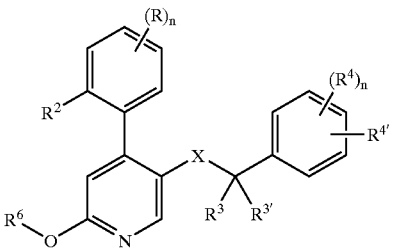

I-4

Z = Cl, Br, I or OS(O)$_2$C$_6$H$_4$CH$_3$ or OS(O)$_2$CH$_3$ and wherein the remaining substituents are described above, or reacting a compound of formula

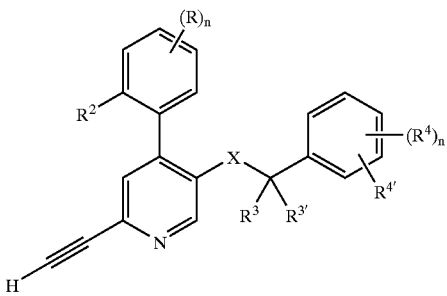

I-6 with $R^{1'}$-Br or $R^{1'}$-I to give a compound of formula

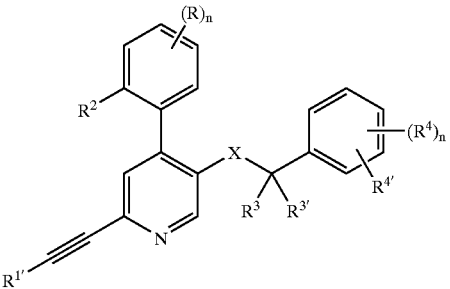

I-5 wherein the substituents are described above, or hydrogenating a compound of formula

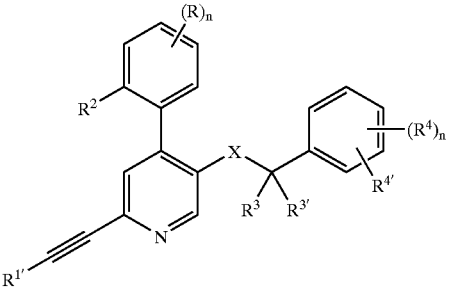

I-5 to compounds of formulas

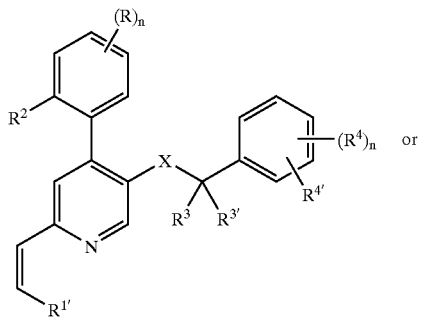

I-7

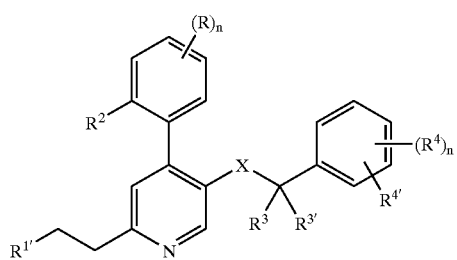

I-8 wherein the substituents are described above, or reacting a compound of formula

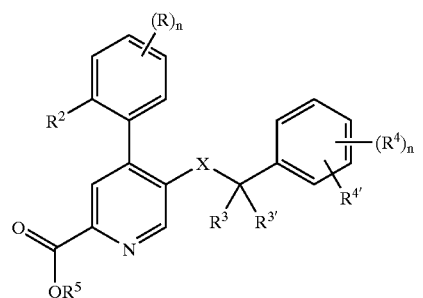

I-9 with HNR'R" to a compound of formula

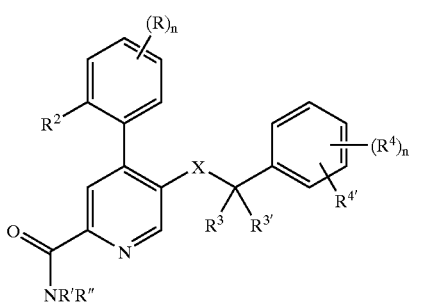

I-10 wherein the substituents are described above or reacting a compound of formula I-9 with LiBH$_4$ to a compound of formula

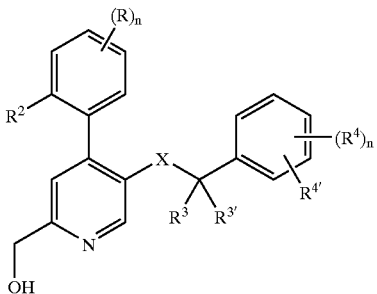

I-11 and, if desired, to a compound

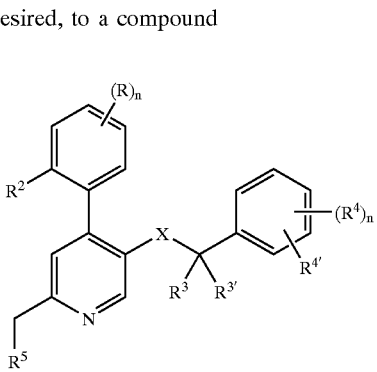

I-12 wherein the substituents are described above, or
reacting a compound of formula I-11 with R$^6$SH to compounds of formulas

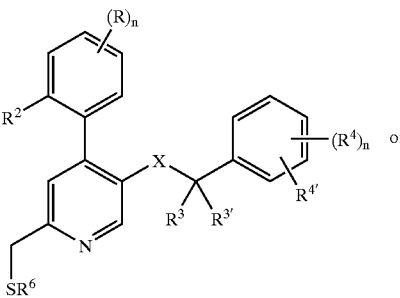

I-13

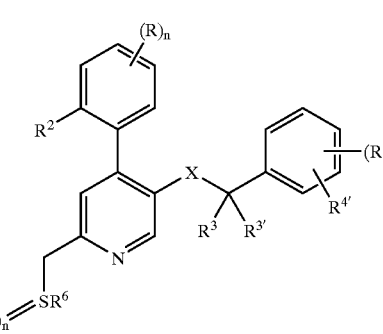

I-14 wherein the substituents are described above.

In accordance with process variant a) DIPEA (N-ethyldiisopropyl-amine) is added to a mixture of a compound of formula II and of a compound of formula III in dichloromethane and the mixture is stirred at temperatures between 25–40° C. The desired compound of formula Ia is isolated after purification in good yields.

Process variant b) describes the reaction of a compound of formula IV with a compound of formula V to a compound of formula Ib. The reaction is carried out in conventional manner, for example in a solvent, such as a mixture of toluene and triethylamine. The mixture is refluxed for about 1 hour.

In accordance with process variant c) a compound of formula Ib is reduced to a compound of formula Ic. This reaction is carried out with a reducing agent, such as LiAlH$_4$ or BH$_3$.THF, in conventional manner.

Process variant d) describes the reaction of a compound of formula VI with a compound of formula VII to a compound of formula Ib. This reaction is carried out by deprotonation of a compound of formula VI with KHMDS (potassium hexamethyldisilazide) and subsequent addition of a compound of formula VII. A suitable solvent is tetrahydrofuran. The reaction is carried out at room temperature.

In accordance with process variant e) a compound of formula Id is prepared. This reaction is carried out by deprotonation of a compound of formula VIII with NaH and susequent addition of a compound of formula VII. This reaction is carried out in conventional manner.

A further method for the preparation of a compound of formula I is described in process variant f). A compound of formula Ia is reduced to a compound of formula Ie in conventional manner, for example with LiAlH$_4$ or BH$_3$.THF.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–18 describe the processes for preparation of compounds of formula I in more detail. These reactions are carried out in conventional manner under conditions, described in the following schemes. The starting materials are known compounds or may be prepared according to methods known in the art.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |
| KHMDS | potassium hexamethyldisilazide |
| LDA | lithium diisopropylamide |
| DPPA | diphenylphosphoryl azide |
| EDC | hydrochloride |
| MCPBA | m-chloroperbenzoic acid |

Scheme 1

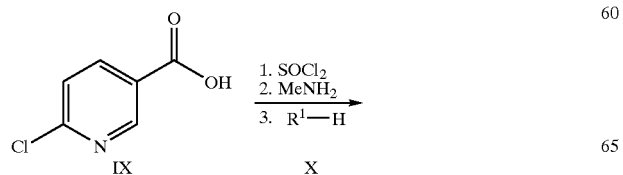

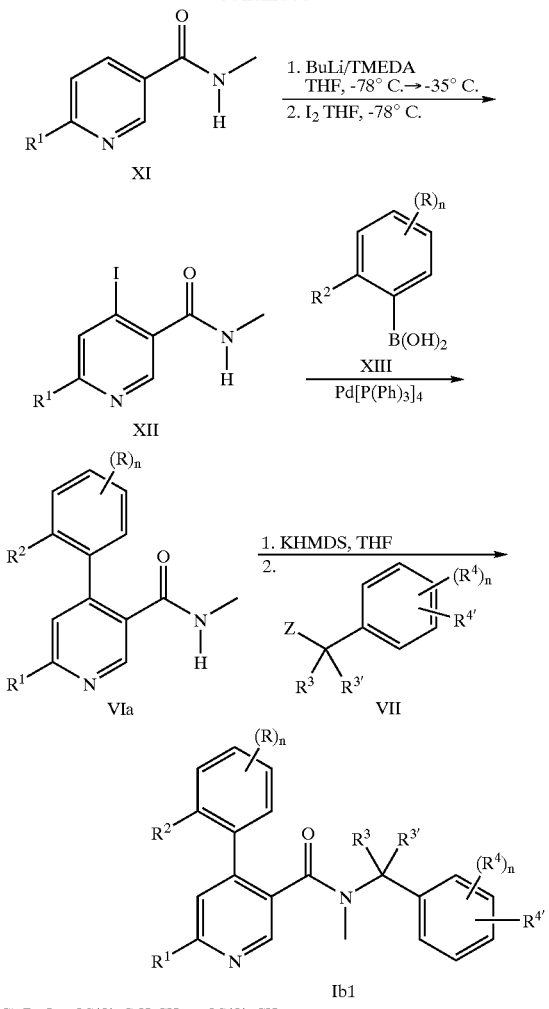

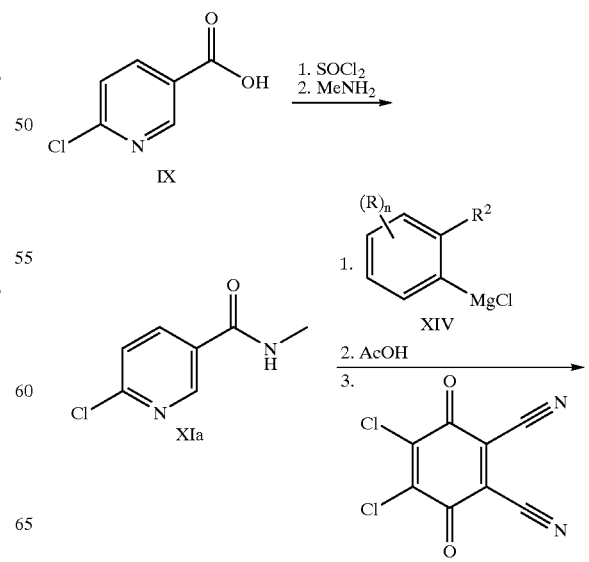

The substituents are described above.

Scheme 2

-continued

Scheme 4

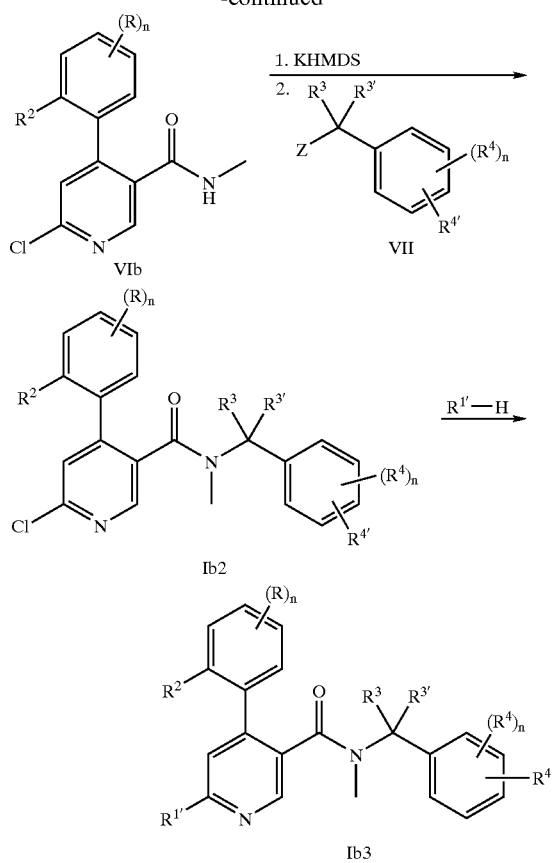

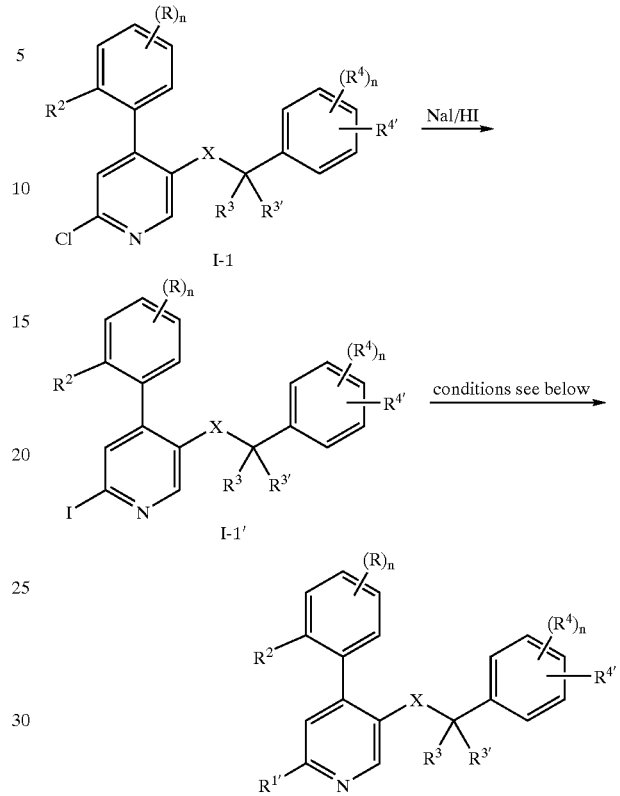

The substituents have the significances given above. $R^{1'}$ may be the same as for $R^1$, with the exception of chioro.

Scheme 3

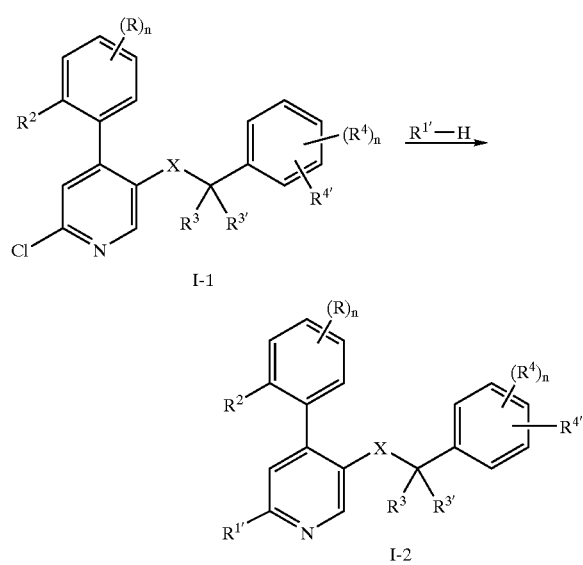

The substituents have the significances given above. $R^{1'}$ may be the same as for $R^1$, with the exception of chloro.

conditions:

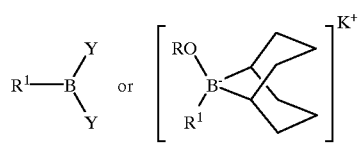

or $R^1$—$SnBU_3$ or $R^6$—SH or $R^6$—OH

Y=OH, OR, together $O(CR'R'')_qO$, R is hydrogen or lower alkyl, $R^1$ and $R^6$ are described above, R', R''=H, $CH_3$ q=2,3, or CO, $HO(CH_2)_mR^5$ or $H(C\equiv C)_mR^{1'}$ and cat. (Pd, Ni, Cu), m, $R^5$ and $R^{1'}$ are described above, or 1) RMgCl or RMgBr or RMgI or $R_2Mg$, wherein R is lower alkyl;

2)

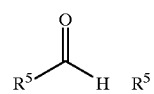

$R^5$ is described above;

The remaining substituents are described above.
Scheme 5
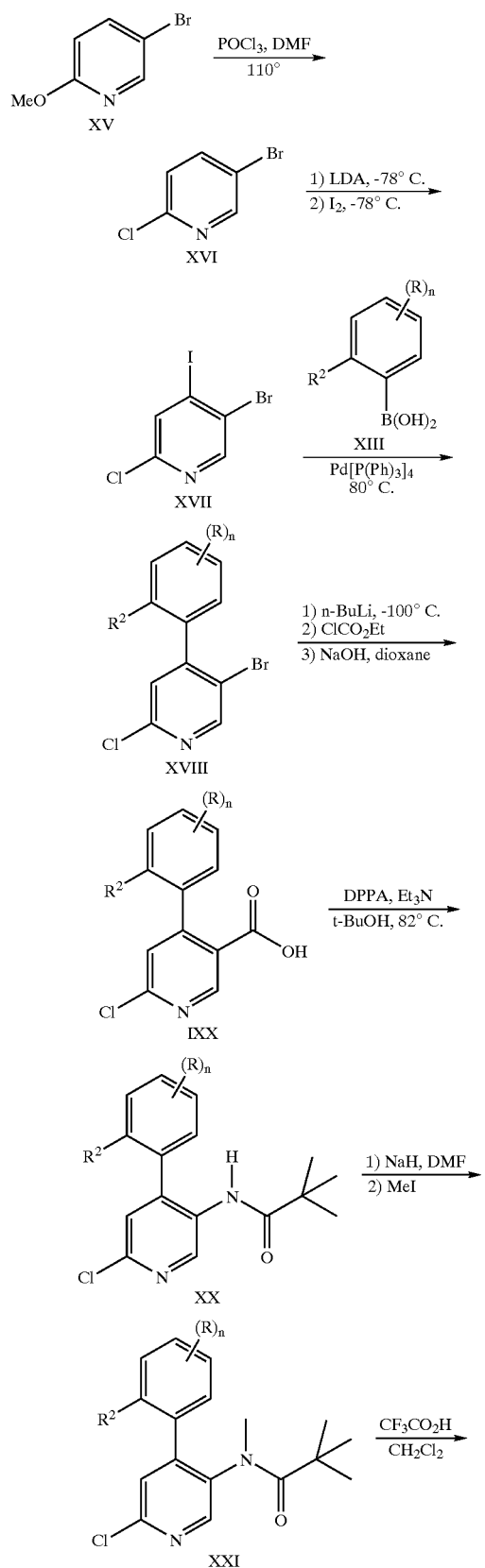
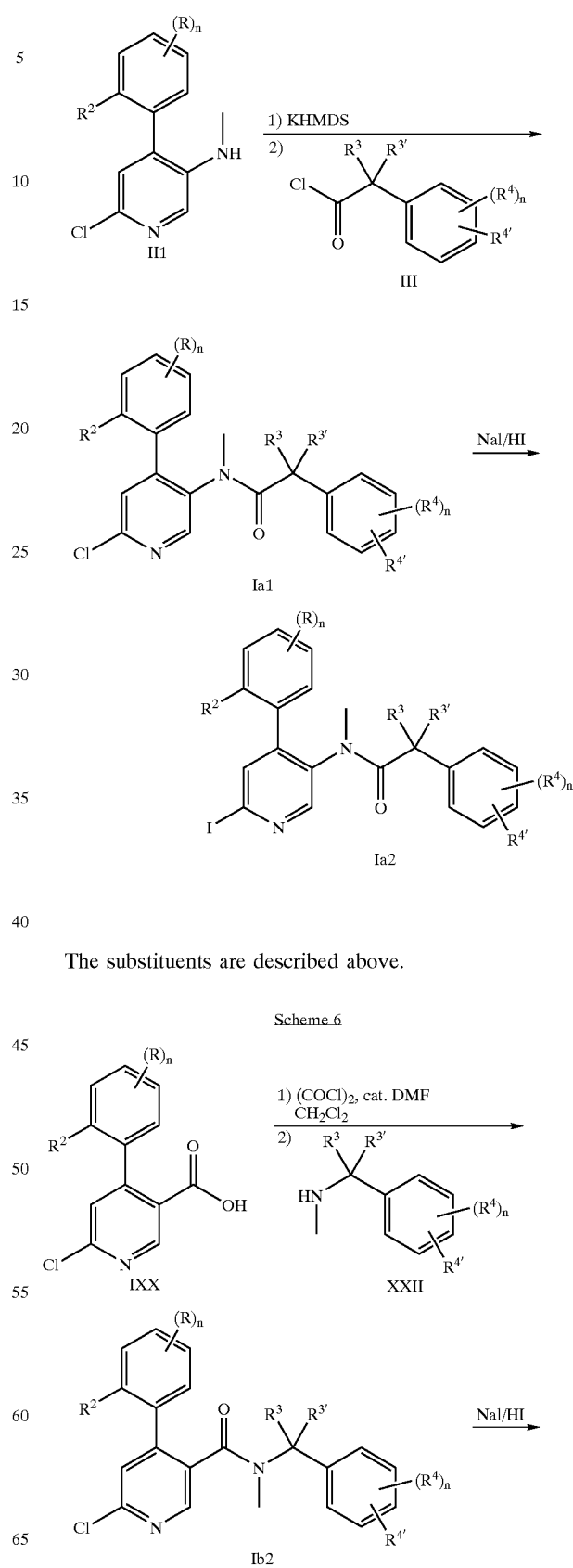
The substituents are described above.
Scheme 6
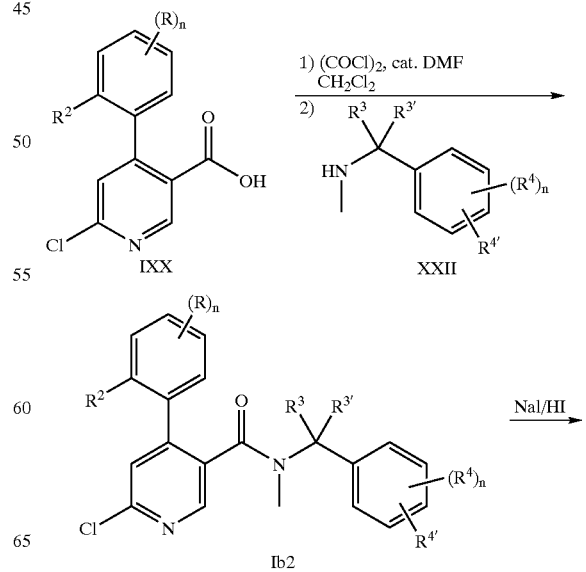

-continued
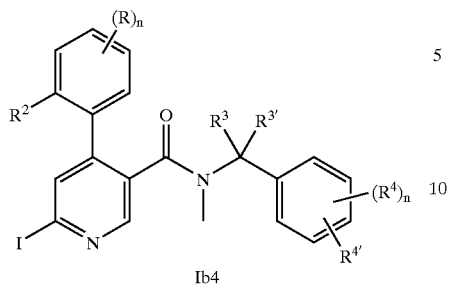
Ib4
The substituents are described above.
Scheme 7
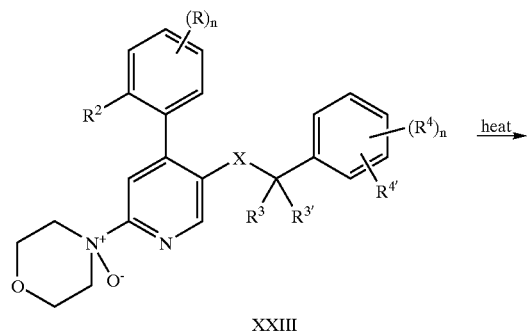
XXIII
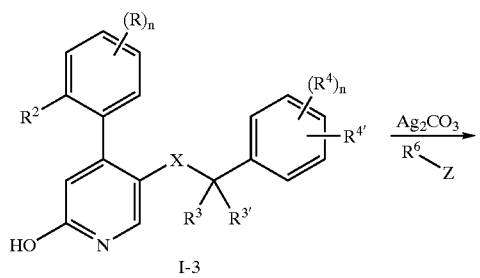
I-3
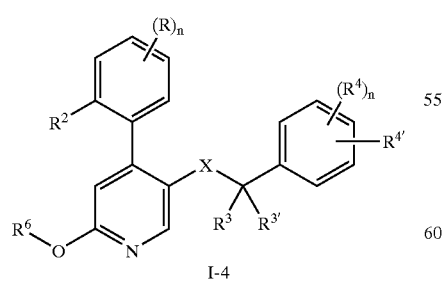
I-4
Z = Cl, Br, I or OS(O)₂C₆H₄CH₃ or OS(O)₂CH₃
The substituents are described as above.
Scheme 8
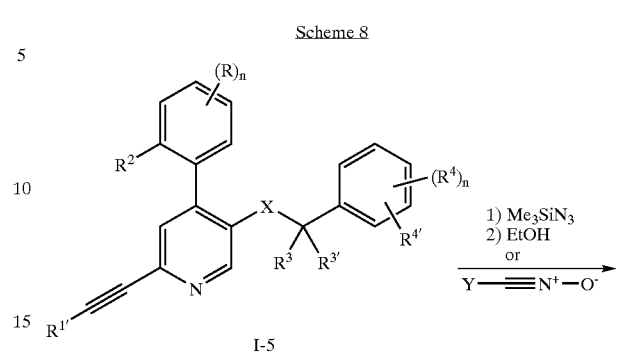
I-5
Y may be the substituation on the five or six membered heteroaryl group, described under m) for $R^{1'}$
$R^1$ is substituted m) for $R^1$
$R^{1'}$ is unsubstituted m) for $R^1$
Scheme 9
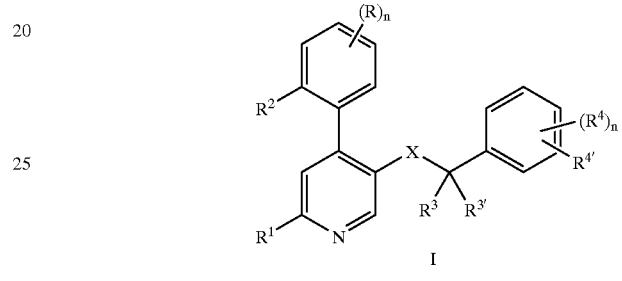
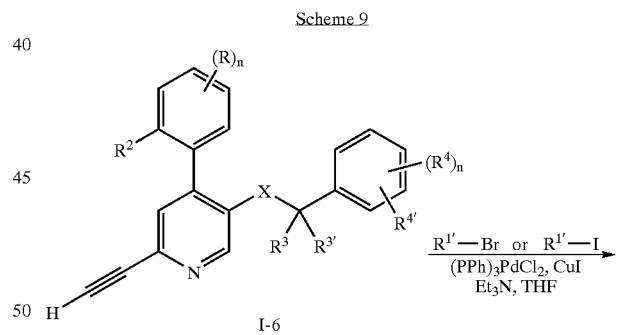
I-6
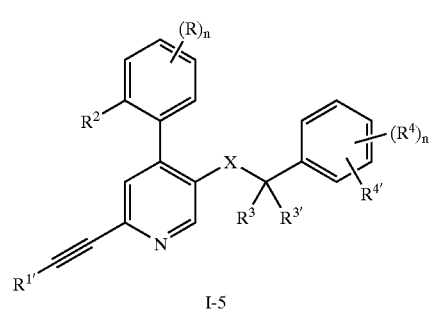
I-5
$R^{1'}$ = aryl or heteroaryl group Scheme 10
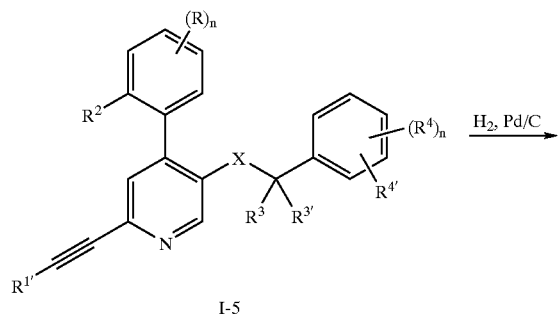
I-5
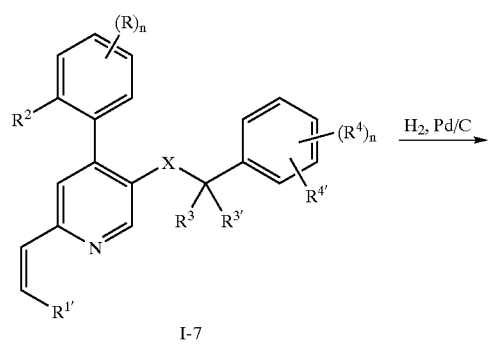
I-7
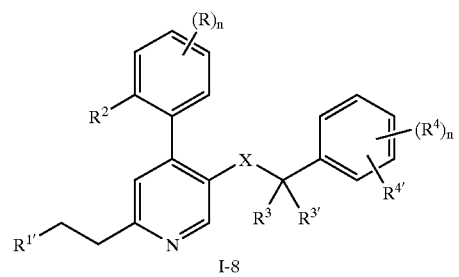
I-8
Scheme 11
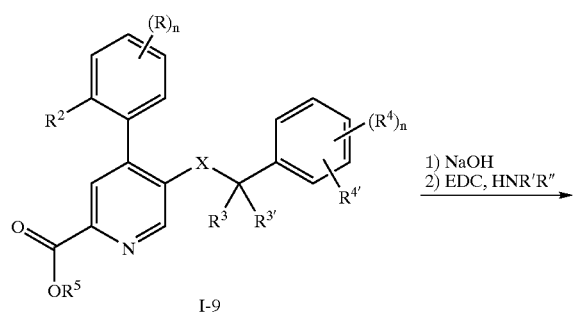
I-9
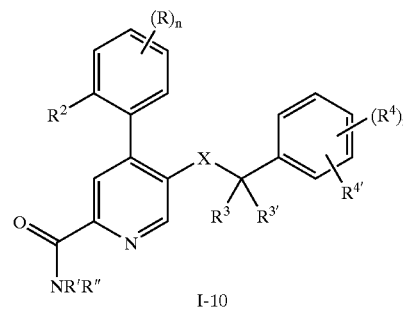
I-10
Scheme 12
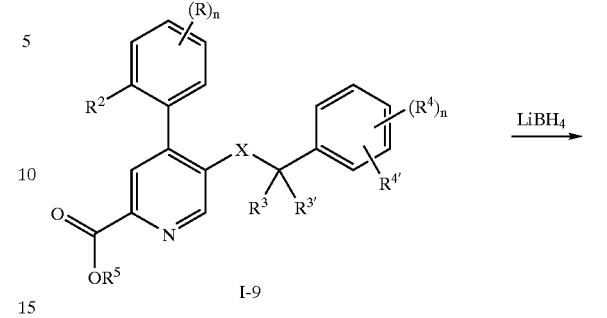
I-9
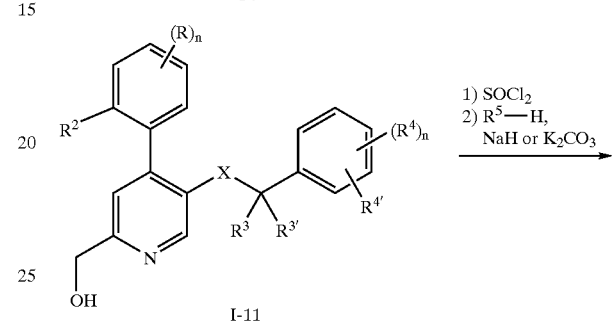
I-11
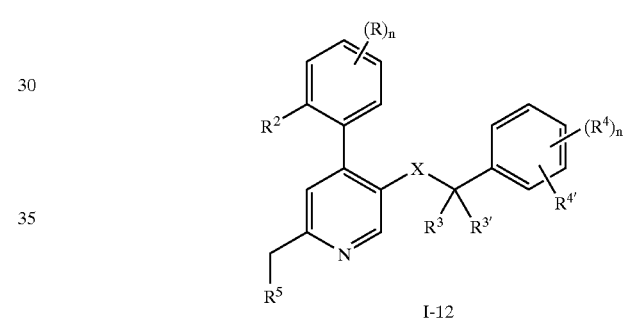
I-12
Scheme 13
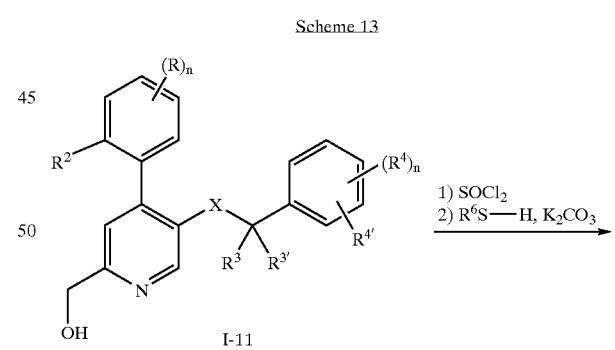
I-11
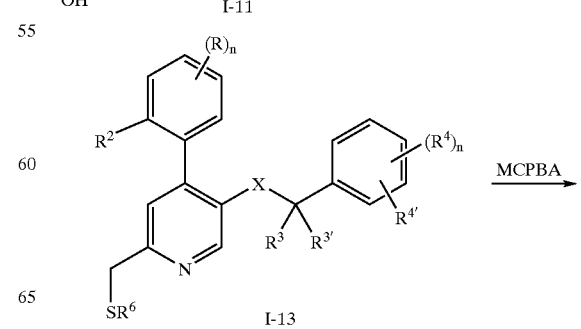
I-13

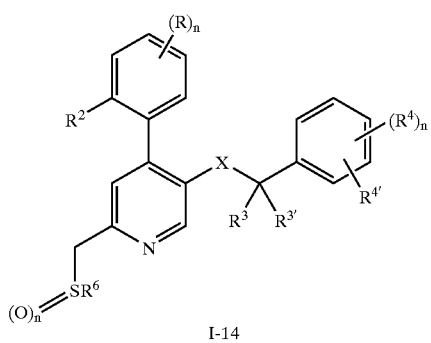
I-14
Scheme 14
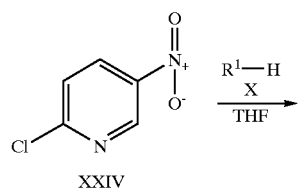
XXIV
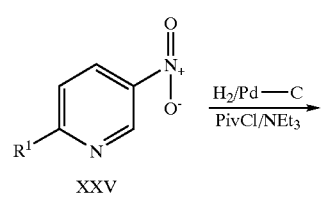
XXV
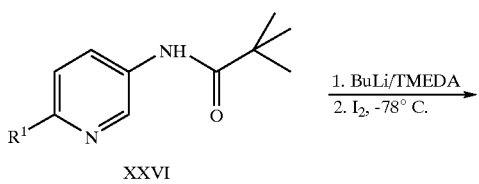
XXVI
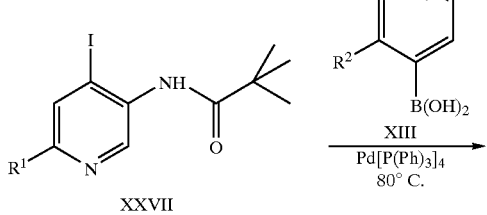
XXVII
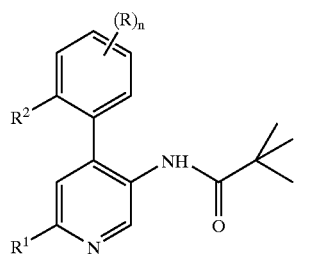
XX-1
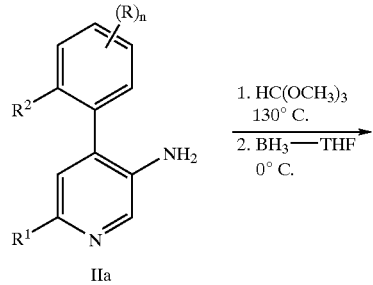
IIa
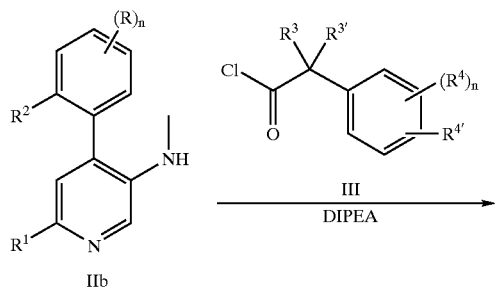
IIb
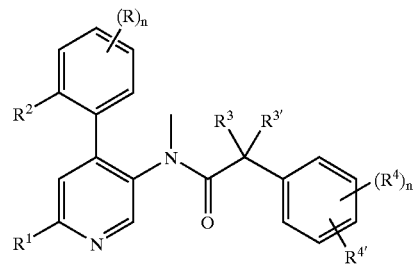
Ia1
The substituents have the significanes given above.
Scheme 15
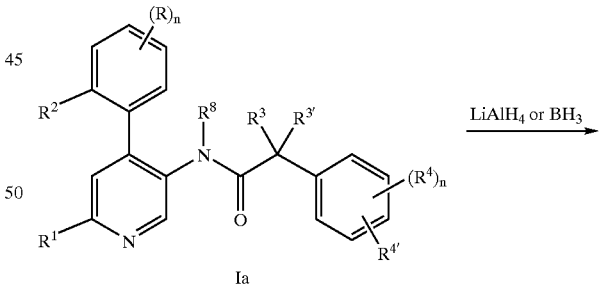
Ia
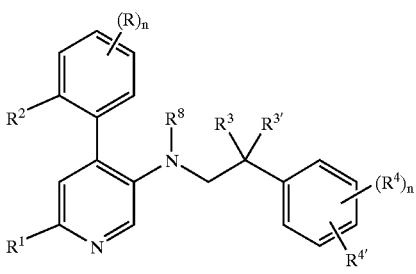
Ie The substituents have the significances given above.

Scheme 16

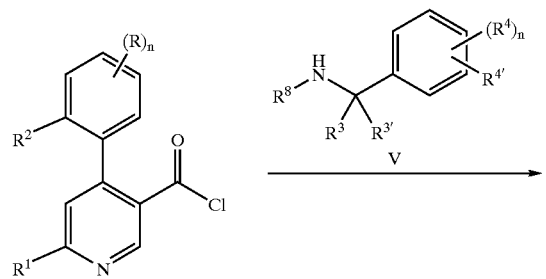

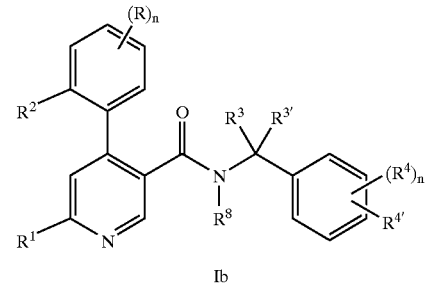

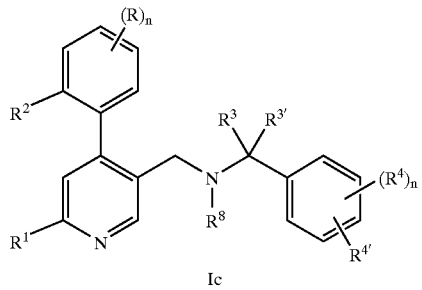

The substituents have the significances given above.

Scheme 17

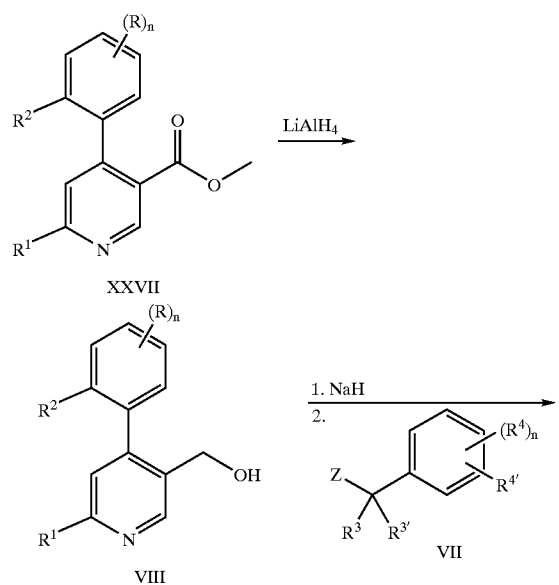

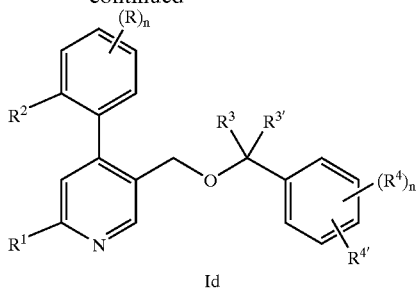

The substituents have the significances given above.

Scheme 18

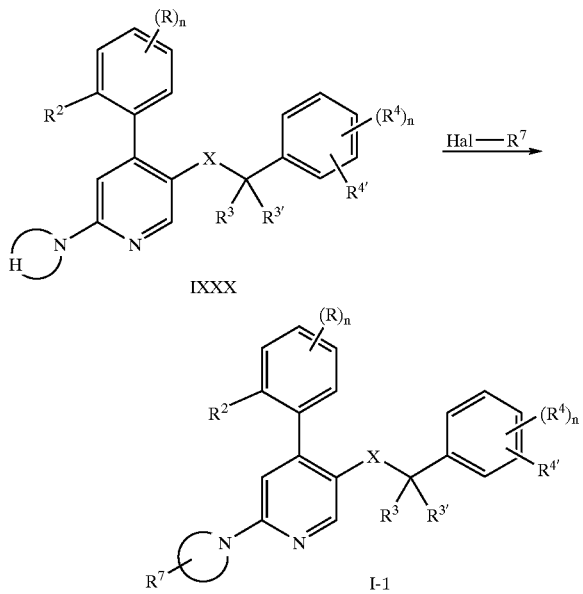

The substituents have the significances given above.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

All of the compounds were investigated in accordance with the tests given hereinafter.

The affinity of tests compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM.) Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension (1.25×10$^5$ cells/assay tube), 0.125 μl of bugger of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor for preferred compounds, given as pKi, is in the scope of 8.50–9.50 for the described compounds.

| Example No. | pKi |
|---|---|
| 8 | 9.29 |
| 13 | 8.79 |
| 16 | 8.5 |
| 26 | 8.65 |
| 38 | 8.67 |
| 42 | 9.08 |
| 62 | 8.52 |
| 66 | 8.57 |
| 99 | 8.58 |
| 113 | 8.78 |

All of the compounds of formula I as well as their pharmaceutically usable acid addition salts can be used as medicaments, e.g. in the form of pharmaceutical preparations. The pharmaceutical preparations can be administered orally, e.g. in the form of tables, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius. Compounds of examples 39, 54, 65, 81, 83, 92, 108, 109, 117 and 118 are out of the scope of the present formula I.

EXAMPLE 1

N-(3,5-Bis-trifluoromethyl-benzyl)-6-(4-hydroxyacetyl-piperazin-1-yl)-N-methyl-4-o-tolyl-nicotinamide a) 6-Chloro-N-methyl-nicotinamide To 50 g (317 mmol) of 2-chloronicotinic acid was added 230 ml (3.16 mol) thionyl chloride at 0° C. After heating the mixture at reflux for 2 h excess thionyl chloride was removed by distillation. The oily brown residue was dissolved in 250 ml dichloromethane. The solution was treated with methylamine gas at 0° C. until no exothermic reaction was observed any longer. The resulting suspension was diluted with 1000 ml dichloromethane/water. The layers were separated and the aqueous layer extracted with three 300 ml portions of dichloromethane. Drying of the organic layer with sodium sulfate and concentration gave 53.2 g (98%) of the title compound as a light yellow solid.

MS m/e (%): 171 (M+H$^+$, 15).

b) 6-Chloro-N-methyl-4-o-tolyl-nicotinamide

To a solution of 3.41 g (20.0 mmol) 6-chloro-N-methyl-nicotinamide in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic washed with 4 250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid. MS m/e (%): 260 (M$^{·+}$, 11). M.p. 91–93° C.

c) 4-(5-Methylcarbamoyl-4-o-tolyl-pyridin-2-yl)-piperazine-1-carboxylic acid tert-butyl ester A mixture of 8.31 g (31.9 mmol) 6-chloro-N-methyl-4-o-tolyl-nicotinamide, 6.53 g (35.0 mmol) 1-tert-butoxycarbonyl piperazine, 16.7 ml (95.6 mmol) N-ethyldiisopropylamine and a catalytic amount of 4-(N,N-dimethylamino)-pyridine was heated at reflux over night. After cooling to room temperature the mixture was dissolved in dichloromethane and washed with two portions of 0.1 M aqueous hydrochloric acid solution. Drying with sodium sulfate and concentration gave 10.7 g of the crude product. Flash column chromatography afforded 6.28 g (48.0%) of the title compound as an off-white solid. S m/e (%): 411 (M+H$^+$, 100).

d) 4-{5-[(3,5-Bis-trifluoromethyl-benzyl)-methyl-carbamoyl]-4-o-tolyl-pyridin-2-yl}-piperazine-1-carboxylic acid tert-butyl ester To a solution of 6.28 g (15.3 mmol) 4-(5-methylcarbamoyl-4-o-tolyl-pyridin-2-yl)-piperazine-1-carboxylic acid tert-butyl ester in 250 ml tetrahydrofuran 20 ml of a 1 M solution (20 mmol) of potassium hexamethyldisilazide in tetrahydrofuran were added at 0° C. After 30 min, 2.81 ml (15.3 mmol) 3,5-bis(trifluoromethyl)benzyl bromide were added dropwise. The reaction mixture was allowed to warm to room temperature over night. Addition of water and 1 M aqueous sodium hydroxide solution was followed by extraction with three portions of ethyl acetate. The combined organic extracts were dried with sodium sulfate and concentrated. Flash column chromatography gave 6.89 g (70.8%) of the title compound as a white solid. MS m/e (%): 637 (M+H$^+$, 100).

e) N-(3,5-Bis-trifluoromethyl-benzyl)-N-methyl-6-piperazin-1-yl-4-o-tolyl-nicotinamide To a solution of 6.60 g (104 mmol) 4-{5-[(3,5-bis-trifluoromethyl-benzyl)-methyl-carbamoyl]-4-o-tilyl-pyridin-2-yl}-piperazine-1-carboxylic acid tert-butyl ester and 8.40 ml (207 mmol) methanol in 50 ml ethyl acetate 14.7 ml (207 mmol) acetyl chloride were added dropwise at 0° C. After 4 h the reaction mixture was diluted with ethyl acetate and treated with 1 M sodium hydroxide solution. The layers were separated and the aqueous layer extracted with dichloromethane. The combined organic layers were dried with sodium sulfate and concentrated to give 5.36 g of crude product. Flash column chromatography afforded 4.86 g (87.4%) of the title compound as a light brown solid. MS m/e (%): 537 (M+H$^+$, 100).

f) N-(3,5-Bis-trifluoromethyl-benzyl)-6-(4-bromoacetyl-piperazin-1-yl)-N-methyl-4-o-tolyl-nicotinamide To a solution of 0.30 g (0.56 mmol) N-(3, 5-bis-trifluoromethyl-benzyl)-N-methyl-6-piperazin-1-yl-4-o-tolyl-nicotinamide in 4 ml dichloromethane 0.055 ml (0.62 mmol) bromoacetyl bromide and 4 ml of a 2M aqueous sodium carbonate solution were consecutively added dropwise at 10° C. After 2 h the reaction mixture was diluted with water and extracted with dichloromethane. The organic extract was dried with sodium sulfate and concentrated to give 0.36 g of crude product. Flash column chromatography afforded 0.26 g (69%) of the title compound as a white solid. MS m/e (%): 657 (M+H$^+$, 100, 1 Br).

g) N-(3,5-Bis-trifluoromethyl-benzyl)-6-(4-hydroxyacetyl-piperazin-1-yl)-N-methyl-4-o-tolyl-nicotinamide A mixture of 0.12 g (0.18 mmol) N-(3,5-bis-trifluoromethyl-benzyl)-6-(4-bromoacetyl-piperazin-1-yl)-N-methyl-4-o-tolyl-nicotinamide, 1.2 ml 1-methyl-2-pyrrolidone and 0.2 ml half-saturated aqueous sodium bicarbonate solution was stirred at 100° C. over night. After cooling to room temperature and dilution with water the mixture was extracted with five portions of tert-butyl methyl ether. The combined organic extracts were dried with sodium sulfate, concentrated and dried in vacuo (0.5 mbar) at 70°. Flash column chromatography afforded 71 mg (64%) of the title compound as a white solid.

MS m/e (%): 595 (M+H$^+$, 100).

EXAMPLE 2

N-(3,5-Bis-trifluoromethyl-benzyl)-6-chloro-N-methyl-4-o-tolyl-nicotinamide

To a solution of 10.0 g (38.4 mmol) 6-chloro-N-methyl-4-o-tolyl-nicotinamide in 190 ml tetrahydrofuran 46 ml of a 1 M solution (46 mmol) of potassium hexamethyldisilazide in tetrahydrofuran were added at 0° C. After 30 min, 8.5 ml (46 mmol) 3,5-bis(trifluoromethyl)benzyl bromide were added dropwise to the resulting suspension. After completed addition the ice-water cooling bath was removed and the reaction mixture was allowed to warm to room temperature. After 2 h the reaction was quenched with water. The mixture was adjusted to pH 3 with 1 M aqueous hydrochloric acid solution and stirred for 10 min. Basification with 1 M aqueous sodium hydroxide solution to pH 8 was followed by concentration to remove tetrahydrofuran. The aqueous residue was extracted with four portions of dichloromethane. The combined organic extracts were dried with sodium sulfate and concentrated to give 21.4 g of crude product. Column chromatography afforded 18.4 g (98.5%) of the title compound as a white solid.

MS m/e (%): 485 ([M–H]$^+$, 2).

EXAMPLE 3

N-(3,5-Bis-trifluoromethyl-benzyl)-6-cyanomethyl-N-methyl-4-o-tolyl-nicotinamide a) (RS)-{5-[(3,5-Bis-trifluoromethyl-benzyl)-methyl-carbamoyl]-4-o-tolyl-pyridin-2-yl}-cyano-acetic acid ethyl ester A mixture of 1.00 g (2.05 mmol) N-(3,5-bis-trifluoromethyl-benzyl)-6-chloro-N-methyl-4-o-tolyl-nicotinamide, 0.44 ml (4.1 mmol) ethyl cyanoacetate and 0.46 g (4.1 mmol) potassium tert-butoxide in 2 ml dimethyl sulfoxide was stirred at 100° C. over night. After cooling to room temperature 10 ml of a half-concentrated aqueous solution of ammonium chloride was added. The mixture was extracted with 3 portions of ethyl acetate. The combined organic extracts were washed with two portions of water, dried with sodium sulfate and concentrated to give 1.2 g of crude product. Flash chromatography afforded 0.681 g (58.8%) of the title compound as a yellow foam.

MS m/e (%): 563 (M$^+$, 80).

b) N-(3,5-Bis-trifluoromethyl-benzyl)-6-cyanomethyl-N-methyl-4-o-tolyl-nicotinamide A mixture of 650 mg (1.15 mmol) (RS)-{5-[(3,5-bis-trifluoromethyl-benzyl)-methyl-carbamoyl]-4-o-tolyl-pyridin-2-yl}-cyano-acetic acid ethyl ester and 0.20 g (4.6 mmol) lithium chloride in wet dimethyl sulfoxide was stirred at 120° C. over night. After cooling the mixture was concentrated in vacuo. The residue was dissolved in ethyl acetate and a saturated aqueous solution of sodium bicarbonate. The layers were separated and the aqueous layer was extracted with two portions of ethyl acetate. The combined organic extracts were washed with two portions of water, dried with magnesium sulfate and concentrated to give 595 mg of crude product. Flash chromatography afforded 396 mg (69.9%) of the title compound as a white solid.

MS m/e (%): 492 (M+H$^+$, 100).

EXAMPLE 4

N-(3,5-Bis-trifluoromethyl-benzyl)-6-iodo-N-methyl-4-o-tolyl-nicotinamide

To a solution of 1.00 g (2.05 mmol) N-(3,5-bis-trifluoromethyl-benzyl)-6-chloro-N-methyl-4-o-tolyl-nicotinamide in 10 ml 2-butanone 1.1 g (7.2 mmol) sodium iodide and 0.28 ml (2.1 mmol) hydroiodic acid (57% in water) were added at room temperature. The mixture was heated at 80° C. for 2 h. After cooling to room temperature the mixture was diluted with ethyl acetate and treated with saturated aqueous sodium bicarbonate solution. The layers were separated, the organic layer washed with water, dried with magnesium sulfate and concentrated to give 1.5 g of crude product. Flash column chromatography gave 1.11 g (93.6%) of the title compound as a yellow oil.

MS m/e (%): 579 (M+H$^+$, 100).

EXAMPLE 5

4-o-Tolyl-[2,4']bipyridinyl-5-carboxylic acid (3,5-bis-trifluoromethyl-benzyl)-methyl-amide A mixture of 100 mg (0.173 mmol) N-(3,5-bis-trifluoromethyl-benzyl)-6-iodo-N-methyl-4-o-tolyl-nicotinamide, 21 mg (0.17 mmol) 4-pyridylboronic acid, 5 ml dimethoxyethane and 5 ml of a 2 M aqueous solution of sodium carbonate was deoxygenated by three freeze-thaw cycles. After addition of 20 mg (0.017 mmol) tetrakis(triphenylphosphine)palladium(0) the reaction mixture was stirred at 90° C. for 60 h. Cooling to room temperature was followed by dilution with water and extraction with 3 portions of ethyl acetate. The organic extract was washed with water, dried with magnesium sulfate and concentrated. Column chromatography afforded 59 mg (64%) of the title compound as a yellow solid.

MS m/e (%):530 (M+H$^+$, 100).

EXAMPLE 6

5-[(3,5-Bis-trifluoromethyl-benzyl)-methyl-carbamoyl]-4-o-tolyl-pyridine-2-carboxylic acid methyl ester A solution of 690 mg (1.19 mmol) N-(3,5-bis-trifluoromethyl-benzyl)-6-iodo-N-methyl-4-o-tolyl-nicotinamide, 0.33 ml (2.4 mmol) triethylamine and 1.9 ml (48 mmol) methanol in 10 ml N,N-dimethylformamide was deoxygenated by three freeze-thaw cycles. Filling the flask with carbon monoxide gas from a balloon was followed by addition of 31 mg (0.12 mmol) triphenylphosphine and 23 mg (0.102 mmol) palladium(II) acetate. The reaction mixture was stirred for 60 h under an atmosphere of carbon monoxide gas at room temperature. The mixture was diluted with water and extracted with 3 portions of tert-butyl methyl ether. The combined organic extracts were washed with water, dried with sodium sulfate and concentrated. Flash chromatography afforded 407 mg (66.8%) of the title compound as a light-yellow solid.

MS m/e (%): 511 (M+H$^+$, 100).

EXAMPLE 7

N-(3,5-Bis-trifluoromethyl-benzyl)-6-hydroxymethyl-N-methyl-4-o-tolyl-nicotinamide To a solution of 9 mg (4 mmol) lithium borohydride in 0.5 ml diethyl ether was added a solution of 346 mg (0.678 mmol) 5-[(3,5-bis-trifluoromethyl-benzyl)-methyl-carbamoyl]-4-o-tolyl-pyridine-2-carboxylic acid methyl ester in 0.6 ml toluene. The mixture was gradually heated to 100° C., whereby diethyl ether was distilled off. After heating for 2 h at 100° C. the resulting suspension was concentrated. The residue was treated with 5 ml of a 1 M aqueous solution of hydrochloric acid for 5 min. Basification with potassium carbonate was followed by extraction with tert-butyl methyl ether. The combined organic extracts were dried with sodium sulfate and concentrated. Flash chromatography afforded 240 mg (73.4%) of the title compound as a light brown oil.

MS m/e (%): 481 (M–H, 6).

EXAMPLE 8

2-(3,5-Bis-trifluoromethyl-phenyl)-N-{6-[hydroxy-(2-hydroxy-ethyl)-amino]-4-o-tolyl-pyridin-3-yl}-N-methyl-isobutyramide a) 4-(5-Nitro-2-pyridyl)-morpholine To a solution of 20 g (126 mmol) of 2-chloro-5-nitropyridine in 150 ml tetrahydrofuran were added dropwise 27 ml (315 mmol) morpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.3 g (quantitative) of the title compound as a yellow solid. M.p. 142–143° C.

b) 2,2-Dimethyl-N-(6-morpholin-4-yl-pyridin-3-yl)-propionamide

To a solution of 27.3 g (126 mmol) of 4-(5-nitro-2-pyridyl)-morpholine in 600 ml methanol were added 2.5 g of 10% of palladium on activated charcoal. The reaction mixture was hydrogenated (room temperature to ca. 45° C., 1 bar) until the theoretical amount of hydrogen was taken up (about 3 h). The catalyst was filtered off and was washed twice with 100 ml portions of methanol. The filtrate was evaporated in vacuo to give 22.6 g of a purple oil which consisted to ca. 95% of the desired aniline derivative according to analysis by thin layer chromatography.

This crude product was dissolved in a mixture of 240 ml tetrahydrofuran and 60 ml diethyl ether. After cooling to 0° C., 26 ml (189 mmol) of triethylamine were added in one portion. Stirring was continued while 23 g (189 mmol) of pivaloyl chloride were added dropwise within a period of 10 min. The ice bath was removed and the reaction mixture was stirred for 1 h at room temperature. Then, the solvent was removed in vacuo and the residue was suspended in 200 ml 1 N sodium bicarbonate solution. The product was extracted three times with 200 ml portions of dichloromethane, dried (sodium sulfate) and evaporated. Recrystallization of the solid residue from ethyl acetate/hexane 1:8 gave 28.6 g (86%) of the title compound as white crystals.

MS m/e (%): 264 (M+H$^+$, 100).

c) N-(4-Iodo-6-morpholin-4-yl-pyridin-3-yl)-2,2-dimethyl-propionamide

A solution of 28.4 g (108 mmol) 2,2-dimethyl-N-(6-morpholin-4-yl-pyridin-3-yl)-propionamide and 49 ml (324 mmol) N,N,N',N'-tetramethylethylenediamine under argon in 600 ml tetrahydrofuran was cooled in a dry ice bath to −78° C. Within 1 h, 202 ml (324 mmol) of a 1.6 N n-butyllithium solution in hexane were added dropwise. The reaction mixture was allowed to warm up to −35° C. overnight. After cooling again to −78° C., 37 g (146 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 15.6 g (37%) of the title compound as a light brown oil which crystallized upon standing at room temperature.

MS m/e (%): 389 (M$^+$, 71), 358 (25), 304 (43), 57 (100).

d) 2,2-Dimethyl-N-(6-morpholin-4-yl-4-o-tolyl-pyridin-3-yl)-propionamide

A mixture of 3.50 g (9.0 mmol) N-(4-iodo-6-morpholin-4-yl-pyridin-3-yl)-2,2-dimethyl-propionamide, 35 ml toluene, 18 ml 2 N sodium carbonate solution, 312 mg (0.27 mmol) tetrakis(triphenylphosphine)palladium(0) and 1.34 g (9.9 mmol) o-tolylboronic acid was heated under argon at 80° C. for 12 h. After cooling to room temperature, the aqueous phase was separated and washed twice with ethyl acetate. The combined organic layers were washed with 50 ml brine, dried (sodium sulfate) and evaporated. Purification by flash-chromatography gave 3.23 g (quantitative) of the title compound as a white foam.

MS m/e (%): 354 (M+H$^+$, 100).

e) 6-Morpholin-4-yl-4-o-tolyl-pyridin-3-ylamine

A suspension of 2.93 g (8.28 mmol) 2,2-dimethyl-N-(6-morpholin-4-yl-4-o-tolyl-pyridin-3-yl)-propionamide in 80 ml 3 N hydrochloric acid solution and 5 ml 1-propanol was heated to 90–95° C. overnight. The reaction mixture was cooled to room temperature, washed with three 20 ml portions diethyl ether and filtered over celite. The filtrate was diluted with 20 ml water and was adjusted to pH 7–8 by addition of 28% sodium hydroxide solution under ice cooling. The product was extracted with four 100 ml portions of dichloromethane. The combined organic layers were washed with 50 ml brine, dried (magnesium sulfate) and evaporated to give 2.31 g (quantitative) of the title compound as a white foam.

MS m/e (%): 269 (M$^+$, 100).

f) Methyl-(6-morpholin-4-yl-4-o-tolyl-pyridin-3-yl)-amine

A solution of 2.24 g (8.3 mmol) 6-morpholin-4-yl-4-o-tolyl-pyridin-3-ylamine in 17 ml trimethyl orthoformate and 3 drops trifluoroacetic acid was heated for 2 h at 130° C. The reaction mixture was evaporated and dried in vacuo for 30 min. The residual oil was dissolved in 5 ml tetrahydrofuran and was added dropwise under ice cooling to 630 mg (16.6 mmol) lithium aluminum hydride in 20 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 1.56 g (66%) of the title compound as a white foam.

MS m/e (%): 283 (M$^+$, 100).

g) 2-(3,5-Bis-trifluoromethyl-phenyl)-N-methyl-N-(6-morpholin-4-yl-4-o-tolyl-pyridin-3-yl)-isobutyramide A solution of 1.46 g (5.15 mmol) methyl-(6-morpholin-4-yl-4-o-tolyl-pyridin-3-yl)-amine and 1.32 ml (7.73 mmol) N-ethyldiisopropylamine in 15 ml dichloromethane was cooled in an ice bath and 1.8 g (5.67 mmol) 2-(3,5-bis-trifluoromethyl-phenyl)-2-methyl-propionyl chloride were added dropwise. The reaction mixture was warmed to 35–40° C. for 3 h, cooled to room temperature again and was stirred with 25 ml saturated sodium bicarbonate solution. The organic layer was separated and the aqueous phase was extracted with dichloromethane. The combined organic layers were dried (magnesium sulfate) and evaporated. The residue was purified by flash chromatography to give 2.9 g (quantitative) of the title compound as white crystals. M.p. 131–132° C.

h) 2-(3,5-Bis-trifluoromethyl-phenyl)-N-[6-(2-hydroxy-ethylamino)-4-o-tolyl-pyridin-3-yl]-N-methyl-isobutyramide A mixture of 1.0 g (1.76 mmol) 2-(3,5-bis-trifluoromethyl-phenyl)-N-methyl-N-(6-morpholin-4-yl-4-o-tolyl-pyridin-3-yl)-isobutyramide, 100 mg (0.48 mmol) ruthenium(III)chloride hydrate, 832 mg (3.87 mmol) sodium periodate, 3.5 ml carbon tetrachloride, 3.5 ml acetonitrile and 5.3 ml water was stirred for 4 days at room temperature. Dichloromethane was added, the organic layer was separated, washed with sodium hydrogensulfite solution and filtered over celite. To the filtrate were added 10 ml 1 N potassium hydroxide solution and 20 ml methanol. After heating the mixture for 1 h at 40° C., the solvents were removed in vacuo and the residue was purified by flash-chromatography to give 352 mg (37%) of the title compound as light brown foam.

MS m/e (%): 540 (M+H$^+$, 100).

i) 2-(3,5-Bis-trifluoromethyl-phenyl)-N-{6-[hydroxy-(2-hydroxy-ethyl)-aminol -4-o-tolyl-pyridin-3-yl}-N-methyl-isobutyramide To a solution of 500 mg (0.93 mmol) 2-(3,5-bis-trifluoromethyl-phenyl)-N-[6-(2-hydroxy-ethylamino)-4-o-tolyl-pyridin-3-yl]-N-methyl-isobutyramide in 5 ml dichloromethane was added under ice cooling a solution of 240 mg (0.97 mmol) of 3-chloroperbenzoic acid (ca. 70%) in 5 ml dichloromethane. After stirring for 2 h at 0° C., the reaction mixture was washed twice with saturated sodium carbonate solution, dried (sodium sulfate) and evaporated. The crude material was suspended in a mixture of dichloromethane and hexane, filtered and dried in vacuo to give 345 mg (62%) of the title compound as white crystals.

MS m/e (%): 556 (M+H$^+$, 100).

EXAMPLE 9

2-(3,5-Bis-trifluoromethyl-phenyl)-N-{4-(2-chloro-phenyl)-6-[hydroxy-(2-hydroxy-ethyl)-amino]-pyridin-3-yl}-N-methyl-isobutyramide The title compound was obtained as light brown foam in comparable yield according to the procedure described above for the preparation of 2-(3,5-bis-trifluoromethyl-phenyl)-N-{6-[hydroxy-(2-hydroxy-ethyl)-amino]-4-o-tolyl-pyridin-3-yl}-N-methyl-isobutyramide using 2-chlorophenylboronic acid instead of o-tolylboronic acid in step d).

MS m/e (%): 576 (M+H$^+$, 100).

EXAMPLE 10

2-(3,5-Bis-trifluoromethyl-phenyl)-N-methyl-N-[6-(3-oxo-morpholin-4-yl)-4-o-tolyl-pyridin-3-yl]-isobutyramide To an ice-cooled suspension of 1.2 g (7.12 mmol) ruthenium(IV)oxide hydrate in a mixture of 50 ml carbon tetrachloride and 50 ml water were added 9.0 g (42 mmol) sodium periodate. After stirring for 30 min the organic layer was separated and the aqueous layer was extracted twice with 10 ml portions of carbon tetrachloride. The combined organic layers were filtered over celite, cooled to 0° C. and were added slowly to an ice-cooled solution of 2.0 g (3.54 mmol) 2-(3,5-bis-trifluoromethyl-phenyl)-N-methyl-N-(6-morpholin-4-yl-4-o-tolyl-pyridin-3-yl)-isobutyramide in 20 ml carbon tetrachloride. The mixture was stirred for additional 15 min at 0° C., was filtered over celite and was evaporated. The residue was purified by flash-chromatography and gave 704 mg (34%) of the title compound as colourless foam.

MS m/e (%): 580 (M+H$^+$, 100).

EXAMPLE 11

2-(3,5-Bis-trifluoromethyl-phenyl)-N-[4-(2-chloro-phenyl)-6-(3-oxo-morpholin-4-yl)-pyridin-3-yl]-N-methyl-isobutyramide The title compound was obtained as light brown oil in comparable yields according to the procedures described above for the preparation of 2-(3,5-bis-trifluoromethyl-phenyl)-N-methyl-N-[6-(3-oxo-morpholin-4-yl)-4-o-tolyl-pyridin-3-yl]-isobutyramide.

MS m/e (%): 600 (M+H$^+$, 100).

EXAMPLE 12

Acetic acid (5-{[2-(3,5-bis-trifluoromethyl-phenyl)-2-methyl-propionyl]-methyl-amino}-4-o-tolyl-pyridin-2-ylcarbamoyl)-methyl ester a) N2-Benzyl-N5-methyl-4-o-tolyl-pyridine-2,5-diamine The title compound was prepared following the procedures described above for the synthesis of methyl-(6-morpholin-4-yl-4-o-tolyl-pyridin-3-yl)-amine.

MS m/e (%): 304 (M+H$^+$, 100).

b) Benzyl-(5-methylamino-4-o-tolyl-pyridin-2-yl)-carbamic acid benzyl ester

To a solution of 2.03 g (6.7 mmol) N$^2$-benzyl-N$^5$-methyl-4-o-tolyl-pyridine-2,5-diamine in 100 ml dichloromethane and 40 ml N-ethyldiisopropylamine was added dropwise at 0° C. a solution of 2.1 ml (14.09 mmol) benzyl chloroformate in 50 ml dichloromethane. After stirring for 2 h at room temperature the reaction mixture was washed with water (2×50 ml), brine (50 ml), dried (magnesium sulfate) and evaporated. Chromatography of the residue afforded 2.36 g (80%) of the title compound as light brown crystals. M.p. 110–112° C.

MS m/e (%): 438 (M+H$^+$, 100).

c) Benzyl-(5-{[2-(3,5-bis-trifluoromethyl-phenyl)-2-methyl-propionyl]-methyl-amino}-4-o-tolyl-pyridin-2-yl)-carbamic acid benzyl ester To a solution of 1.075 g (2.5 mmol) benzyl-(5-methylamino-4-o-tolyl-pyridin-2-yl)-carbamic acid benzyl ester in 10 ml dichloromethane and 1 ml N-ethyldiisopropylamine was added dropwise at 0° C. a solution of 1.15 g (3.5 mmol) 2-(3,5-bis-trifluoromethyl-phenyl)-2-methyl-propionic acid chloride in 2 ml dichloromethane and the mixture was stirred for 3 h at room temperature. The solution was washed with water (20 ml), saturated aqueous sodium hydrogencarbonate solution (20 ml) and brine (20 ml), dried (magnesium sulfate) and evaporated. Chromatography of the residue afforded 1.15 g (62%) of the title compound as a yellow oil.

MS m/e (%): 720 (M+H$^+$, 100).

d) N-(6-Benzylamino-4-o-tolyl-pyridin-3-yl)-2-(3,5-bis-trifluoromethyl-phenyl)-N-methyl-isobutyramide To a solution of 973 mg (1.35 mmol) benzyl-(5-{[2-(3,5-bis-trifluoromethyl-phenyl)-2-methyl-propionyl]-methyl-amino}-4-o-tolyl-pyridin-2-yl)-carbamic acid benzyl ester in 13 ml methanol and 1 ml N,N-dimethylformamide was added 40 mg 10% palladium on activated charcoal and the mixture was hydrogenated (room temperature, 1 bar) for 1 h. Filtration of the catalyst and evaporation of the filtrate afforded 795 mg (quantitative) of the title compound as a yellow oil.

MS m/e (%): 586 (M+H$^+$, 100).

e) N-(6-Amino-4-o-tolyl-pyridin-3-yl)-2-(3,5-bis-trifluoromethyl-phenyl)-N-methyl-isobutyramide A solution of 750 mg (1.28 mmol) N-(6-benzylamino-4-o-tolyl-pyridin-3-yl)-2-(3,5-bis-trifluoromethyl-phenyl)-N-methyl-isobutyramide in 25 ml of a 5 N solution of hydrochloric acid in ethanol was evaporated to dryness and the residue was dissolved in 30 ml methanol and hydrogenated in the presence of 60 mg 10% palladium on activated charcoal (room temperature, 10 bar) for 20 h. After filtration of the catalyst and evaporation of the solvent the residue was dissolved in 30 ml ethyl acetate, washed twice with saturated aqueous sodium hydrogencarbonate solution and dried (magnesium sulfate). Evaporation of the solution afforded 514 mg (81%) of the title compound as light brown crystals.

MS m/e (%): 496 (M+H$^+$, 100).

f) Acetic acid (5-{[2-(3,5-bis-trifluoromethyl-phenyl)-2-methyl-propionyl]-methyl-amino}-4-o-tolyl-pyridin-2-ylcarbamoyl)-methyl ester To a solution of 100 mg (0.20 mmol) N-(6-amino-4-o-tolyl-pyridin-3-yl)-2-(3,5-bis-trifluoromethyl-phenyl)-N-methyl-isobutyramide in 3 ml dichloromethane were added 27 mg (0.21 mmol) N-ethyldiisopropylamine and 30 mg (0.21 mmol) acetoxy acetyl chloride. After stirring overnight, the solvent was evaporated and the residue was purified by flash-chromatography to give 62 mg (52%) of the title compound as white solid.

MS m/e (%): 618 (M+Na$^+$, 19), 596 (M+H$^+$, 100).

EXAMPLE 13

2-(3,5-Bis-trifluoromethyl-phenyl)-N-[6-(2-hydroxy-acetylamino)-4-o-tolyl-pyridin-3-yl]-N-methyl-isobutyramide To a solution of 30 mg (0.05 mmol) acetic acid (5-{[2-(3,5-bis-trifluoromethyl-phenyl)-2-methyl-propionyl]-methyl-amino}-4-o-tolyl-pyridin-2-ylcarbamoyl)-methyl ester in 2 ml tetrahydrofuran were added 2 ml 1 N sodium hydroxide solution at room temperature. After stirring for 15 min, ethyl acetate was added, the aqueous phase was separated and the organic layer was dried (sodium sulfate). After evaporation the residue was purified by flash-chromatography to give 15 mg (54%) of the title compound as white solid.

MS m/e (%): 576 (M+Na$^+$, 19), 554 (M+H$^+$, 100).

EXAMPLE 14

2-(3,5-Bis-trifluoromethyl-phenyl)-N-[6-(hydroxyacetyl-methyl-amino)-4-o-tolyl-pyridin-3-yl]-N-methyl-isobutyramide To a solution of 70 mg (0.12 mmol) acetic acid (5-{[2-(3,5-bis-trifluoromethyl-phenyl)-2-methyl-propionyl]-methyl-amino}-4-o-tolyl-pyridin-2-ylcarbamoyl)-methyl ester in 4 ml tetrahydrofuran at room temperature under argon were added dropwise 0.13 ml (0.12 mmol) of a 1 M solution of potassium hexamethyldisilazide in tetrahydrofuran. Stirring was continued for 1 h at room temperature and 17 mg (0.12 mmol) methyl iodide were added. After stirring overnight, saturated ammonium chloride solution was added and the aqueous layer was extracted with diethyl ether. The diethyl ether layer was dried with sodium sulfate, evaporated, and the residue was purified by flash-chromatography to give 12 mg (18%) of the title compound as a white solid.

MS m/e (%): 590 (M+Na$^+$, 31), 568 (M+H$^+$, 100).

EXAMPLE 15

2-(3,5-Bis-trifluoromethyl-phenyl)-N-[6-(2,5-dioxo-pyrrolidin-1-yl)-4-o-tolyl-pyridin-3-yl]-N-methyl-isobutyramide To a solution of 100 mg (0.20 mmol) N-(6-amino-4-o-tolyl-pyridin-3-yl)-2-(3,5-bis-trifluoromethyl-phenyl)-N-methyl-isobutyramide in 3 ml pyridine were added 54 mg (0.50 mmol) trimethylchlorosilane at room temperature. After stirring for 15 min, this mixture was added slowly under stirring to 155 mg (1.0 mmol) succinyl chloride and stirring was continued overnight. The solvent was removed in vacuo and the residue was purified by flash-chromatography to give 29 mg (25%) of the title compound as white solid.

MS m/e (%): 600 (M+Na$^+$, 16), 578 (M+H$^+$, 100).

EXAMPLE 16

Cyclopropanecarboxylic acid (5-{[2-(3,5-bis-trifluoromethyl-phenyl)-2-methyl-propionyl]-methyl-amino}-4-o-tolyl-pyridin-2-yl)-cyclopropanecarbonyl-amide To a solution of 100 mg (0.20 mmol) N-(6-amino-4-o-tolyl-pyridin-3-yl)-2-(3,5-bis-trifluoromethyl-phenyl)-N-methyl-isobutramide in 3 ml dichloromethane were added 29 mg (0.21 mmol) N-ethyldiisopropylamine and 46 mg (0.44 mmol) cyclopropanecarboxylic acid chloride at 0° C. After stirring overnight at room temperature, the solvent was removed in vacuo and the residue was purified by flash-chromatography to give 80 mg (63%) of the title compound as white solid.

MS m/e (%): 654 (M+Na$^+$, 30), 632 (M+H$^+$, 100).

EXAMPLE 17

4-o-Tolyl-[2,3']bipyridinyl-5-carboxylic acid (3,5-bis-trifluoromethyl-benzyl)-methyl-amide The title compound was obtained as a white solid in comparable yield according to the procedure described above for the preparation of 4-o-tolyl-[2,4']bipyridinyl-5-carboxylic acid (3,5-bis-trifluoromethyl-benzyl)-methyl-amide using 3-pyridylboronic acid instead of 4-pyridylboronic acid.

MS m/e (%): 530 (M+H$^+$, 100).

EXAMPLE 18

N-(3,5-Bis-trifluoromethyl-benzyl)-6-(2-methoxy-phenyl)-N-methyl-4-o-tolyl-nicotinamide The title compound was obtained as a light brown solid in 99% yield according to the procedure described above for the preparation of 4-o-tolyl-[2,4']bipyridinyl-5-carboxylic acid (3,5-bis-trifluoromethyl-benzyl)-methyl-amide using 2-methoxyphenylboronic acid instead of 4-pyridylboronic acid.

MS m/e (%): 559 (M+H$^+$, 100).

EXAMPLE 19

N-(3,5-Bis-trifluoromethyl-benzyl)-6-(3-methoxy-phenyl)-N-methyl-4-o-tolyl-nicotinamide The title compound was obtained as a light yellow viscous oil in 81% yield according to the procedure described above for the preparation of 4-o-tolyl-[2,4']bipyridinyl-5-carboxylic acid (3,5-bis-trifluoromethyl-benzyl)-methyl-amide using 3-methoxyphenylboronic acid instead of 4-pyridylboronic acid.

MS m/e (%): 559 (M+H$^+$, 100).

EXAMPLE 20

N-(3,5-Bis-trifluoromethyl-benzyl)-6-(4-methoxy-phenyl)-N-methyl-4-o-tolyl-nicotinamide The title compound was obtained as a light yellow solid in 90% yield according to the procedure described above for the preparation of 4-o-tolyl-[2,4']bipyridinyl-5-carboxylic acid (3,5-bis-trifluoromethyl-benzyl)-methyl-amide using 4-methoxyphenylboronic acid instead of 4-pyridylboronic acid.

MS m/e (%): 559 (M+H$^+$, 100).

EXAMPLE 21

N-(3,5-Bis-trifluoromethyl-benzyl)-6-(2-hydroxy-phenyl)-N-methyl-4-o-tolyl-nicotinamide To a solution of 80 mg (0.14 mmol) N-(3,5-bis-trifluoromethyl-benzyl)-6-(2-methoxy-phenyl)-N-methyl-4-o-tolyl-nicotinamide in 1.5 ml dichloromethane 0.17 ml of a 1M solution of boron tribromide in dichloromethane (0.17 mmol) were added dropwise at 0° C. The temperature was allowed to warm to room temperature over night. Water and a 1M aqueous solution of hydrochloric acid were added. After 5 min the mixture was neutralized by addition of 1M aqueous sodium hydroxide solution and extracted with dichloromethane. The organic layer was dried with sodium sulfate and concentrated. Column chromatography afforded 67 mg (86%) of the title compound as a white solid.

MS m/e (%):545 (M+H$^+$, 100).

EXAMPLE 22

N-(3,5-Bis-trifluoromethyl-benzyl)-6-(3-hydroxy-phenyl)-N-methyl-4-o-tolyl-nicotinamide The title compound was obtained as a white solid in comparable yield according to the procedure described above for the preparation of N-(3,5-bis-trifluoromethyl-benzyl)-6-(2-hydroxy-phenyl)-N-methyl-4-o-tolyl-nicotinamide using N-(3,5-bis-trifluoromethyl-benzyl)-6-(3-methoxy-phenyl)-N-methyl-4-o-tolyl-nicotinamide instead of N-(3,5-bis-trifluoromethyl-benzyl)-6-(2-methoxy-phenyl)-N-methyl-4-o-tolyl-nicotinamide.

MS m/e (%):545 (M+H$^+$, 100).

EXAMPLE 23

N-(3,5-Bis-trifluoromethyl-benzyl)-6-(4-hydroxy-phenyl)-N-methyl-4-o-tolyl-nicotinamide To a solution of 80 mg (0.14 mmol) N-(3,5-bis-trifluoromethyl-benzyl)-6-(2-methoxy-phenyl)-N-methyl-4-o-tolyl-nicotinamide in 1.5 ml dichloromethane 0.43 ml of a 1M solution of boron tribromide in dichloromethane (0.43 mmol) were added dropwise at 0° C. The cooling bath was removed and the mixture was stirred at 35° C. over night. Water and a 1M aqueous solution of hydrochloric acid were added. After 5 min the mixture was neutralized by addition of 1M aqueous sodium hydroxide solution and extracted with dichloromethane. The organic layer was dried with sodium sulfate and concentrated. Column chromatography afforded 63 mg (81%) of the title compound as a white solid.

MS m/e (%):545 (M+H$^+$, 100).

EXAMPLE 24

2-(3,5-Bis-trifluoromethyl-phenyl)-N-[6-chloro-4-(2-chloro-phenyl)-pyridin-3-yl]-N-methyl-isobutyramide a) 5-Bromo-2-chloro-pyridine To a solution of 15.0 g (75.8 mmol) 5-bromo-2-methoxypyridine in 90 ml dry N,N-dimethylformamide 21.2 ml (227 mol) phosphorus oxychloride were slowly added at 0° C. After completed addition the reaction mixture was heated to 110° C. over a period of 30 min. At this temperature the reaction started to be exothermic. The heating bath was partly removed such that the internal temperature did not exceed 120° C. When the internal temperature started to drop heating was resumed, and the reaction mixture was kept at an internal temperature of 100–110° C. for 18 h. After cooling to room temperature the reflux condenser was exchanged by a claisen condenser, and the title compound was gained as a mixture with N,N-dimethylformamide by vacuum distillation at 40–50° C. (1–10 mbar). The distillate was diluted with cyclohexane and washed with two portions of water. The combined aqueous layers were extracted with cyclohexane. The combined organic extracts were dried with sodium sulfate and concentrated to give 11.0 g (76%) of the title compound as a white solid.

MS m/e, isotope cluster (%): 191 (M$^+$, 75), 193 (100), 195 (24).

b) 5-Bromo-2-chloro-4-iodo-pyridine

To a solution of 12 ml (83 mmol) diisopropylamine in 80 ml dry tetrahydrofuran 52 ml of a solution of n-butyllithium in hexanes (1.6 M, 83 mmol) was added at −78° C. over a period of 15 min under argon. The mixture was stirred at −78° C. for 10 min. A solution of 15.2 g (79.0 mmol) 5-bromo-2-chloro-pyridine in 160 ml dry tetrahydrofuran was added at a rate such that the internal temperature did not exceed −70° C. After completed addition the reaction mixture was stirred at −78° C. for 5 h. A solution of 24 g (95 mmol) iodine in 160 ml dry tetrahydrofuran was added at a rate such that the internal temperature did not exceed −70° C. The reaction mixture was stirred for another 30 min at −78° C. The reaction mixture was allowed to warm to −10° C. and treated with 120 ml of an aqueous solution of sodium thiosulfate (1 M, 120 mmol). The layers were separated and the aqueous layer was extracted with two portions of ethyl acetate. The combined organic layers were washed twice with saturated ammonium hydroxide solution, dried with sodium sulfate and concentrated. The residue was dissolved in hot heptane and allowed to stand over night. Filtration of the precipitate and drying in vacuo gave 19.3 g (77%) of the title compound as a light brown solid.

MS m/e (%): 318 (M$^+$, 100).

c) 5-Bromo-2-chloro-4-(2-chloro-phenyl)-pyridine

A mixture of 10.8 g (33.9 mmol) 5-bromo-2-chloro-4-iodo-pyridine, 5.84 g (37.3 mmol) 2-chlorophenylboronic acid, 200 ml dimethoxyethane and 50 ml of a 2 M aqueous solution of sodium carbonate was deoxygenated by three freeze-thaw cycles. After addition of 381 mg (1.70 mmol) palladium(II) acetate and 917 mg (3.39 mmol) triphenylphosphine the reaction mixture was stirred at 90° C. for 4 h. Cooling to room temperature was followed by dilution with water and extraction with two portions of tert-butyl methyl ether. The combined organic extracts were washed with brine, dried with magnesium sulfate and concentrated. Column chromatography afforded 7.74 g (75%) of the title compound as a white solid.

MS m/e, isotope cluster (%): 301 (M$^+$, 60), 303 (100), 305 (45).

d) 6-Chloro-4-(2-chloro-phenyl)-nicotinic acid ethyl ester

To a solution of 2.00 g (6.60 mmol) 5-bromo-2-chloro-4-(2-chloro-phenyl)-pyridine in 66 ml tetrahydrofuran 4.3 ml of a solution of n-butyllithium in hexanes (1.6 M, 6.9 mmol) were added dropwise at −100° C. under argon. Thin layer chromatography showed complete bromine-lithium exchange after 5 min. After addition of 0.71 ml (7.3 mmol) ethyl chloroformate the reaction mixture was allowed to slowly warm to −78° C. and stirred at that temperature for 1 h. The reaction mixture was allowed to warm to room temperature over night. Quenching with a small amount of water was followed by dilution with tert-butyl methyl ether and washing with water and brine. The organic layer was dried with sodium sulfate and concentrated. Column chromatography afforded 1.66 g (85%) of the title compound as a light yellow solid.

MS m/e (%): 295 (M$^+$, 97), 250 ([M-OEt]$^+$, 100).

e) 6-Chloro-4-(2-chloro-phenyl)-nicotinic acid

A mixture of 3.20 g (10.8 mmol) 6-chloro-4-(2-chloro-phenyl)-nicotinic acid ethyl ester, 50 ml dioxane and 50 ml of a 2 M aqueous sodium hydroxide solution was stirred at room temperature for 17 h. Dilution with water was followed by washing with two portions of tert-butyl methyl ether. The combined organic layers were extracted with 1 M aqueous sodium hydroxide solution. The combined aqueous layers were acidified to pH 2 with 2 M aqueous hydrochloric acid solution and extracted with four portions of tert-butyl methyl ether. The combined organic extracts were dried with sodium sulfate and concentrated to give 2.90 g (100%) of the title compound as an off-white solid.

MS(ISN) m/e (%): 266 ([M-(H$^+$)]$^-$, 100).

f) [6-Chloro-4-(2-chloro-phenyl)-pyridin-3-yl]-carbamic acid tert-butyl ester

A mixture of 650 mg (2.42 mmol) 6-chloro-4-(2-chloro-phenyl)-nicotinic acid, 0.54 ml (2.42 mmol) diphenylphosphoryl azide, 0.34 ml (2.42 mmol) triethylamine and 8 ml tert-butanol was heated at reflux for 1 h. Cooling to room temperature was followed by evaporation of the solvent in vacuo. The residue was dissolved in ethyl acetate and washed with saturated aqueous ammonium chloride solution, saturated aqueous sodium bicarbonate solution and brine. The organic layer was dried with sodium sulfate and concentrated. Column chromatography gave 695 mg (85%) of the title compound as a white solid.

MS m/e (%): 339 (M+H$^+$, 76).

g) [6-Chloro-4-(2-chloro-phenyl)-pyridin-3-yl]-methyl-carbamic acid tert-butyl ester To a solution of 1.21 g (3.57 mmol) [6-chloro-4-(2-chloro-phenyl)-pyridin-3-yl]-carbamic acid tert-butyl ester in 35 ml N,N-dimethylformamide 0.18 g (3.7 mmol) sodium hydride (55% dispersion in mineral oil) were added at room temperature. After 30 min 0.25 ml (3.9 mmol) methyl iodide were added and the reaction mixture was stirred for 1 h. Quenching was followed by extraction with tert-butyl methyl ether. The organic layer was washed with two portions of water, and the combined aqueous layers were extracted with two portions of tert-butyl methyl ether. The combined organic layers were dried with sodium sulfate and concentrated to give 1.26 g (100%) of the title compound as a light yellow amorphous mass.

MS m/e (%): 353 (M+H$^+$, 92).

h) [6-Chloro-4-(2-chloro-phenyl)-pyridin-3-yl]-methyl-amine

A solution of 1.26 g (3.55 mmol) [6-chloro-4-(2-chloro-phenyl)-pyridin-3-yl]-methyl-carbamic acid tert-butyl ester and 3.34 ml (42.8 mmol) trifluoroacetic acid in 11 ml dichloromethane was stirred at room temperature for 2 h. Addition of 2 M aqueous sodium carbonate solution was followed by extraction with two portions of dichloromethane. The combined organic layers were dried with sodium sulfate and concentrated to give 0.89 g (99%) of the title compound as an off-white solid.

MS m/e (%): 253 (M+H$^+$, 100).

i) 2-(3,5-Bis-trifluoromethyl-phenyl)-N-[6-chloro-4-(2-chloro-phenyl)-pyridin-3-yl]-N-methyl-isobutyramide To a solution of 180 mg (0.711 mmol) [6-chloro-4-(2-chloro-phenyl)-pyridin-3-yl]-methyl-amine in 7 ml dry tetrahydrofuran 0.86 ml of a 0.91 M solution (0.78 mmol) of potassium hexamethyldisilazide in tetrahydrofuran was added at room temperature under an atmosphere of argon. After 45 min 295 mg (0.924 mmol) 2-(3,5-bistrifluoromethyl-phenyl)-2-methyl-propionyl chloride were added. The reaction mixture was stirred at room temperature for 3 h. Quenching with water was followed by dilution with tert-butyl methyl ether and washing with 2 M aqueous sodium carbonate solution and brine. The combined aqueous layers were extracted with two portions of tert-butyl methyl ether. The combined organic extracts were dried with sodium sulfate and concentrated. Flash chromatography gave 254 mg (67%) of the title compound as a light yellow solid.

MS m/e (%): 535 (M+H$^+$, 100).

EXAMPLE 25

2-(3,5-Bis-trifluoromethyl-phenyl)-N-[4-(2-chloro-phenyl)-6-iodo-pyridin-3-yl]-N-methyl-isobutyramide A mixture of 250 mg (0.467 mmol) 2-(3,5-bis-trifluoromethyl-phenyl)-N-[6-chloro-4-(2-chloro-phenyl)-pyridin-3-yl]-N-methyl-isobutyramide (Example 24), 250 mg (1.64 mmol) sodium iodide and 0.12 ml (0.99 mmol) hydroiodic acid (57% in water) in 5 ml 3-methyl-2-butanone was heated at 80° C. for 5 h in a sealed tube. After cooling to room temperature the mixture was diluted with tert-butyl methyl ether and treated with saturated aqueous sodium bicarbonate solution. The layers were separated, the organic layer washed with water, dried with magnesium sulfate and concentrated. Flash column chromatography gave 218 mg (48%) of the title compound as a light brown solid.

MS m/e (%): 627 (M+H$^+$, 100).

EXAMPLE 26

2-(3,5-Bis-trifluoromethyl-phenyl)-N-(6-chloro-4-o-tolyl-pyridin-3-yl)-N-methyl-isobutyramide The title compound was obtained as a light yellow solid in comparable yields according to the procedures described above for the preparation of 2-(3,5-bis-trifluoromethyl-phenyl)-N-[6-chloro-4-(2-chloro-phenyl)-pyridin-3-yl]-N-methyl-isobutyramide (Example 24) using o-tolylboronic acid instead of 2-chlorophenylboronic acid in step c).

MS m/e (%): 514 (M$^+$, 5).

EXAMPLE 27

2-(3,5-Bis-trifluoromethyl-phenyl)-N-(6-iodo-4-o-tolyl-pyridin-3-yl)-N-methyl-isobutyramide The title compound was obtained as a light yellow solid in 58% yield according to the procedure described above for the preparation of 2-(3,5-bis-trifluoromethyl-phenyl)-N-[4-(2-chloro-phenyl)-6-iodo-pyridin-3-yl]-N-methyl-isobutyramide (Example 25) using 2-(3,5-bis-trifluoromethyl-phenyl)-N-(6-chloro-4-o-tolyl-pyridin-3-yl)-N-methyl-isobutyramide (Example 26) instead of 2-(3,5-bis-trifluoromethyl-phenyl)-N-[6-chloro-4-(2-chloro-phenyl)-pyridin-3-yl]-N-methyl-isobutyramide.

MS m/e (%): 606 (M$^+$, 13).

EXAMPLE 28

2-(3,5-Bis-trifluoromethyl-phenyl)-N-[6-chloro-4-(4-fluoro-2-methyl-phenyl)-pyridin-3-yl]-N-methyl-isobutyramide The title compound is prepared according to the procedures described above for the preparation of 2-(3,5-bis-trifluoromethyl-phenyl)-N-[6-chloro-4-(2-chloro-phenyl)-pyridin-3-yl]-N-methyl-isobutyramide (Example 24) using (4-fluoro-2-methylphenyl)boronic acid instead of 2-chlorophenylboronic acid in step c).

EXAMPLE 29

2-(3,5-Bis-trifluoromethyl-phenyl)-N-[4-(4-fluoro-2-methyl-phenyl)-6-iodo-pyridin-3-yl]-N-methyl-isobutyramide The title compound is prepared according to the procedure described above for the preparation of 2-(3,5-bis-trifluoromethyl-phenyl)-N-[4-(2-chloro-phenyl)-6-iodo-pyridin-3-yl]-N-methyl-isobutyramide (Example 25) using 2-(3,5-bis-trifluoromethyl-phenyl)-N-[6-chloro-4-(4-fluoro-2-methyl-phenyl)-pyridin-3-yl]-N-methyl-isobutyramide instead of 2-(3,5-bis-trifluoromethyl-phenyl)-N-[6-chloro-4-(2-chloro-phenyl)-pyridin-3-yl]-N-methyl-isobutyramide.

EXAMPLE 30

2-(3,5-Bis-trifluoromethyl-phenyl)-N-[6-chloro-4-(4-fluoro-phenyl)-pyridin-3-yl]-N-methyl-isobutyramide The title compound was obtained as a light brown solid in comparable yields according to the procedures described above for the preparation of 2-(3,5-bis-trifluoromethyl-phenyl)-N-[6-chloro-4-(2-chloro-phenyl)-pyridin-3-yl]-N-methyl-isobutyramide (Example 24) using 4-fluorophenylboronic acid instead of 2-chlorophenylboronic acid in step c).

MS m/e (%): 519 (M+H$^+$, 100).

EXAMPLE 31

2-(3,5-Bis-trifluoromethyl-phenyl)-N-[4-(4-fluoro-phenyl)-6-iodo-pyridin-3-yl]-N-methyl-isobutyramide The title compound is prepared according to the procedure described above for the preparation of 2-(3,5-bis-trifluoromethyl-phenyl)-N-[4-(2-chloro-phenyl)-6-iodo-pyridin-3-yl]-N-methyl-isobutyramide (Example 25) using 2-(3,5-bis-trifluoromethyl-phenyl)-N-[6-chloro-4-(4-fluoro-phenyl)-pyridin-3-yl]-N-methyl-isobutyramide (Example 30) instead of 2-(3,5-bis-trifluoromethyl-phenyl)-N-[6-chloro-4-(2-chloro-phenyl)-pyridin-3-yl]-N-methyl-isobutyramide.

EXAMPLE 32

N-(3,5-Bis-trifluoromethyl-benzyl)-6-chloro-4-(2-chloro-phenyl)-N-methyl-nicotinamide To a solution of 300 mg (1.12 mmol) 6-chloro-4-(2-chloro-phenyl)-nicotinic acid (Example 24, step e)) in 12 ml dichloromethane 0.15 ml (1.7 mmol) oxalyl chloride and one drop of N,N-dimethylformamide were added at 0° C. After completed addition the reaction mixture was allowed to warm to room temperature and stirred for 1 h. The reaction mixture was concentrated in vactio. The residue was redissolved in 6 ml dichloromethane and added dropwise to a solution of 432 mg (1.68 mmol) (3,5-bis-trifluoromethyl-benzyl)-methyl-amine, 0.39 ml (2.2 mmol) N-ethyldiisopropylamine and 7 mg (0.06 mmol) 4-(N,N-dimethylamino)pyridine in 6 ml dichloromethane at 0° C. After completed addition the reaction mixture was allowed to warm to room temperature and stirred over night. The reaction mixture was diluted with dichloromethane and washed with two portions of 1 M aqueous hydrochloric acid solution. The combined aqueous layers were extracted with dichloromethane. The combined organic extracts were washed with two portions of 1 M aqueous sodium hydroxide solution. The combined basic aqueous layers were extracted with dichloromethane. The combined organic extracts were dried with sodium sulfate and concentrated. Column chromatography afforded 475 mg (84%) of the title compound as a light yellow amorphous mass.

MS m/e (%): 507 (M+H$^+$, 100).

EXAMPLE 33

N-(3,5-Bis-trifluoromethyl-benzyl)-4-(2-chloro-phenyl)-6-iodo-N-methyl-nicotinamide The title compound was obtained as a light brown amorphous mass in 21% yield according to the procedure described above for the preparation of N-(3,5-bis-trifluoromethyl-benzyl)-6-iodo-N-methyl-4-o-tolyl-nicotinamide (Example 4) using N-(3,5-bis-trifluoromethyl-benzyl)-6-chloro-4-(2-chloro-phenyl)-N-methyl-nicotinamide (Example 32) instead of N-(3,5-bis-trifluoromethyl-benzyl)-6-chloro-N-methyl-4-o-tolyl-nicotinamide.

MS m/e (%): 599 (M+H$^+$, 100).

EXAMPLE 34

N -(3,5-Bis-trifluoromethyl-benzyl)-6-chloro-4-(4-fluoro-2-methyl-phenyl)-N-methyl-nicotinamide a) 6-Chloro-4-(4-fluoro-2-methyl-phenyl)-nicotinic acid The title compound was obtained as an off-white solid in comparable yields according to the procedures described above for the preparation of 6-chloro-4-(2-chloro-phenyl)-nicotinic acid (Example 24, step e)) using (4-fluoro-2-methylphenyl)boronic acid instead of 2-chlorophenylboronic acid in step c).

MS(ISN) m/e (%): 264 ([M-(H$^+$)]$^-$, 100).

b) N-(3,5-Bis-trifluoromethyl-benzyl)-6-chloro-4-(4-fluoro-2-methyl-phenyl)-N-methyl-nicotinamide The title compound was obtained as a white solid in 92% yield according to the procedure described above for the preparation of N-(3,5-bis-trifluoromethyl-benzyl)-6-chloro-4-(2-chloro-phenyl)-N-methyl-nicotinamide (Example 32) using 6-chloro-4-(4-fluoro-2-methyl-phenyl)-nicotinic acid instead of 6-chloro-4-(2-chloro-phenyl)-nicotinic acid.

MS m/e (%): 505 (M+H$^+$, 100).

EXAMPLE 35

N-(3,5-Bis-trifluoromethyl-benzyl)-4-(4-fluoro-2-methyl-phenyl)-6-iodo-N-methyl-nicotinamide The title compound was obtained as a yellow viscous oil in 50% yield according to the procedure described above for the preparation of N-(3,5-bis-trifluoromethyl-benzyl)-6-iodo-N-methyl-4-o-tolyl-nicotinamide (Example 4) using N-(3,5-bis-trifluoromethyl-benzyl)-6-chloro-4-(4-fluoro-2-methyl-phenyl)-N-methyl-nicotinamide (Example 34) instead of N-(3,5-bis-trifluoromethyl-benzyl)-6-chloro-N-methyl-4-o-tolyl-nicotinamide.

MS m/e (%): 597 (M+H$^+$, 100).

EXAMPLE 36

N-(3,5-Bis-trifluoromethyl-benzyl)-6-chloro-4-(4-fluoro-phenyl)-N-methyl-nicotinamide a) 6-Chloro-4-(4-fluoro-phenyl)-nicotinic acid The title compound was obtained as a light brown solid in comparable yields according to the procedures described above for the preparation of 6-chloro-4-(2-chloro-phenyl)-nicotinic acid (Example 24, step e)) using 4-fluorophenylboronic acid instead of 2-chlorophenylboronic acid in step c).

MS(ISN) m/e (%): 250 ([M-(H$^+$)]$^-$, 100).

b) N-(3,5-Bis-trifluoromethyl-benzyl)-6-chloro-4-(4-fluoro-phenyl)-N-methyl-nicotinamide The title compound was obtained as a light yellow solid in 98% yield according to the procedure described above for the preparation of N-(3,5-bis-trifluoromethyl-benzyl)-6-chloro-4-(2-chloro-phenyl)-N-methyl-nicotinamide (Example 32) using 6-chloro-4-(4-fluoro-phenyl)-nicotinic acid instead of 6-chloro-4-(2-chloro-phenyl)-nicotinic acid.

MS m/e (%): 491 (M+H$^+$, 100).

EXAMPLE 37

N-(3,5-Bis-trifluoromethyl-benzyl)-4-(4-fluoro-phenyl)-6-iodo-N-methyl-nicotinamide The title compound is prepared according to the procedure described above for the preparation of N-(3,5-bis-trifluoromethyl-benzyl)-6-iodo-N-methyl-4-o-tolyl-nicotinamide (Example 4) using N-(3,5-bis-trifluoromethyl-benzyl)-6-chloro-4-(4-fluoro-phenyl)-N-methyl-nicotinamide (Example 36) instead of N-(3,5-bis-trifluoromethyl-benzyl)-6-chloro-N-methyl-4-o-tolyl-nicotinamide.

EXAMPLE 38

6-(5-Acetyl-thiophen-2-yl)-N-(3,5-bis-trifluoromethyl-benzyl)-N-methyl-4-o-tolyl-nicotinamide The title compound was obtained as a white solid in 49% yield according to the procedure described above for the preparation of 4-o-tolyl-[2,4']bipyridinyl-5-carboxylic acid (3,5-bis-trifluoromethyl-benzyl)-methyl-amide (Example 5) using 5-acetyl-2-thiopheneboronic acid instead of 4-pyridylboronic acid.

MS m/e (%): 577 (M+H$^+$, 100).

EXAMPLE 39

(RS)-N-(3,5-Bis-trifluoromethyl-benzyl)-6-[5-(1-hydroxy-ethyl)-thiophen-2-yl]-N-methyl-4-o-tolyl-nicotinamide A mixture of 50 mg (0.087 mmol) 6-(5-acetyl-thiophen-2-yl)-N-(3,5-bis-trifluoromethyl-benzyl)-N-methyl-4-o-tolyl-nicotinamide (Example 38), 7 mg (0.2 mmol) sodium borohydride in 1 ml ethanol and a small amount of tetrahydrofuran was stirred at room temperature for 2 h. The reaction was quenched by addition of water, followed by 1 N aqueous hydrochloric acid solution. The mixture was basified with sodium carbonate and extracted with 3 portions of ethyl acetate. The combined organic extracts were dried with sodium sulfate, filtered and concentrated to give 48 mg (96%) of the title compound as a slightly yellow solid.

MS m/e (%): 579 (M+H$^+$, 100).

EXAMPLE 40

N-(3,5-Bis-trifluoromethyl-benzyl)-6-(3,5-dimethyl-isoxazol-4-yl)-N-methyl-4-o-tolyl-nicotinamide The title compound was obtained as a light brown solid in 83% yield according to the procedure described above for the preparation of 4-o-tolyl-[2,4']bipyridinyl-5-carboxylic acid (3,5-bis-trifluoromethyl-benzyl)-methyl-amide (Example 5) using 3,5-dimethylisoxazole-4-boronic acid instead of 4-pyridylboronic acid.

MS m/e (%): 548 (M+H$^+$, 100).

EXAMPLE 41

5-[(3,5-Bis-trifluoromethyl-benzyl)-methyl-carbamoyl]-4-o-tolyl-3',6'-dihydro-2'H-[2,4'] bipyridinyl-1'-carboxylic acid tert-butyl ester The title compound was obtained as a light orange solid in 61% yield according to the procedure described above for the preparation of 4-o-tolyl-[2,4']bipyridinyl-5-carboxylic acid (3,5-bis-trifluoromethyl-benzyl)-methyl-amide (Example 5) using 4-(4,4,5,5-tetramethyl-[1,3,2] dioxaborolan-2-yl)-3,6-dihydro-2H-pyridine-1-carboxylic acid tert-butyl ester instead of 4-pyridylboronic acid.

MS m/e (%): 634 (M+H$^+$, 100).

EXAMPLE 42

4-o-Tolyl-1',2',3',6'-tetrahydro-[2,4']bipyridinyl-5-carboxylic acid (3,5-bis-trifluoromethyl-benzyl)-methyl-amide A solution of 258 mg (0.407 mmol) 5-[(3,5-bis-trifluoromethyl-benzyl)-methyl-carbamoyl]-4-o-tolyl-3',6'-dihydro-2'H-[2,4']bipyridinyl-1'-carboxylic acid tert-butyl ester (Example 41) and 0.26 ml (3.2 mmol) trifluoroacetic acid in 2 ml dichloromethane was heated at reflux for 4 h. After cooling to room temperature the mixture was diluted with dichloromethane and washed with 1N aqueous sodium hydroxide solution. The aqueous layer was extracted with three portions of dichloromethane. The combined organic extracts were dried over sodium sulfate and concentrated. Column chromatography afforded 135 mg (62%) of the title compound as a light brown solid.

MS m/e (%): 534 (M+H$^+$, 100).

EXAMPLE 43

1'-Cyclopropylmethyl-4-o-tolyl-1',2',3',6'-tetrahydro-[2,4']bipyridinyl-5-carboxylic acid (3,5-bis-trifluoromethyl-benzyl)-methyl-amide A mixture of 60 mg (0.11 mmol) 4-o-tolyl-1',2',3', 6'-tetrahydro-[2,4']bipyridinyl-5-carboxylic acid (3,5-bis-trifluoromethyl-benzyl)-methyl-amide (Example 42), 0.011 ml (0.11 mmol) (bromomethyl)cyclopropane and 19 mg (0.14 mmol) potassium carbonate in 1.5 ml acetonitrile was stirred at room temperature for 15 h. The mixture was diluted with ethyl acetate and washed with water. The aqueous layer was extracted with three portions of ethyl acetate. The combined organic extracts were dried over sodium sulfate and concentrated. Column chromatography afforded 28 mg (42%) of the title compound as a light brown solid.

MS m/e (%): 588 (M+H$^+$, 100).

EXAMPLE 44

4-{5-[(3,5-Bis-trifluoromethyl-benzyl)-methyl-carbamoyl]-4-o-tolyl-pyridin-2-yl}-benzoic acid methyl ester A mixture of 200 mg (0.346 mmol) N-(3,5-bis-trifluoromethyl-benzyl)-6-iodo-N-methyl-4-o-tolyl-nicotinamide (Example 4), 95 mg (0.52 mmol) 4-methoxycarbonylphenylboronic acid and 155 mg (0.692 mmol) potassium phosphate in 4 ml dioxane was deoxygenated by three freeze-thaw cycles. After addition of 9.5 mg (0.010 mmol) tris(dibenzylideneacetone)dipalladium(0) and 0.0025 ml (0.02 mmol) trimethyl phosphite the reaction mixture was stirred at 95° C. for 5 h. Cooling to room temperature was followed by dilution with tert-butyl methyl ether, filtration over Decalite and evaporation of the solvent in vacuo. Column chromatography afforded 50 mg (25%) of the title compound as a light brown solid.

MS m/e (%): 587 (M+H$^+$, 100).

EXAMPLE 45

N-(3,5-Bis-trifluoromethyl-benzyl)-6-(4-hydroxymethyl-phenyl)-N-methyl-4-o-tolyl-nicotinamide The title compound was obtained as a light yellow solid in 41% yield according to the procedure described above for the preparation of N-(3,5-bis-trifluoromethyl-benzyl)-6-hydroxymethyl-N-methyl-4-o-tolyl-nicotinamide (Example 7) using 4-{5-[(3,5-bis-trifluoromethyl-benzyl)-methyl-carbamoyl]-4-o-tolyl-pyridin-2-yl}-benzoic acid methyl ester (Example 44) instead of 5-[(3,5-bis-trifluoromethyl-benzyl)-methyl-carbamoyl]-4-o-tolyl-pyridine-2-carboxylic acid methyl ester.

MS m/e (%): 559 (M+H$^+$, 100).

EXAMPLE 46

2'-Methyl-4-o-tolyl-[2,4']bipyridinyl-5-carboxylic acid (3,5-bis-trifluoromethyl-benzyl)-methyl-amide a) 4-Iodo-2-methyl-pyridine The title compound was obtained as a red-brown solid in 84% yield according to the procedure described above for the preparation of N-(3,5-bis-trifluoromethyl-benzyl)-6-iodo-N-methyl-4-o-tolyl-nicotinamide (Example 4) using 4-chloro-2-methyl-pyridine instead of N-(3,5-bis-trifluoromethyl-benzyl)-6-chloro-N-methyl-4-o-tolyl-nicotinamide.

MS m/e (%): 219 (M$^+$, 100).

b) 2'-Methyl-4-o-tolyl-[2,4']bipyridinyl-5-carboxylic acid (3,5-bis-trifluoromethyl-benzyl)-methyl-amide A mixture of 300 mg (1.37 mmol) 4-iodo-2-methyl-pyridine, 383 mg (1.51 mmol) bis(pinacolato)diboron and 403 mg (4.11 mmol) potassium acetate in 8.5 ml N,N-dimethylformamide was deoxygenated by three freeze-thaw cycles. After addition of 112 mg (0.137 mmol) dichloro(1, 1'-bis(diphenylphosphino)ferrocene)palladium(II) dichloromethane adduct the reaction mixture was stirred at 80° C. for 3 h. Cooling to room temperature was followed by addition of 4 ml of a 2 M aqueous solution of sodium carbonate, 396 mg (0.685 mmol) N-(3,5-bis-trifluoromethyl-benzyl)-6-iodo-N-methyl-4-o-tolyl-nicotinamide (Example 4) and 56 mg (0.068 mmol) dichloro (1,1'-bis(diphenylphosphino)ferrocene)palladium(II) dichloromethane adduct. The reaction mixture was reheated to 80° C. for 1.5 h. After cooling to room temperature the reaction mixture was diluted with aqueous sodium bicarbonate solution and extracted with three portions of ethyl acetate. The combined organic extracts were dried with sodium sulfate, filtered and concentrated. Drying in high vacuo at 50° C. and flash column chromatography gave 292 mg (78%) of the title compound as a light brown solid.

MS m/e (%): 544 (M+H$^+$, 100).

EXAMPLE 47

4-(2-Chloro-phenyl)-2-methyl-[2,4']bipyridinyl-5-carboxylic acid (3,5-bis-trifluoromethyl-benzyl)-methyl-amide The title compound was obtained as a light brown amorphous mass in 42% yield according to the procedure described above for the preparation of 2'-methyl-4-o-tolyl-[2,4']bipyridinyl-5-carboxylic acid (3,5-bis-trifluoromethyl-benzyl)-methyl-amide (Example 46) using N-(3,5-bis-trifluoromethyl-benzyl)-4-(2-chloro-phenyl)-6-iodo-N-methyl-nicotinamide (Example 33) instead of N-(3,5-bis-trifluoromethyl-benzyl)-6-iodo-N-methyl-4-o-tolyl-nicotinamide.

MS m/e (%): 564 (M+H$^+$, 100).

EXAMPLE 48

2-(3,5-Bis-trifluoromethyl-phenyl)-N-[4-(2-chloro-phenyl)-2'-methyl-[2,4']bipyridinyl-5-yl]-N-methyl-isobutyramide The title compound was obtained as a light brown solid in 31% yield according to the procedure described above for the preparation of 2'-methyl-4-o-tolyl-[2,4']bipyridinyl-5-carboxylic acid (3,5-bis-trifluoromethyl-benzyl)-methyl-amide (Example 46) using 2-(3,5-bis-trifluoromethyl-phenyl)-N-[4-(2-chloro-phenyl)-6-iodo-pyridin-3-yl]-N-methyl-isobutyramide (Example 25) instead of N-(3,5-bis-trifluoromethyl-benzyl)-6-iodo-N-methyl-4-o-tolyl-nicotinamide.

MS m/e (%): 592 (M+H$^+$, 100).

EXAMPLE 49

5-{[2-(3,5-Bis-trifluoromethyl-phenyl)-2-methyl-propionyl]-methyl-amino}-4-o-tolyl-3',6'-dihydro-2'H-[2,4']bipyridinyl-1'-carboxylic acid tert-butyl ester The title compound was obtained as an orange viscous oil in 64% yield according to the procedure described above for the preparation of 4-o-tolyl-[2,4']bipyridinyl-5-carboxylic acid (3,5-bis-trifluoromethyl-benzyl)-methyl-amide (Example 5) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-(4,4,5,5-tetramethyl-[1,3,2]dioxaborolan-2-yl)-3,6-dihydro-2H-pyridine-1-carboxylic acid tert-butyl ester instead of 4-pyridylboronic acid.

MS m/e (%): 662 (M+H$^+$, 100).

EXAMPLE 50

2-(3,5-Bis-trifluoromethyl-phenyl)-N-[6-(4-cyano-phenyl)-4-o-tolyl-pyridin-3-yl]-N-methyl-isobutyramide The title compound was obtained as a white solid in 67% yield according to the procedure described above for the preparation of 4-o-tolyl-[2,4']bipyridinyl-5-carboxylic acid (3,5-bis-trifluoromethyl-benzyl)-methyl-amide (Example 5) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-cyanophenylboronic acid instead of 4-pyridylboronic acid.

MS m/e (%): 582 (M+H$^+$, 100).

EXAMPLE 51

2-(3,5-Bis-trifluoromethyl-phenyl)-N-[6-(4-fluoro-phenyl)-4-o-tolyl-pyridin-3-yl]-N-methyl-isobutyramide The title compound was obtained as a light brown solid in 45% yield according to the procedure described above for the preparation of 4-o-tolyl-[2,4']bipyridinyl-5-carboxylic acid (3,5-bis-trifluoromethyl-benzyl)-methyl-amide (Example 5) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-fluorophenylboronic acid instead of 4-pyridylboronic acid.

MS m/e (%): 575 (M+H$^+$, 100).

EXAMPLE 52

2-(3,5-Bis-trifluoromethyl-phenyl)-N-[6-(3,4-difluoro-phenyl)-4-o-tolyl-pyridin-3-yl]-N-methyl-isobutyramide The title compound was obtained as a light brown solid in 85% yield according to the procedure described above for the preparation of 4-o-tolyl-[2,4']bipyridinyl-5-carboxylic acid (3,5-bis-trifluoromethyl-benzyl)-methyl-amide (Example 5) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 3,4-difluorophenylboronic acid instead of 4-pyridylboronic acid.

MS m/e (%): 593 (M+H$^+$, 100).

EXAMPLE 53

N-[6-(4-Acetyl-thiophen-2-yl)-4-o-tolyl-pyridin-3-yl]-2-(3,5-bis-trifluoromethyl-phenyl)-N-methyl-isobutyramide The title compound was obtained as a light brown solid in 59% yield according to the procedure described above for the preparation of 4-o-tolyl-[2,4']bipyridinyl-5-carboxylic acid (3,5-bis-trifluoromethyl-benzyl)-methyl-amide (Example 5) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 5-acetyl-2-thiopheneboronic acid instead of 4-pyridylboronic acid.

MS m/e (%): 605 (M+H$^+$, 100).

EXAMPLE 54

(RS)-2-(3,5-Bis-trifluoromethyl-phenyl)-N-{6-[5-(1-hydroxy-ethyl)-thiophen-2-yl]-4-o-tolyl-pyridin-3-yl}-N-methyl-isobutyramide The title compound was obtained as a white solid in 64% yield after column chromatography according to the procedure described above for the preparation of (RS)-N-(3,5-bis-trifluoromethyl-benzyl)-6-[5-(1-hydroxy-ethyl)-thiophen-2-yl]-N-methyl-4-o-tolyl-nicotinamide (Example 39) using N-[6-(4-acetyl-thiophen-2-yl)-4-o-tolyl-pyridin-3-yl]-2-(3,5-bis-trifluoromethyl-phenyl)-N-methyl-isobutyramide (Example 53) instead of 6-(5-acetyl-thiophen-2-yl)-N-(3,5-bis-trifluoromethyl-benzyl)-N-methyl-4-o-tolyl-nicotinamide.

MS m/e (%): 607 (M+H$^+$, 100).

EXAMPLE 55

5-[(3,5-Bis-trifluoromethyl-benzyl)-methyl-carbamoyl]-4-o-tolyl-pyridine-2-carboxylic acid A mixture of 0.50 g (0.98 mmol) 5-[(3,5-bis-trifluoromethyl-benzyl)-methyl-carbamoyl]-4-o-tolylpyridine-2-carboxylic acid methyl ester (Example 6), 10 ml methanol, 10 ml dioxane and 10 ml 1N aqueous sodium hydroxide solution was stirred at room temperature for 17 h. Dilution with water was followed by washing with tert-butyl methyl ether. The aqueous layer was acidified to pH 2 with 1 M aqueous hydrochloric acid solution and extracted with four portions of dichloromethane. The combined dichloromethane extracts were dried with sodium sulfate and concentrated to give 0.38 g (78%) of the title compound as a white solid.

MS(ISN) m/e (%): 495 ([M-(H$^+$)]$^-$, 100).

EXAMPLE 56

4-o-Tolyl-pyridine-2,5-dicarboxylic acid 2-[(3,5-bis-trifluoromethyl-benzyl)-methyl-amide]5-cyclopropylamide A mixture of 80 mg (0.16 mmol) 5-[(3,5-bis-trifluoromethyl-benzyl)-methyl-carbamoyl]-4-o-tolyl-pyridine-2-carboxylic acid (Example 55), 0.12 ml (1.6 mmol) cyclopropylamine, 63 mg (0.32 mmol) N-(3-dimethylaminopropyl)-N'-ethylcarbodiimide hydrochloride and a catalytic amount of 4-(N,N-dimethylamino)pyridine in 2 ml dichloromethane was stirred at room temperature for 60 h. Addition of saturated aqueous ammonium chloride solution was followed by extraction with four portions of dichloromethane. The combined dichloromethane extracts were washed with saturated aqueous sodium carbonate solution, dried with sodium sulfate and concentrated. Column chromatography afforded 56 mg (65%) of the title compound as a white solid.

MS m/e (%): 536 (M+H$^+$, 100).

EXAMPLE 57

4-o-Tolyl-pyridine-2,5-dicarboxylic acid 2-[(3,5-bis-trifluoromethyl-benzyl)-methyl-amide]5-(cyclopropyl-methyl-amide)

To a solution of 49 mg (0.092 mmol) 4-o-tolyl-pyridine-2,5-dicarboxylic acid 2-[(3,5-bis-trifluoromethyl-benzyl)-methyl-amide]5-cyclopropylamide (Example 56) in 1 ml tetrahydrofuran 0.12 ml of a 0.91 M solution (0.11 mmol) of potassium hexamethyldisilazide in tetrahydrofuran were added at 0° C. After 30 min, 0.007 ml (0.1 mmol) methyl iodide were added. The reaction mixture was allowed to warm to room temperature over night. Quenching with water and 1 M aqueous hydrochloric acid solution and neutralization with saturated aqueous sodium bicarbonate solution was followed by extraction with three portions of ethyl acetate. The combined organic extracts were dried with sodium sulfate and concentrated. Flash column chromatography gave 38 mg (76%) of the title compound as an off-white solid.

MS m/e (%): 550 (M+H$^+$, 100).

EXAMPLE 58

N-(3,5-Bis-trifluoromethyl-benzyl)-N-methyl-6-(morpholine-4-carbonyl)-4-o-tolyl-nicotinamide The title compound was obtained as a white solid in 85% yield after column chromatography according to the procedure described above for the preparation of 4-o-tolyl-pyridine-2,5-dicarboxylic acid 2-[(3,5-bis-trifluoromethyl-benzyl)-methyl-amide]5-cyclopropylamide (Example 56) using morpholine instead of cyclopropylamine.

MS m/e (%): 566 (M+H$^+$, 100).

EXAMPLE 59

4-o-Tolyl-pyridine-2,5-dicarboxylic acid 2-[(3,5-bis-trifluoromethyl-benzyl)-methyl-amide]5-[(2-hydroxy-ethyl)-amide]

The title compound was obtained as a white solid in 65% yield after column chromatography according to the procedure described above for the preparation of 4-o-tolyl-pyridine-2,5-dicarboxylic acid 2-[(3,5-bis-trifluoromethyl-benzyl)-methyl-amide]5-cyclopropylamide (Example 56) using ethanolamine instead of cyclopropylamine.

MS m/e (%): 540 (M+H$^+$, 100).

EXAMPLE 60

4-o-Tolyl-pyridine-2,5-dicarboxylic acid 2-[(3,5-bis-trifluoromethyl-benzyl)-methyl-amide]5-(carbamoylmethyl-methyl-amide)

The title compound was obtained as a white solid in 8% yield after preparative thinlayer chromatography according to the procedure described above for the preparation of 4-o-tolyl-pyridine-2,5-dicarboxylic acid 2-[(3,5-bis-trifluoromethyl-benzyl)-methyl-amide]5-cyclopropylamide (Example 56) using an equimolar mixture of sarcosine hydrochloride and triethylamine instead of cyclopropylamine.

MS m/e (%): 567 (M+H$^+$, 100).

EXAMPLE 61

4-o-Tolyl-pyridine-2,5-dicarboxylic acid 2-amide 5-[(3,5-bis-trifluoromethyl-benzyl)-methyl-amide]

To a solution of 200 mg (0.403 mmol) 5-[(3,5-bis-trifluoromethyl-benzyl)-methyl-carbamoyl]-4-o-tolyl-pyrid tetrahydrofuran 0.042 ml (0.48 mmol) oxalyl chloride and two drops of N,N-dimethylformamide were added dropwise at room temperature. After stirring for 1.5 h the reaction mixture was cooled to 0° C., followed by addition of 3 ml of a 25% aqueous solution of ammonium hydroxide. Dilution with water was followed by extraction with four portions of ethyl acetate. The combined organic extracts were dried with sodium sulfate and concentrated to give 199 mg (99.7%) of the title compound as a light orange-yellow solid.

MS m/e (%): 496 (M+H$^+$, 100).

EXAMPLE 62

N-(3,5-Bis-trifluoromethyl-benzyl)-N-methyl-6-(3-methyl-[1,2,4]oxadiazol-5-yl)-4-o-tolyl-nicotinamide A solution of 170 mg (0.343 mmol) 4-o-tolyl-pyridine-2,5-dicarboxylic acid 2-amide 5-[(3,5-bis-trifluoromethyl-benzyl)-methyl-amide](Example 61) in 1 ml N,N-dimethylformamide dimethyl acetal was heated at 120° C. for 1 h. After concentration in vacuo the residue was dissolved in 0.4 ml acetic acid. A solution of 29 mg (0.41 mmol) hydroxylamine hydrochloride in 0.2 ml 2N aqueous sodium hydroxide solution was added at room temperature. The mixture was heated at 90° C. for 1.5 h. After cooling to room temperature water and aqueous saturated sodium bicarbonate solution were added, followed by extraction with three portions of dichloromethane. The combined organic extracts were dried with sodium sulfate and concentrated. Column chromatography and preparative HPLC afforded 68 mg (37%) of the title compound as a light yellow solid.

MS m/e (%): 535 (M+H$^+$, 100).

EXAMPLE 63

N-(3,5-Bis-trifluoromethyl-benzyl)-6-ethynyl-N-methyl-4-o-tolyl-nicotinamide a) N-(3,5-Bis-trifluoromethyl-benzyl)-N-methyl-4-o-tolyl-6-trimethylsilanylethynyl-nicotinamide To a mixture of 200 mg (0.346 mmol) N-(3,5-bis-trifluoromethyl-benzyl)-6-iodo-N-methyl-4-o-tolyl-nicotinamide (Example 4), 0.073 ml (0.52 mmol) triethylamine, 5 mg (0.007 mmol) bis(triphenylphosphine) palladium(II) chloride and 3 mg (0.014 mmol) copper(I) iodide in 1 ml tetrahydrofuran a solution of 0.098 ml (0.69 mmol) trimethylsilylacetylene in 0.5 ml tetrahydrofuran was added at room temperature. After stirring for 17 h the mixture was diluted with tert-butyl methyl ether. Washing with a saturated aqueous solution of ammonium chloride was followed by drying with sodium sulfate and evaporation of the solvent. Column chromatography afforded 158 mg (83%) of the title compound as a light brown solid.

MS m/e (%): 549 (M+H$^+$, 100).

b) N-(3,5-Bis-trifluoromethyl-benzyl)-6-ethynyl-N-methyl-4-o-tolyl-nicotinamide

A mixture of 143 mg (0.261 mmol) N-(3,5-bis-trifluoromethyl-benzyl)-N-methyl-4-o-tolyl-6-trimethylsilanylethynyl-nicotinamide, 2.5 ml of a 1 M aqueous solution of potassium hydroxide and 2.5 ml methanol was stirred at room temperature for 1h. Acidifying to pH 5 with a saturated aqueous solution of ammonium chloride was followed by extraction with three portions of dichloromethane. The combined organic extracts were dried with sodium sulfate and concentrated. Column chromatography afforded 97 mg (78%) of the title compound as a light brown solid.

MS m/e (%): 475 ([M−H]$^+$, 4).

EXAMPLE 64

N-(3,5-Bis-trifluoromethyl-benzyl)-N-methyl-6-(3-methyl-isoxazol-5-yl)-4-o-tolyl-nicotinamide To a solution of 55 mg (0.12 mmol) N-(3,5-bis-trifluoromethyl-benzyl)-6-ethynyl-N-methyl-4-o-tolyl-nicotinamide (Example 63), 0.026 ml (0.35 mmol) nitroethane and 1 mg (0.01 mmol) 4-N,N-dimethylaminopyridine in 0.5 ml acetonitrile a solution of 77 mg (0.35 mmol) di-tert-butyl dicarbonate in 0.1 ml toluene was added, and the mixture was stirred at room temperature over night. Another portion of 0.026 ml (0.35 mmol) nitroethane and 77 mg (0.35 mmol) di-tert-butyl dicarbonate were added, and stirring was continued for 24 h. Quenching with water was followed by extraction with two portions of ethyl acetate. The combined organic extracts were dried with sodium sulfate and concentrated. Column chromatography afforded 21 mg (34%) of the title compound as a light yellow amorphous mass.

MS m/e (%): 534 (M+H$^+$, 100).

EXAMPLE 65

6-(3-Amino-prop-1-ynyl)-N-(3,5-bis-trifluoromethyl-benzyl)-N-methyl-4-o-tolyl-nicotinamide a) N-(3,5-Bis-trifluoromethyl-benzyl)-6-[3-(1,3-dioxo-1,3-dihydro-isoindol-2-yl)-prop-1-ynyl]-N-methyl-4-o-tolyl-nicotinamide The title compound was obtained as a white solid in 68% yield after column chromatography according to the procedure described above for the preparation of N-(3,5-bis-trifluoromethyl-benzyl)-N-methyl-4-o-tolyl-6-trimethylsilanylethynyl-nicotinamide (Example 63, step a)) using N-propargylphthalimide instead of trimethylsilylacetylene.

MS m/e (%): 636 (M+H$^+$, 100).

b) 6-(3-Amino-prop-1-ynyl)-N-(3,5-bis-trifluoromethyl-benzyl)-N-methyl-4-o-tolyl-nicotinamide A mixture of 206 mg (0.324 mmol) N-(3,5-bis-trifluoromethyl-benzyl)-6-[3-(1,3-dioxo-1,3-dihydro-isoindol-2-yl)-prop-1-ynyl]-N-methyl-4-o-tolyl-nicotinamide and 0.061 ml (0.97 mmol) hydrazine hydrate (51% hydrazine) in 3.5 ml ethanol was stirred at room temperature for 1 h. The reaction mixture was diluted with tert-butyl methyl ether and washed with 1N aqueous sodium hydroxide solution. The aqueous layer was extracted with three portions of tert-butyl methyl ether. The combined organic extracts were dried with sodium sulfate and concentrated. Column chromatography afforded 93 mg (57%) of the title compound as a light brown solid.

MS m/e (%): 506 (M+H$^+$, 100).

EXAMPLE 66

2-(3,5-Bis-trifluoromethyl-phenyl)-N-(6-ethynyl-4-o-tolyl-pyridin-3-yl)-N-methyl-isobutyramide a) 2-(3,5-Bis-trifluoromethyl-phenyl)-N-methyl-N-(4-o-tolyl-6-trimethylsilanylethynyl-pyridin-3-yl)-isobutyramide The title compound was obtained as an orange gum in quantitative yield after column chromatography according to the procedure described above for the preparation of N-(3,5-bis-trifluoromethyl-benzyl)-N-methyl-4-o-tolyl-6-trimethylsilanylethynyl-nicotinamide (Example 63, step a)) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide.

MS m/e (%): 577 (M+H$^+$, 100).

b) 2-(3,5-Bis-trifluoromethyl-phenyl)-N-(6-ethynyl-4-o-tolyl-pyridin-3-yl)-N-methyl-isobutyramide The title compound was obtained as a brown viscous oil in 52% yield after column chromatography according to the procedure described above for the preparation of N-(3,5-bis-trifluoromethyl-benzyl)-6-ethynyl-N-methyl-4-o-tolyl-nicotinamide (Example 63, step b)) using 2-(3,5-bis-trifluoromethyl-phenyl)-N-methyl-N-(4-o-tolyl-6-trimethylsilanylethynyl-pyridin-3-yl)-isobutyramide instead of N-(3,5-bis-trifluoromethyl-benzyl)-N-methyl-4-o-tolyl-6-trimethylsilanylethynyl-nicotinamide.

MS m/e (%): 505 (M+H$^+$, 100).

EXAMPLE 67

2-(3,5-Bis-trifluoromethyl-phenyl)-N-methyl-N-[6-(3-methyl-isoxazol-5-yl)-4-o-tolyl-pyridin-3-yl]-isobutyramide The title compound was obtained as a light brown solid in 34% yield after column chromatography according to the procedure described above for the preparation of N-(3,5-bis-trifluoromethyl-benzyl)-N-methyl-6-(3-methyl-isoxazol-5-yl)-4-o-tolyl-nicotinamide (Example 64) using 2-(3,5-bis-trifluoromethyl-phenyl)-N-(6-ethynyl-4-o-tolyl-pyridin-3-yl)-N-methyl-isobutyramide (Example 66) instead of N-(3,5-bis-trifluoromethyl-benzyl)-6-ethynyl-N-methyl-4-o-tolyl-nicotinamide.

MS m/e (%): 562 (M+H$^+$, 100).

EXAMPLE 68

2-(3,5-Bis-trifluoromethyl-phenyl)-N-[6-(3-ethyl-isoxazol-5-yl)-4-o-tolyl-pyridin-3-yl]-N-methyl-isobutyramide The title compound was obtained as a viscous light yellow oil in 17% yield after column chromatography according to the procedure described above for the preparation of N-(3,5-bis-trifluoromethyl-benzyl)-N-methyl-6-(3-methyl-isoxazol-5-yl)-4-o-tolyl-nicotinamide (Example 64) using 2-(3,5-bis-trifluoromethyl-phenyl)-N-(6-ethynyl-4-o-tolyl-pyridin-3-yl)-N-methyl-isobutyramide (Example 66) instead of N-(3,5-bis-trifluoromethyl-benzyl)-6-ethynyl-N-methyl-4-o-tolyl-nicotinamide and 1-nitropropane instead of nitroethane.

MS m/e (%): 576 (M+H$^+$, 100).

EXAMPLE 69

2-(3,5-Bis-trifluoromethyl-phenyl)-N-[6-(3-hydroxymethyl-isoxazol-5-yl)-4-o-tolyl-pyridin-3-yl]-N-methyl-isobutyramide To a solution of 200 mg (0.396 mmol) 2-(3,5-bis-trifluoromethyl-phenyl)-N-(6-ethynyl-4-o-tolyl-pyridin-3-yl)-N-methyl-isobutyramide (Example 66), 0.182 ml (1.19 mmol) 2-(2-nitroethoxy)tetrahydropyran and 5 mg (0.04 mmol) 4-N,N-dimethylaminopyridine in 3 ml acetonitrile a solution of 260 mg (1.19 mmol) di-tert-butyl dicarbonate in 2 ml toluene was added, and the mixture was stirred at room temperature for 70 h. Quenching with water was followed by extraction with two portions of ethyl acetate. The combined organic extracts were dried with sodium sulfate and concentrated. The residue was dissolved in 1.5 ml methanol and treated with 4 mg (0.02 mmol) 4-toluenesulfonic acid monohydrate. After stirring for 1.5 h at room temperature the solvent was evaporated. The residue was dissolved in ethyl acetate. Washing with saturated sodium bicarbonate solution was followed by drying with sodium sulfate and concentration. Column chromatography afforded 35 mg (15%) of the title compound as a viscous orange oil.

MS m/e (%): 578 (M+H$^+$, 100).

EXAMPLE 70

2-(3,5-Bis-trifluoromethyl-phenyl)-N-methyl-N-[4-o-tolyl-6-(1H-1,2,3]triazol-4-yl)-pyridin-3-yl]-isobutyramide A mixture of 300 mg (0.595 mmol) 2-(3,5-bis-trifluoromethyl-phenyl)-N-(6-ethynyl-4-o-tolyl-pyridin-3-yl)-N-methyl-isobutyramide (Example 66) and 0.30 ml (2.3 mmol) trimethylsilyl azide was heated at 150° C. in a sealed tube over night. Cooling to 0° C. was followed by addition of 10 ml ethanol. The mixture was allowed to warm to room temperature, stirred for 1 h and concentrated. Column chromatography afforded 222 mg (68%) of the title compound as a light brown solid.

MS m/e (%): 548 (M+H$^+$, 100).

EXAMPLE 71

2-(3,5-Bis-trifluoromethyl-phenyl)-N-methyl-N-[6-(2-methyl-pyridin-4-ylethynyl)-4-o-tolyl-pyridin-3-yl]-isobutyramide The title compound was obtained as as a brown viscous oil in 61% yield after column chromatography according to the procedure described above for the preparation of N-(3,5-bis-trifluoromethyl-benzyl)-N-methyl-4-o-tolyl-6-trimethylsilanylethynyl-nicotinamide (Example 63, step a)) using 4-iodo-2-methyl-pyridine (Example 46, step a)) instead of N-(3,5-bis-trifluoromethyl-benzyl)-6-iodo-N-methyl-4-o-tolyl-nicotinamide and 2-(3,5-bis-trifluoromethyl-phenyl)-N-(6-ethynyl-4-o-tolyl-pyridin-3-yl)-N-methyl-isobutyramide (Example 66) instead of trimethylsilylacetylene.

MS m/e (%): 596 (M+H$^+$, 100).

EXAMPLE 72

2-(3,5-Bis-trifluoromethyl-phenyl)-N-methyl-N-(6-phenylethynyl-4-o-tolyl-pyridin-3-yl)-isobutyramide The title compound was obtained as as a brown solid in 60% yield after column chromatography according to the procedure described above for the preparation of N-(3,5-bis-trifluoromethyl-benzyl)-N-methyl-4-o-tolyl-6-trimethylsilanylethynyl-nicotinamide (Example 63, step a)) using iodobenzene instead of N-(3,5-bis-trifluoromethyl-benzyl)-6-iodo-N-methyl-4-o-tolyl-nicotinamide and 2-(3,5-bis-trifluoromethyl-phenyl)-N-(6-ethynyl-4-o-tolyl-pyridin-3-yl)-N-methyl-isobutyramide (Example 66) instead of trimethylsilylacetylene.

MS m/e (%): 581 (M+H$^+$, 100).

EXAMPLE 73

(Z)-2-(3,5-Bis-trifluoromethyl-phenyl)-N-methyl-N-(6-styryl-4-o-tolyl-pyridin-3-yl)-isobutyramide A mixture of 100 mg (0.198 mmol) 2-(3,5-bis-trifluoromethyl-phenyl)-N-methyl-N-(6-phenylethynyl-4-o-tolyl-pyridin-3-yl)-isobutyramide (Example 72), 10 mg (0.17 mmol) ethylenediamine and 1 mg 10% palladium on carbon in 2 ml methanol was stirred at room temperature under an atmosphere of hydrogen gas for 8 h. The reaction mixture was filtered and concentrated. Column chromatography afforded 28 mg (24%) of the title compound as an orange viscous oil.

MS m/e (%): 583 (M+H$^+$, 100).

EXAMPLE 74

2-(3,5-Bis-trifluoromethyl-phenyl)-N-methyl-N-(6-phenethyl-4-o-tolyl-pyridin-3-yl)-isobutyramide A mixture of 20 mg (0.034 mmol) (Z)-2-(3,5-bis-trifluoromethyl-phenyl)-N-methyl-N-(6-styryl-4-o-tolyl-pyridin-3-yl)-isobutyramide (Example 73) and 2 mg 10% palladium on carbon in 1 ml methanol was stirred at room temperature under an atmosphere of hydrogen gas for 2 h. The reaction mixture was filtered and concentrated. Column chromatography afforded 14 mg (72%) of the title compound as an orange waxy solid.

MS m/e (%): 585 (M+H$^+$, 100).

EXAMPLE 75

2-(3,5-Bis-trifluoromethyl-phenyl)-N-[6-(3-hydroxy-prop-1-ynyl)-4-o-tolyl-pyridin-3-yl]-N-methyl-isobutyramide a) 2-(3,5-Bis-trifluoromethyl-phenyl)-N-{6-[3-(tert-butyl-dimethyl-silanyloxy)-prop-1-ynyl]-4-o-tolyl-pyridin-3-yl}-N-methyl-isobutyramide The title compound was obtained as an orange gum in 78% yield after column chromatography according to the procedure described above for the preparation of N-(3,5-bis-trifluoromethyl-benzyl)-N-methyl-4-o-tolyl-6-trimethylsilanylethynyl-nicotinamide (Example 63, step a)) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and tert-butyldimethyl(2-propynyloxy)silane instead of trimethylsilylacetylene.

MS m/e (%): 649 (M+H$^+$, 100).

b) 2-(3,5-Bis-trifluoromethyl-phenyl)-N-[6-(3-hydroxy-prop-1-ynyl-4-o-tolyl-pyridin-3-yl]-N-methyl-isobutyramide To a solution of 167 mg (0.257 mmol) 2-(3,5-bis-trifluoromethyl-phenyl)-N-{6-[3-(tert-butyl-dimethyl-silanyloxy)-prop-1-ynyl]-4-o-tolyl-pyridin-3-yl}-N-methyl-isobutyramide in 1.5 ml tetrahydrofuran a 1 M solution of tetrabutylammonium fluoride in tetrahydrofuran was added at room temperature. After stirring for 0.5 h water was added, followed by extraction with four portions of ethyl acetate. The combined organic extracts were dried with sodium sulfate and concentrated. Column chromatography afforded 82 mg (60%) of the title compound as a brown viscous oil.

MS m/e (%): 535 (M+H$^+$, 100).

EXAMPLE 76

(RS)-N-(3,5-Bis-trifluoromethyl-benzyl)-6-(hydroxy-phenyl-methyl)-N-methyl-4-o-tolyl-nicotinamide To 1.8 ml of a 1 M solution of isopropyl magnesium bromide in tetrahydrofuran (1.8 mmol) a solution of 500 mg (0.865 mmol) N-(3,5-bis-trifluoromethyl-benzyl)-6-iodo-N-methyl-4-o-tolyl-nicotinamide (Example 4) in 10 ml tetrahydrofuran was added dropwise at 40° C. After 2 h 0.116 ml (I1.15 mmol) benzaldehyde were added. The reaction mixture was allowed to warm to room temperature over night. Addition of water and saturated aqueous ammonium chloride solution was followed by extraction with three portions of ethyl acetate. The combined organic extracts were dried with sodium sulfate and concentrated. Column chromatography afforded 274 mg (57%) of the title compound as an off-white foam.

MS m/e (%): 559 (M+H$^+$, 100).

EXAMPLE 77

(RS)-N-(3,5-Bis-trifluoromethyl-benzyl)-6-(1-hydroxy-hexyl)-N-methyl-4-o-tolyl-nicotinamide The title compound was obtained as an off-white foam in 34% yield after column chromatography according to the procedure described above for the preparation of (RS)-N-(3,5-bis-trifluoromethyl-benzyl)-6-(hydroxy-phenyl-methyl)-N-methyl-4-o-tolyl-nicotinamide (Example 76) using hexanal instead of benzaldehyde.

MS m/e (%): 553 (M+H$^+$, 100).

EXAMPLE 78

(RS)-N-(3,5-Bis-trifluoromethyl-benzyl)-6-(1-chloro-hexyl)-N-methyl-4-o-tolyl-nicotinamide A solution of 50 mg (0.090 mmol) (RS)-N-(3,5-bis-trifluoromethyl-benzyl)-6-(1-hydroxy-hexyl)-N-methyl-4-o-tolyl-nicotinamide (Example 77) and 0.032 ml (0.23 mmol) triethylamine in 3 ml dichloromethane was treated with 0.008 ml (0.1 mmol) methanesulfonyl chloride at 0° C. The reaction mixture was stirred at 0° C. for 10 min and then allowed to warm to room temperature. After 1 h 3 ml toluene were added, and the mixture was stirred at 80° C. over night. Cooling to room temperature was followed by dilution with dichloromethane, washing with water, drying with sodium sulfate and concentration. Column chromatography gave 43 mg (83%) of the title compound as a light yellow viscous oil.

MS m/e (%): 571 (M+H$^+$, 100).

EXAMPLE 79

6-Benzoyl-N-(3,5-bis-trifluoromethyl-benzyl)-N-methyl-4-o-tolyl-nicotinamide

To a solution of 0.018 ml (0.21 mmol) oxalyl chloride in 2.5 ml dichloromethane 0.03 ml (0.4 mmol) dimethylsulfoxide were added at −78° C. After 5 min a solution of 100 mg (0.179 mmol) (RS)-N-(3,5-bis-trifluoromethyl-benzyl)-6-(hydroxy-phenyl-methyl)-N-methyl-4-o-tolyl-nicotinamide (Example 76) in 2.5 ml dichloromethane were added dropwise at −78° C. After stirring for another 30 min at −78° C. 0.15 ml (0.90 mmol) triethylamine were added. The reaction mixture was allowed to warm to room temperature. Dilution with dichloromethane was followed by washing with three portions of 1 M aqueous hydrochloric acid solution and one portion of a saturated aqueous solution of sodium bicarbonate. The organic layer was dried with sodium sulfate and concentrated. Column chromatography afforded 69 mg (70%) of the title compound as a light-yellow foam.

MS m/e (%): 557 (M+H$^+$, 100).

EXAMPLE 80

N-(3,5-Bis-trifluoromethyl-benzyl)-N-methyl-6-(pyridine-4-carbonyl)-4-o-tolyl-nicotinamide a) (RS)-N-(3,5-Bis-trifluoromethyl-benzyl)-6-(hydroxy-pyridin-4-yl-methyl)-N-methyl-4-o-tolyl-nicotinamide The title compound was obtained as a light brown foam in 18% yield after column chromatography according to the procedure described above for the preparation of (RS)-N-(3,5-bis-trifluoromethyl-benzyl)-6-(hydroxy-phenyl-methyl)-N-methyl-4-o-tolyl-nicotinamide (Example 76) using 4-pyridinecarboxaldehyde instead of benzaldehyde.

MS m/e (%): 560 (M+H$^+$, 100).

b) N-(3,5-Bis-trifluoromethyl-benzyl)-N-methyl-6-(pyridine-4-carbonyl)-4-o-tolyl-nicotinamide The title compound was obtained as an orange-brown solid in 26% yield after column chromatography according to the procedure described above for the preparation of 6-benzoyl-N-(3,5-bis-trifluoromethyl-benzyl)-N-methyl-4-o-tolyl-nicotinamide (Example 79) using (RS)-N-(3,5-bis-trifluoromethyl-benzyl)-6-(hydroxy-pyridin-4-yl-methyl)-N-methyl-4-o-tolyl-nicotinamide instead of (RS)-N-(3,5-bis-trifluoromethyl-benzyl)-6-(hydroxy-phenyl-methyl)-N-methyl-4-o-tolyl-nicotinamide.

MS m/e (%): 558 (M+H$^+$, 100).

EXAMPLE 81

N-(3,5-Bis-trifluoromethyl-benzyl)-N-methyl-4-o-tolyl-6-(3-trifluoromethyl-phenoxymethyl)-nicotinamide A solution of 80 mg (0.17 mmol) N-(3,5-bis-trifluoromethyl-benzyl)-6-hydroxymethyl-N-methyl-4-o-tolyl-nicotinamide (Example 7), 0.027 ml (0.22 mmol) 3-hydroxybenzotrifluoride, 47 mg (0.17 mmol) triphenylphosphine and 32 mg (0.17 mmol) diethyl azodicarboxylate in 2 ml tetrahydrofuran was stirred at room temperature over night. The reaction mixture was diluted with ethyl acetate and washed with 1N aqueous sodium hydroxide solution. The aqueous layer was extracted with three portions of ethyl acetate. The combined organic extracts were dried with sodium sulfate and concentrated. Column chromatography afforded 62 mg (60%) of the title compound as a light yellow amorphous mass.

MS m/e (%): 627 (M+H$^+$, 100).

EXAMPLE 82

N-(3,5-Bis-trifluoromethyl-benzyl)-N-methyl-6-(2-methyl-imidazol-1-yl-methyl)-4-o-tolyl-nicotinamide To a solution of 100 mg (0.207 mmol) N-(3,5-bis-trifluoromethyl-benzyl)-6-hydroxymethyl-N-methyl-4-o- tolyl-nicotinamide (Example 7) in 1 ml dichloromethane 0.03 ml (0.4 mmol) thionyl chloride were added at 0° C. The reaction mixture was allowed to warm to room temperature and stirred for 1 h. The solvent was evaporated and the light yellow residue was dried in high vacuo. The residue was dissolved in 1 ml dry N,N-dimethylformamide and added to a suspension of 2-methylimidazole sodium salt that had previously been prepared by addition of 54 mg (1.2 mmol) sodium hydride (55% dispersion in mineral oil) to a solution of 52 mg (0.62 mmol) 2-methylimidazole in 3 ml dry N,N-dimethylformamide under argon at room temperature. After stirring for 3 h the reaction was quenched by addition of excess water, followed by extraction with three portions of ethyl acetate. The combined organic extracts were dried with sodium sulfate and concentrated. Column chromatography afforded 52 mg (46%) of the title compound as an orange solid.

MS m/e (%): 547 (M+H$^+$, 100).

EXAMPLE 83

N-(3,5-Bis-trifluoromethyl-benzyl)-N-methyl-6-morpholin-4-yl-methyl-4-o-tolyl-nicotinamide The title compound was obtained as a viscous brown oil in 82% yield after column chromatography according to the procedure described above for the preparation of N-(3,5-bis-trifluoromethyl-benzyl)-N-methyl-6-(2-methyl-imidazol-1-yl-methyl)-4-o-tolyl-nicotinamide (Example 82) using morpholine instead of 2-methylimidazole and potassium carbonate instead of sodium hydride.

MS m/e (%): 552 (M+H$^+$, 100).

EXAMPLE 84

N-(3,5-Bis-trifluoromethyl-benzyl)-6-(2-hydroxy-ethylsulfanylmethyl)-N-methyl-4-o-tolyl-nicotinamide The title compound was obtained as a viscous yellow oil in 39% yield after column chromatography according to the procedure described above for the preparation of N-(3,5-bis-trifluoromethyl-benzyl)-N-methyl-6-(2-methyl-imidazol-1-ylmethyl)-4-o-tolyl-nicotinamide (Example 82) using 2-mercaptoethanol instead of 2-methylimidazole and potassium carbonate instead of sodium hydride.

MS m/e (%): 543 (M+H$^+$, 100).

EXAMPLE 85

(RS)-N-(3,5-Bis-trifluoromethyl-benzyl)-6-(2-hydroxy-ethanesulfinylmethyl)-N-methyl-4-o-tolyl-nicotinamide and

EXAMPLE 86

N-(3,5-Bis-trifluoromethyl-benzyl)-6-(2-hydroxy-ethanesulfonyl)-N-methyl-4-o-tolyl-nicotinamide To a solution of 30 mg (0.057 mmol) N-(3,5-bis-trifluoromethyl-benzyl)-6-(2-hydroxy-ethylsulfanylmethyl)-N-methyl-4-o-tolyl-nicotinamide (Example 84) in 2 ml dichloromethane a solution of 14 mg (0.057 mmol) 3-chloroperbenzoic acid (70%) in 1 ml dichloromethane was added at 0° C. After 30 min the reaction mixture was diluted with dichloromethane, washed with 1 M aqueous sodium hydroxide solution, dried with magnesium sulfate and concentrated. Column chromatography afforded 18 mg (58%) (RS)-N-(3,5-bis-trifluoromethyl-benzyl)-6-(2-hydroxy-ethanesulfinylmethyl)-N-methyl-4-o-tolyl-nicotinamide as a viscous colorless oil and 4.3 mg (14%) N-(3,5-bis-trifluoromethyl-benzyl)-6-(2-hydroxy-ethanesulfonyl)-N-methyl-4-o-tolyl-nicotinamide as a viscous light-yellow oil. (RS)-N-(3,5-Bis-trifluoromethyl-benzyl)-6-(2-hydroxy-ethanesulfinylmethyl)-N-methyl-4-o-tolyl-nicotinamide: MS m/e (%): 559 (M+H$^+$, 100). N-(3,5-Bis-trifluoromethyl-benzyl)-6-(2-hydroxy-ethanesulfonyl)-N-methyl-4-o-tolyl-nicotinamide:

MS m/e (%): 575 (M+H$^+$, 100).

EXAMPLE 87

N-(3,5-Bis-trifluoromethyl-benzyl)-N-methyl-6-(1-methyl-1H-imidazol-2-ylsulfanylmethyl)-4-o-tolyl-nicotinamide The title compound was obtained as a viscous yellow oil in 66% yield after column chromatography according to the procedure described above for the preparation of N-(3,5-bis-trifluoromethyl-benzyl)-N-methyl-6-(2-methyl-imidazol-1-ylmethyl)-4-o-tolyl-nicotinamide (Example 82) using 2-mercapto-1-methylimidazole instead of 2-methylimidazole and potassium carbonate instead of sodium hydride.

MS m/e (%): 579 (M+H$^+$, 100).

EXAMPLE 88

(RS)-N-(3,5-Bis-trifluoromethyl-benzyl)-N-methyl-6-(1-methyl-1H-imidazole-2-sulfinylmethyl)-4-o-tolyl-nicotinamide The title compound was obtained as a viscous light yellow oil in 87% yield after column chromatography according to the procedure described above for the preparation of (RS)-N-(3,5-bis-trifluoromethyl-benzyl)-6-(2-hydroxy-ethanesulfinylmethyl)-N-methyl-4-o-tolyl-nicotinamide (Example 85) using N-(3,5-bis-trifluoromethyl-benzyl)-N-methyl-6-(1-methyl-1H-imidazol-2-ylsulfanylmethyl)-4-o-tolyl-nicotinamide (Example 87) instead of N-(3,5-bis-trifluoromethyl-benzyl)-6-(2-hydroxy-ethylsulfanylmethyl)-N-methyl-4-o-tolyl-nicotinamide.

MS m/e (%): 595 (M+H$^+$, 100).

EXAMPLE 89

N-(3,5-Bis-trifluoromethyl-benzyl)-6-[3-(4-methoxy-phenyl)-propyl]-N-methyl-4-o-tolyl-nicotinamide Deoxygenation of a solution of 89 mg (0.58 mmol) 4-allylanisole in 3 ml tetrahydrofuran by three freeze-thaw cycles was followed by addition of 73 mg (0.29 mmol) 9-borabicyclo[3.3.1]nonane dimer at room temperature under an atmosphere of argon. After 1.5 h 43 mg (0.58 mmol) potassium methoxide were added, and stirring was continued for 20 min. In one portion 250 mg (0.432 mmol) N-(3,5-bis-trifluoromethyl-benzyl)-6-iodo-N-methyl-4-o-tolyl-nicotinamide (Example 4) were added, followed by a suspension of 10 mg (0.043 mmol) palladium(II) acetate and 37 mg (0.086 mmol) 1,3-bis-(2,6-diisopropyl-phenyl)-3H-imidazol-1-ium chloride in 0.5 ml tetrahydrofuran. The reaction mixture was heated at reflux for 2 h. Cooling to room temperature was followed by dilution with tert-butyl methyl ether and washing with two portions of 1 M aqueous sodium hydroxide solution. The combined aqueous layers were extracted with tert-butyl methyl ether. The combined organic extracts were dried with magnesium sulfate and concentrated. Column chromatography afforded 184 mg (71%) of the title compound as a light-yellow amorphous mass.

MS m/e (%): 601 (M+H$^+$, 100).

EXAMPLE 90

N-(3,5-Bis-trifluoromethyl-benzyl)-6-(4,4-dimethyl-pentyl)-N-methyl-4-o-tolyl-nicotinamide The title compound was obtained as a light-yellow amorphous mass in 72% yield after column chromatography according to the procedure described above for the preparation of N-(3,5-bis-trifluoromethyl-benzyl)-6-[3-(4-methoxy-phenyl)-propyl]-N-methyl-4-o-tolyl-nicotinamide (Example 89) using 4,4-dimethyl-1-pentene instead of 4-allylanisole.

MS m/e (%): 551 (M+H$^+$, 100).

EXAMPLE 91

N-(3,5-Bis-trifluoromethyl-benzyl)-6-(3-cyano-propyl)-N-methyl-4-o-tolyl-nicotinamide The title compound was obtained as a light-yellow amorphous mass in 72% yield after column chromatography according to the procedure described above for the preparation of N-(3,5-bis-trifluoromethyl-benzyl)-6-[3-(4-methoxy-phenyl)-propyl]-N-methyl-4-o-tolyl-nicotinamide (Example 89) using allylcyanide instead of 4-allylanisole.

MS m/e (%): 520 (M+H$^+$, 100).

EXAMPLE 92

N-(6-Acetyl-4-o-tolyl-pyridin-3-yl)-2-(3,5-bis-trifluoromethyl-phenyl)-N-methyl-isobutyramide A solution of 300 mg (0.495 mmol) 2-(3,5-bis-trifluoromethyl-phenyl)-N-(6-iodo-4-o-tolyl-pyridin-3-yl)-N-methyl-isobutyramide (Example 27) and 0.20 ml (0.59 mmol) 1-ethoxyvinyltri-n-butyltin in 1 ml toluene was deoxygenated by three freeze-thaw cycles. After addition of 17 mg (0.025 mmol) bis(triphenylphosphine)palladium(II) chloride the reaction mixture was heated at reflux for 16 h. Cooling to room temperature was followed by addition of 1 ml 2 M aqueous hydrochloric acid solution. After 15 min 2 ml 1N aqueous sodium hydroxide solution and 35 mg (0.59 mmol) potassium fluoride were added, followed by extraction with four portions of ethyl acetate. The combined organic layers were washed with brine, dried with magnesium sulfate and concentrated. Column chromatography afforded 147 mg (57%) of the title compound as a colorless gum.

MS m/e (%): 523 (M+H$^+$, 100).

EXAMPLE 93

6-(2-Amino-thiazol-4-yl)-N-(3,5-bis-trifluoromethyl-benzyl)-N-methyl-4-o-tolyl-nicotinamide a) N-(3,5-Bis-trifluoromethyl-benzyl)-6-(1-ethoxy-vinyl)-N-methyl-4-o-tolyl-nicotinamide A solution of 1.00 g (1.73 mmol) N-(3,5-bis-trifluoromethyl-benzyl)-6-iodo-N-methyl-4-o-tolyl-nicotinamide (Example 4) and 0.61 ml (1.8 mmol) 1-ethoxyvinyltri-n-butyltin in 5 ml toluene was deoxygenated by three freeze-thaw cycles. After addition of 61 mg (0.087 mmol) bis(triphenylphosphine)palladium(II) chloride the reaction mixture was heated at reflux for 16 h. The mixture was cooled to room temperature, treated with 500 mg (2.25 mmol) potassium fluoride on aluminum oxide (5.5 mmol fluoride/g) and stirred for 15 min. After filtration and washing with toluene the filtrate was concentrated. Column chromatography afforded 592 mg (66%) of the title compound as a light yellow foam.

MS m/e (%): 523 (M+H$^+$, 100).

b) N-(3,5-Bis-trifluoromethyl-benzyl)-6-bromoace(1-N-methyl-4-o-tolyl-nicotinamide A mixture of 592 mg (1.13 mmol) N-(3,5-bis-trifluoromethyl-benzyl)-6-(1-ethoxy-vinyl)-N-methyl-4-o-tolyl-nicotinamide and 203 mg (1.13 mmol) N-bromosuccinimide, 10 ml tetrahydrofuran and 1 ml water was stirred at room temperature for 1 h. The reaction mixture was diluted with ethyl acetate and washed with saturated sodium bicarbonate solution. The aqueous layer was extracted with two portions of ethyl acetate. The combined organic layers were dried with sodium sulfate and concentrated. Column chromatography afforded 586 mg (90%) of the title compound as a light orange viscous oil.

MS m/e (%): 573 (M+H$^+$, 100).

c) 6-(2-Amino-thiazol-4-yl)-N-(3,5-bis-trifluoromethyl-benzyl)-N-methyl-4-o-tolyl-nicotinamide A mixture of 73 mg (0.13 mmol) N-(3,5-bis-trifluoromethyl-benzyl)-6-bromoacetyl-N-methyl-4-o-tolyl-nicotinamide and 12 mg (0.15 mmol) thiourea in 1 ml ethanol was heated at reflux for 30 min. After cooling to room temperature the solvent was evaporated in vacuo and the residue was dissolved in ethyl acetate. Washing with 1 M aqueous sodium hydroxide solution was followed by extraction of the aqueous layer with three portions of ethyl acetate. The combined organic layers were dried with sodium sulfate and concentrated. Column chromatography afforded 62 mg (88%) of the title compound as a light orange solid.

MS m/e (%): 551 (M+H+, 100).

EXAMPLE 94

N-(3,5-Bis-trifluoromethyl-benzyl)-N-methyl-6-(2-methyl-thiazol-4-yl)-4-o-tolyl-nicotinamide The title compound was obtained as an off-white foam in comparable yield after column chromatography according to the procedures described above for the preparation of 6-(2-amino-thiazol-4-yl)-N-(3,5-bis-trifluoromethyl-benzyl)-N-methyl-4-o-tolyl-nicotinamide (Example 93) using thioacetamide instead of thiourea in step c).

MS m/e (%): 550 (M+H$^+$, 100).

EXAMPLE 95

5-{[2-(3,5-Bis-trifluoromethyl-phenyl)-2-methyl-propionyl]-methyl-amino}-4-o-tolyl-pyridine-2-carboxylic acid methyl ester A solution of 100 mg (0.165 mmol) 2-(3,5-bis-trifluoromethyl-phenyl)-N-(6-iodo-4-o-tolyl-pyridin-3-yl)-N-methyl-isobutyramide (Example 27), 0.046 ml (0.33 mmol) triethylamine, 4 mg (0.02 mmol) triphenylphosphine and 0.27 ml (6.6 mmol) methanol in 2.5 ml N,N-dimethylformamide was deoxygenated in a glas flask by three freeze-thaw cycles. After addition of 4 mg (0.02 mmol) palladium(II) acetate under argon the flask containing the reaction mixture was transferred to an autoclave which was sealed and pressurized with carbon monoxide gas to 60 bar. After stirring at 50° C. for 16 h the mixture was diluted with

EXAMPLE 96

N-(3,5-Bis-trifluoromethyl-benzyl)-6-methanesulfonyl-N-methyl-4-o-tolyl-nicotinamide A mixture of 369 mg (0.758 mmol) N-(3,5-bis-trifluoromethyl-benzyl)-6-chloro-N-methyl-4-o-tolyl-nicotinamide (Example 2) and 176 mg (1.67 mmol) sodium methanesulfinate in 4 ml N,N-dimethylformamide was heated at reflux over night. After cooling to room temperature the mixture was diluted with dichloromethane and treated with saturated aqueous sodium bicarbonate solution. The layers were separated and the aqueous layer was extracted with three portions of dichloromethane. The combined organic layers were dried with sodium sulfate, concentrated and and dried in high vacuo. Flash column chromatography gave 118 mg (29%) of the title compound as a white solid.

MS m/e (%): 531 (M+H$^+$, 100).

EXAMPLE 97

6-Benzenesulfonyl-N-(3,5-bis-trifluoromethyl-benzyl)-N-methyl-4-o-tolyl-nicotinamide The title compound was obtained as an off-white solid in 29% yield after column chromatography according to the procedure described above for the preparation of N-(3,5-bis-trifluoromethyl-benzyl)-6-methanesulfonyl-N-methyl-4-o-tolyl-nicotinamide (Example 96) using sodium benzenesulfinate instead of sodium methanesulfinate.

MS m/e (%): 593 (M+H$^+$, 100).

EXAMPLE 98

N-(3,5-Bis-trifluoromethyl-benzyl)-N-methyl-6-(pyridin-2-ylsulfanyl)-4-o-tolyl-nicotinamide A solution of 250 mg (0.432 mmol) N-(3,5-bis-trifluoromethyl-benzyl)-6-iodo-N-methyl-4-o-tolyl-nicotinamide (Example 4), 0.090 ml (0.65 mmol) triethylamine and 59 mg (0.52 mmol) 2-mercaptopyridine in 4 ml tetrahydrofuran was deoxygenated by three freeze-thaw cycles. After addition of 15 mg (0.022 mmol) bis(triphenylphosphine)palladium(II) chloride the reaction mixture was heated at reflux over night. Cooling to room temperature was followed by dilution with ethyl acetate and washing with saturated aqueous sodium carbonate solution and brine. The combined aqueous layers were extracted with ethyl acetate. The combined organic layers were dried with sodium sulfate and concentrated. Column chromatography afforded 210 mg (87%) of the title compound as a light yellow amorphous mass.

MS m/e (%): 562 (M+H$^+$, 100).

EXAMPLE 99

(RS)-N-(3,5-Bis-trifluoromethyl-benzyl)-N-methyl-6-(pyridine-2-sulfinyl)-4-o-tolyl-nicotinamide and

EXAMPLE 100

N-(3,5-Bis-trifluoromethyl-benzyl)-N-methyl-6-(pyridine-2-sulfonyl)-4-o-tolyl-nicotinamide A mixture of 198 mg (0.353 mmol) N-(3,5-bis-trifluoromethyl-benzyl)-N-methyl-6-(pyridin-2-ylsulfanyl)-4-o-tolyl-nicotinamide (Example 98), 216 mg (0.353 mmol) Oxone, 3.5 ml methanol and 0.7 ml water was stirred at room temperature for 70 h. Dilution with 1N aqueous sodium hydroxide solution was followed by extraction with three portions of dichloromethane. The combined organic layers were dried with sodium sulfate and concentrated. Column chromatography afforded 31 mg (15%) (RS)-N-(3,5-bis-trifluoromethyl-benzyl)-N-methyl-6-(pyridine-2-sulfinyl)-4-o-tolyl-nicotinamide as an off-white amorphous mass and 80 mg (38%) N-(3,5-bis-trifluoromethyl-benzyl)-N-methyl-6-(pyridine-2-sulfonyl)-4-o-tolyl-nicotinamide as an off-white amorphous mass. (RS)-N-(3,5-Bis-trifluoromethyl-benzyl)-N-methyl-6-(pyridine-2-sulfinyl)-4-o-tolyl-nicotinamide: MS m/e (%): 578 (M+H$^+$, 100). N-(3,5-Bis-trifluoromethyl-benzyl)-N-methyl-6-(pyridine-2-sulfonyl)-4-o-tolyl-nicotinamide: MS m/e (%): 594 (M+H$^+$, 100).

EXAMPLE 101

N-(3,5-Bis-trifluoromethyl-benzyl)-N-methyl-6-(4-methyl-4H-[1,2,4]triazol-3-ylsulfanyl)-4-o-tolyl-nicotinamide The title compound was obtained as a light yellow solid in 49% yield after column chromatography according to the procedure described above for the preparation of N-(3,5-bis-trifluoromethyl-benzyl)-N-methyl-6-(pyridin-2-ylsulfanyl)-4-o-tolyl-nicotinamide (Example 98) using 3-mercapto-4-methyl-4H-1,2,4-triazole instead of 2-mercaptopyridine.

MS m/e (%): 566 (M+H$^+$, 100).

EXAMPLE 102

2-(3,5-Bis-trifluoromethyl-phenyl)-N-[6-(4-methoxy-phenylsulfanyl)-4-o-tolyl-pyridin-3-yl]-N-methyl-isobutyramide The title compound was obtained as an orange gum in 22% yield after column chromatography according to the procedure described above for the preparation of N-(3,5-bis-trifluoromethyl-benzyl)-N-methyl-6-(pyridin-2-ylsulfanyl)-4-o-tolyl-nicotinamide (Example 98) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-methoxythiophenol instead of 2-mercaptopyridine.

MS m/e (%): 619 (M+H$^+$, 100).

EXAMPLE 103

2-(3,5-Bis-trifluoromethyl-phenyl)-N-[6-(3-methoxy-phenylsulfanyl)-4-o-tolyl-pyridin-3-yl]-N-methyl-isobutyramide The title compound was obtained as a grey solid in 71% yield after column chromatography according to the procedure described above for the preparation of N-(3,5-bis-trifluoromethyl-benzyl)-N-methyl-6-(pyridin-2-ylsulfanyl)-4-o-tolyl-nicotinamide (Example 98) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 3-methoxythiophenol instead of 2-mercaptopyridine.

MS m/e (%): 619 (M+H$^+$, 100).

EXAMPLE 104

(RS)-2-(3,5-Bis-trifluoromethyl-phenyl)-N-[6-(3-methoxy-benzenesulfinyl)-4-o-tolyl-pyridin-3-yl]-N-methyl-isobutyramide To a solution of 130 mg (0.210 mmol) 2-(3,5-bis-trifluoromethyl-phenyl)-N-[6-(3-methoxy-phenylsulfanyl)-

--- water and extracted with three portions of tert-butyl methyl ether. The combined organic extracts were washed with water, dried with sodium sulfate and concentrated. Flash chromatography afforded 48 mg (54%) of the title compound as an orange gum.

MS m/e (%): 539 (M+H$^+$, 100).

4-o-tolyl-pyridin-3-yl]-N-methyl-isobutyramide (Example 103) in 1 ml dichloromethane a solution of 52 mg (0.21 mmol) 3-chloroperbenzoic acid in 1.5 ml dichloromethane was added at 0° C. After completed addition the reaction mixture was allowed to warm to room temperature and stirred over night. The reaction mixture was diluted with dichloromethane and washed with saturated aqueous sodium carbonate solution. The aqueous layer was extracted with three portions of dichloromethane. The combined organic layers were dried with sodium sulfate and concentrated. Column chromatography afforded 9 mg (7%) of the title compound as a colorless viscous oil.

MS m/e (%): 635 (M+H$^+$, 100).

EXAMPLE 105

(5-{[2-(3,5-Bis-trifluoromethyl-phenyl)-2-methyl-propionyl]-methyl-amino}-4-o-tolyl-pyridin-2-ylsulfanyl)-acetic acid methyl ester The title compound was obtained as a viscous orange oil in 12% yield after column chromatography according to the procedure described above for the preparation of N-(3,5-bis-trifluoromethyl-benzyl)-N-methyl-6-(pyridin-2-ylsulfanyl)-4-o-tolyl-nicotinamide (Example 98) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and methyl thioglycolate instead of 2-mercaptopyridine.

MS m/e (%): 585 (M+H$^+$, 100).

EXAMPLE 106

3-(5-{[2-(3,5-Bis-trifluoromethyl-phenyl)-2-methyl-propionyl]-methyl-amino}-4-o-tolyl-pyridin-2-ylsulfanyl)-propionic acid methyl ester The title compound was obtained as a viscous colorless oil in 37% yield after column chromatography according to the procedure described above for the preparation of N-(3,5-bis-trifluoromethyl-benzyl)-N-methyl-6-(pyridin-2-ylsulfanyl)-4-o-tolyl-nicotinamide (Example 98) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and methyl 3-mercaptopropionate instead of 2-mercaptopyridine.

MS m/e (%): 599 (M+H$^+$, 100).

EXAMPLE 107

N-(3,5-Bis-trifluoromethyl-benzyl)-6-(3-cyano-phenoxy)-N-methyl-4-o-tolyl-nicotinamide A solution of 200 mg (0.346 mmol) N-(3,5-bis-trifluoromethyl-benzyl)-6-iodo-N-methyl-4-o-tolyl-nicotinamide (Example 4) and 84 mg (0.69 mmol) 3-hydroxybenzonitrile in 4 ml pyridine was deoxygenated by three freeze-thaw cycles. After addition of 5 mg (0.04 mmol) copper(I) oxide and 96 mg (0.69 mmol) potassium carbonate under a stream of argon the reaction mixture was heated at reflux for 70 h. Cooling to room temperature was followed by dilution with tert-butyl methyl ether and washing with two portions of 1 M aqueous hydrochloric acid solution. The combined aqueous layers were extracted with tert-butyl methyl ether. The combined organic layers were washed with saturated aqueous sodium carbonate solution and brine, dried with sodium sulfate and concentrated. Column chromatography afforded 174 mg (88%) of the title compound as a light brown solid.

MS m/e (%): 570 (M+H$^+$, 100).

EXAMPLE 108

2-(3,5-Bis-trifluoromethyl-phenyl)-N-methyl-N-[4-o-tolyl-6-(4-[1,2,4]triazol-1-yl-phenoxy)-pyridin-3-yl]-isobutyramide The title compound was obtained as a viscous light yellow oil in 78% yield after column chromatography according to the procedure described above for the preparation of N-(3,5-bis-trifluoromethyl-benzyl)-6-(3-cyano-phenoxy)-N-methyl-4-o-tolyl-nicotinamide (Example 107) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-(1,2,4-triazol-1-yl)phenol instead of 3-hydroxybenzonitrile.

MS m/e (%): 640 (M+H$^+$, 100).

EXAMPLE 109

2-(3,5-Bis-trifluoromethyl-phenyl)-N-[6-(4-methanesulfonyl-phenoxy)-4-o-tolyl-pyridin-3-yl]-N-methyl-isobutyramide The title compound was obtained as a light-yellow solid in 47% yield after column chromatography according to the procedure described above for the preparation of N-(3,5-bis-trifluoromethyl-benzyl)-6-(3-cyano-phenoxy)-N-methyl-4-o-tolyl-nicotinamide (Example 107) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-methylsulphonylphenol instead of 3-hydroxybenzonitrile.

MS m/e (%): 651 (M+H$^+$, 100).

EXAMPLE 110

2-(3,5-Bis-trifluoromethyl-phenyl)-N-[6-(4-cyano-phenoxy)-4-o-tolyl-pyridin-3-yl]-N-methyl-isobutyramide The title compound was obtained as a light-yellow solid in 77% yield after column chromatography according to the procedure described above for the preparation of N-(3,5-bis-trifluoromethyl-benzyl)-6-(3-cyano-phenoxy)-N-methyl-4-o-tolyl-nicotinamide (Example 107) using 2-(3,5-bis-trifluoromethyl-phenyl)-N-(6-iodo-4-o-tolyl-pyridin-3-yl)-N-methyl-isobutyramide (Example 27) instead of N-(3,5-bis-trifluoromethyl-benzyl)-6-iodo-N-methyl-4-o-tolyl-nicotinamide and 4-hydroxybenzonitrile instead of 3-hydroxybenzonitrile.

MS m/e (%): 598 (M+H$^+$, 100).

EXAMPLE 111

N-(3,5-Bis-trifluoromethyl-benzyl)-6-hydroxy-N-methyl-4-o-tolyl-nicotinamide a) 6-Chloro-N-methyl-nicotinamide To 50 g (317 mmol) of 2-chloronicotinic acid were added 230 ml (3.16 mol) thionyl chloride at 0° C. After heating the mixture at reflux for 2 h excess thionyl chloride was removed by distillation. The oily brown residue was dissolved in 250 ml dichloromethane. The solution was treated with methylamine gas at 0° C. until no exothermic reaction was observed any longer. The resulting suspension was diluted with 1000 ml dichloromethane/water. The layers were separated and the aqueous layer extracted with three 300-ml portions of dichloromethane. Drying of the combined organic layers with sodium sulfate and concentration gave 53.2 g (98%) of the title compound as a light yellow solid.

MS m/e (%): 171 (M+H$^+$, 15).

b) 6-Chloro-N-methyl-4-o-tolyl-nicotinamide

To a solution of 3.41 g (20.0 mmol) 6-chloro-N-methyl-nicotinamide in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic layer was washed with 4 250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid.) .M.p. 91–93° C.

MS m/e (%): 260 (M$^+$, 11).

c) N-Methyl-6-morpholin-4-yl-4-o-tolyl-nicotinamide

A mixture of 1.00 g (3.84 mmol) 6-chloro-N-methyl-4-o-tolyl-nicotinamide, 0.37 ml (4.22 mmol) morpholine, 2.0 ml (12 mmol) N-ethyldiisopropylamine and a catalytic amount of 4-(N,N-dimethylamino)-pyridine was heated at 100° C. over night. After cooling to room temperature the mixture was dissolved in ethyl acetate and washed with two portions of water. The combined aqueous layers were extracted with 3 portions of dichloromethane. Drying with sodium sulfate and concentration gave 1.23 g of the crude product. Flash column chromatography afforded 1.11 g (92.9%) of the title compound as an off-white solid. M.p. 156–158° C.

MS m/e (%): 311 (M$^+$, 64).

d) N-(3,5-Bis-trifluoromethyl-benzyl)-N-methyl-6-morpholin-4-yl-4-o-tolyl-nicotinamide To a solution of 0.27 g (0.87 mmol) N-methyl-6-morpholin-4-yl-4-o-tolyl-nicotinamide in 15 ml tetrahydrofuran, 1.12 ml of a 1 M solution (1.12 mmol) of potassium hexamethyldisilazide in tetrahydrofuran was added at 0° C. After 30 min, 0.16 ml (0.87 mmol) 3,5-bis(trifluoromethyl)benzyl bromide were added dropwise and the reaction mixture was allowed to warm to room temperature over night. Quenching with water was followed by extraction with ethyl acetate. The combined organic extracts were dried with sodium sulfate and concentrated. Column chromatography gave 0.20 g (44%) of the title compound as a white solid.

MS m/e (%): 538 (M+H$^+$, 100).

e) N-(3,5-Bis-trifluoromethyl-benzyl)-N-methyl-6-(4-oxy-morpholin-4-yl)-4-o-tolyl-nicotinamide monohydrate To a solution of 0.43 g (0.81 mmol) N-(3,5-bis-trifluoromethyl-benzyl)-N-methyl-6-morpholin-4-yl-4-o-tolyl-nicotinamide in 5 ml dichloromethane 0.15 g 3-chloroperbenzoic acid (70%; 0.76 mmol) were added at 0° C. After 1.5 h the reaction mixture was diluted with dichloromethane and washed with 3 portions of saturated sodium carbonate solution. The combined aqueous layers were extracted with dichloromethane. The combined organic extracts were washed with saturated sodium chloride solution, dried with sodium sulfate and concentrated. Column chromatography gave 0.29 g (65%) of the title compound as a white solid.

MS m/e (%): 554 (M+H$^+$, 100).

f) N-(3,5-Bis-trifluoromethyl-benzyl)-6-hydroxy-N-methyl-4-o-tolyl-nicotinamide

A solution of 0.29 g (0.52 mmol) N-(3,5-bis-trifluoromethyl-benzyl)-N-methyl-6-(4-oxy-morpholin-4-yl)-4-o-tolyl-nicotinamide monohydrate in 5 ml toluene was heated at reflux over night. After cooling to room temperature the reaction mixture was diluted with ethyl acetate and washed with 1 M aqueous hydrochloric acid solution. The organic layer was dried with sodium sulfate and concentrated. Column chromatography gave 0.17 g (71%) of the title compound as a viscous yellow oil.

MS m/e (%): 467 ([M–H]$^+$, 4).

EXAMPLE 112

6-Benzyloxy-N-(3,5-bis-trifluoromethyl-benzyl)-N-methyl-4-o-tolyl-nicotinamide

A mixture of 50 mg (0.11 mmol) N-(3,5-bis-trifluoromethyl-benzyl)-6-hydroxy-N-methyl-4-o-tolyl-nicotinamide (Example 111), 0.014 ml (0.12 mmol) benzyl bromide and 59 mg (0.21 mmol) silver carbonate in 2 ml dichloromethane was heated at reflux for 2 h. Cooling to room temperature was followed by dilution with dichloromethane and filtration. The filtrate was washed with water. The aqueous layer was extracted with three portions of dichloromethane. The combined organic layers were dried with sodium sulfate, concentrated and dried in high vacuo. Column chromatography afforded 24 mg (41%) of the title compound as a viscous light yellow oil.

MS m/e (%): 559 (M+H +, 100).

EXAMPLE 113

N-(3,5-Bis-trifluoromethyl-benzyl)-6-(3-hydroxy-propoxy)-N-methyl-4-o-tolyl-nicotinamide The title compound was obtained as a viscous light-red oil in 33% yield after column chromatography according to the procedure described above for the preparation of 6-benzyloxy-N-(3,5-bis-trifluoromethyl-benzyl)-N-methyl-4-o-tolyl-nicotinamide (Example 112) using 3-iodopropanol instead of benzyl bromide.

MS m/e (%): 527 (M+H$^+$, 100).

EXAMPLE 114

2-(3,5-Bis-trifluoromethyl-phenyl)-N-(6-hydroxy-4-o-tolyl-pyridin-3-yl)-N-methyl-isobutyramide a) 4-(5-Nitro-2-pyridyl)-morpholine To a solution of 20 g (126 mmol) of 2-chloro-5-nitropyridine in 150 ml tetrahydrofuran were added dropwise 27 ml (315 mmol) morpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.3 g (quantitative) of the title compound as a yellow solid. M.p. 142–143° C.

b) 2,2-Dimethyl-N-(6-morpholin-4-yl-pyridin-3-yl)-propionamide

To a solution of 27.3 g (126 mmol) of 4-(5-nitro-2-pyridyl)-morpholine in 600 ml methanol were added 2.5 g of 10% of palladium on activated charcoal. The reaction mixture was hydrogenated (room temperature to ca. 45° C., 1 bar) until the theoretical amount of hydrogen was taken up (about 3 h). The catalyst was filtered off and was washed twice with 100 ml portions of methanol. The filtrate was evaporated in vacuo to give 22.6 g of a purple oil which consisted to ca. 95% of the desired aniline derivative according to analysis by thin layer chromatography.

This crude product was dissolved in a mixture of 240 ml tetrahydrofuran and 60 ml diethyl ether. After cooling to 0° C., 26 ml (189 mmol) of triethylamine were added in one portion. Stirring was continued while 23 g (189 mmol) of pivaloyl chloride were added dropwise within a period of 10 min. The ice bath was removed and the reaction mixture was stirred for 1 h at room temperature. Then, the solvent was removed in vactio and the residue was suspended in 200 ml 1 N sodium bicarbonate solution. The product was extracted three times with 200 ml portions of dichloromethane, dried (sodium sulfate) and evaporated. Recrystallization of the solid residue from ethyl acetate/hexane 1:8 gave 28.6 g (86%) of the title compound as white crystals.

MS m/e (%): 264 (M+H$^+$, 100).

c) N-(4-Iodo-6-morpholin-4-yl-pyridin-3-yl)-2,2-dimethyl-propionamide

A solution of 28.4 g (108 mmol) 2,2-dimethyl-N-(6-morpholin-4-yl-pyridin-3-yl)-propionamide and 49 ml (324 mmol) N,N,N',N'-tetramethylethylenediamine under argon in 600 ml tetrahydrofuran was cooled in a dry ice bath to −78° C. Within 1 h, 202 ml (324 mmol) of a 1.6 N n-butyllithium solution in hexane were added dropwise. The reaction mixture was allowed to warm up to −35° C. overnight. After cooling again to −78° C., 37 g (146 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 15.6 g (37%) of the title compound as a light brown oil which crystallized upon standing at room temperature.

MS m/e (%): 389 (M$^+$, 71), 358 (25), 304 (43), 57 (100).

d) 2,2-Dimethyl-N-(6-morpholin-4-yl-4-o-tolyl-pyridin-3-yl)-propionamide

A mixture of 3.50 g (9.0 mmol) N-(4-iodo-6-morpholin-4-yl-pyridin-3-yl)-2,2-dimethyl-propionamide, 35 ml toluene, 18 ml 2 N sodium carbonate solution, 312 mg (0.27 mmol) tetrakis(triphenylphosphine)palladium(0) and 1.34 g (9.9 mmol) o-tolylboronic acid was heated under argon at 80° C. for 12 h. After cooling to room temperature, the aqueous phase was separated and washed twice with ethyl acetate. The combined organic layers were washed with 50 ml brine, dried (sodium sulfate) and evaporated. Purification by flash-chromatography gave 3.23 g (quantitative) of the title compound as a white foam.

MS m/e (%): 354 (M+H$^+$, 100).

e) 6-Morpholin-4-yl-4-o-tolyl-pyridin-3-yl-amine

A suspension of 2.93 g (8.28 mmol) 2,2-dimethyl-N-(6-morpholin-4-yl-4-o-tolyl-pyridin-3-yl)-propionamide in 80 ml 3 N hydrochloric acid solution and 5 ml 1-propanol was heated to 90–95° C. overnight. The reaction mixture was cooled to room temperature, washed with three 20 ml portions diethyl ether and filtered over celite. The filtrate was diluted with 20 ml water and was adjusted to pH 7–8 by addition of 28% sodium hydroxide solution under ice cooling. The product was extracted with four 100 ml portions of dichloromethane. The combined organic layers were washed with 50 ml brine, dried (magnesium sulfate) and evaporated to give 2.31 g (quantitative) of the title compound as a white foam.

MS m/e (%): 269 (M$^+$, 100).

f) Methyl-(6-morpholin-4-yl-4-o-tolyl-pyridin-3-yl)-amine

A solution of 2.24 g (8.3 mmol) 6-morpholin-4-yl-4-o-tolyl-pyridin-3-yl-amine in 17 ml trimethyl orthoformate and 3 drops trifluoroacetic acid was heated for 2 h at 130° C. The reaction mixture was evaporated and dried in vacuo for 30 min. The residual oil was dissolved in 5 ml tetrahydrofuran and was added dropwise under ice cooling to 630 mg (16.6 mmol) lithium aluminum hydride in 20 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 1.56 g (66%) of the title compound as a white foam.

MS m/e (%): 283 (M$^+$, 100).

g) 2-(35-Bis-trifluoromethyl-phenyl)-N-methyl-N-(6-morpholin-4-yl-4-o-tolyl-pyridin-3-yl)-isobutyramide A solution of 1.46 g (5.15 mmol) methyl-(6-morpholin-4-yl-4-o-tolyl-pyridin-3-yl)-amine and 1.32 ml (7.73 mmol) N-ethyldiisopropylamine in 15 ml dichloromethane was cooled in an ice bath and 1.8 g (5.67 mmol) 2-(3,5-bis-trifluoromethyl-phenyl)-2-methyl-propionyl chloride were added dropwise. The reaction mixture was warmed to 35–40° C. for 3 h, cooled to room temperature again and was stirred with 25 ml saturated sodium bicarbonate solution. The organic layer was separated and the aqueous phase was extracted with dichloromethane. The combined organic layers were dried (magnesium sulfate) and evaporated. The residue was purified by flash chromatography to give 2.9 g (quantitative) of the title compound as white crystals. M.p. 131–132° C.

h) 2-(3,5-Bis-trifluoromethyl-phenyl)-N-methyl-N-[6-(4-oxy-morpholin-4-yl)-4-o-tolyl-pyridin-3-yl]-isobutyramide To a solution of 5.0 g (8.84 mmol) 2-(3,5-bis-trifluoromethyl-phenyl)-N-methyl-N-(6-morpholin-4-yl-4-o-tolyl-pyridin-3-yl)-isobutyramide in 50 ml dichloromethane was added under ice cooling a soloution of 2.18 g (8.84 mmol) of 3-chloroperbenzoic acid (ca. 70%) in 35 ml dichloromethane. After stirring for 1 h at 0° C., 2.6 g (25.7 mmol) triethylamine were added slowly. The reaction mixture was concentrated to a total volume of 10 mL and the residue was purified by flash-chromatography. The crude material was suspended in 20 ml diethyl ether, filtered and dried in vacuo to give 4.2 g (82%) of the title compound as white crystals. M.p. 149–151° C. (partial decomposition).

MS m/e (%): 582 (M+H$^+$, 100).

i) 2-(3,5-Bis-trifluoromethyl-phenyl)-N-(6-hydroxy-4-o-tolyl-pyridin-3-yl)-N-methyl-isobutyramide A sample of 1.00 g (1.72 mmol) 2-(3,5-bis-trifluoromethyl-phenyl)-N-[6-(4-oxy-morpholin-4-yl)-4-o-tolyl-pyridin-3-yl]-isobutyramide was heated at 100° C. for 16 h and at 150° C. for 2 h. Column chromatography afforded 107 mg (13%) of the title compound as a white foam.

MS m/e (%): 496 (M$^+$, 30).

EXAMPLE 115

2-(3,5-Bis-trifluoromethyl-phenyl)-N-[4-(2-chloro-phenyl)-6-hydroxy-pyridin-3-yl]-N-methyl-isobutyramide a) 2-(3,5-Bis-trifluoromethyl-phenyl)-N-[4-(2-chloro-phenyl)-6-(4-oxy-morpholin-4-yl)-pyridin-3-yl]-N-methyl-isobutyramide The title compound was obtained in comparable yields according to the procedures described above for the preparation of 2-(3,5-bis-trifluoromethyl-phenyl)-N-methyl-N-[6-(4-oxy-morpholin-4-yl)-4-o-tolyl-pyridin-3-yl]-isobutyramide (Example 114, step h)) using 2-chlorophenylboronic acid instead of o-tolylboronic acid in step d). M.p.141–143° C. (partial decomposition).

MS m/e (%): 602 (M+H$^+$, 100), 624 (M+Na$^+$, 10).

b) 2-(3,5-Bis-trifluoromethyl-phenyl)-N-[4-(2-chloro-phenyl)-6-hydroxy-pyridin-3-yl]-N-methyl-isobutyramide A solution of 1.80 g (2.99 mmol) 2-(3,5-bis-trifluoromethyl-phenyl)-N-[4-(2-chloro-phenyl)-6-(4-oxy-morpholin-4-yl)-pyridin-3-yl]-N-methyl-isobutyramide in 20 ml toluene was heated at reflux for 60 h. After cooling to room temperature the solvent was evaporated. Column chromatography afforded 1.07 g of a light yellow foam. As determined by proton NMR spectroscopy this material consisted of a 4:1 mixture of the title compound and an isomer of the starting material (characterized by MS).

MS m/e (%): 517 (M+H$^+$, 100).

EXAMPLE 116

2-(3,5-Bis-trifluoromethyl-phenyl)-N-[4-(2-chloro-phenyl)-6-methoxy-pyridin-3-yl]-N-methyl-isobutyramide The title compound was obtained as a light yellow solid in 33% yield after column chromatography according to the procedure described above for the preparation of 6-benzyloxy-N-(3,5-bis-trifluoromethyl-benzyl)-N-methyl-4-o-tolyl-nicotinamide (Example 112) using 2-(3,5-bis-trifluoromethyl-phenyl)-N-[4-(2-chloro-phenyl)-6-hydroxy-pyridin-3-yl]-N-methyl-isobutyramide (Example 115; 80% purity) instead of N-(3,5-bis-trifluoromethyl-benzyl)-6-hydroxy-N-methyl-4-o-tolyl-nicotinamide and methyl iodide instead of benzyl bromide.

MS m/e (%): 531 (M+H$^+$, 100).

EXAMPLE 117

2-(3,5-Bis-trifluoromethyl-phenyl)-N-[4-(2-chloro-phenyl)-6-(pyridin-4-ylmethoxy)-pyridin-3-yl]-N-methyl-isobutyramide The title compound was obtained as a light orange solid in 15% yield after column chromatography according to the procedure described above for the preparation of 6-benzyloxy-N-(3,5-bis-trifluoromethyl-benzyl)-N-methyl-4-o-tolyl-nicotinamide (Example 112) using 2-(3,5-bis-trifluoromethyl-phenyl)-N-[4-(2-chloro-phenyl)-6-hydroxy-pyridin-3-yl]-N-methyl-isobutyramide (Example 115; 80% purity) instead of N-(3,5-bis-trifluoromethyl-benzyl)-6-hydroxy-N-methyl-4-o-tolyl-nicotinamide and 4-(bromomethyl)pyridine hydrobromide with one additional equivalent of silver carbonate instead of benzyl bromide.

MS m/e (%): 608 (M+H$^+$, 100).

EXAMPLE 118

2-(3,5-Bis-trifluoromethyl-phenyl)-N-[4-(2-chloro-phenyl)-6-(pyridin-3-ylmethoxy)-pyridin-3-yl]-N-methyl-isobutyramide The title compound was obtained as an off-white foam in 35% yield after column chromatography according to the procedure described above for the preparation of 6-benzyloxy-N-(3,5-bis-trifluoromethyl-benzyl)-N-methyl-4-o-tolyl-nicotinamide (Example 112) using 2-(3,5-bis-trifluoromethyl-phenyl)-N-[4-(2-chloro-phenyl)-6-hydroxy-pyridin-3-yl]-N-methyl-isobutyramide (Example 115; 80% purity) instead of N-(3,5-bis-trifluoromethyl-benzyl)-6-hydroxy-N-methyl-4-o-tolyl-nicotinamide and 3-(bromomethyl)pyridine hydrobromide with one additional equivalent of silver carbonate instead of benzyl bromide.

MS m/e (%): 608 (M+H$^+$, 100).

EXAMPLE 119

N-[6-Benzyloxy-4-(2-chloro-phenyl)-pyridin-3-yl]-2-(3,5-bis-trifluoromethyl-phenyl)-N-methyl-isobutyramide The title compound was obtained as a light yellow foam in 50% yield after column chromatography according to the procedure described above for the preparation of 6-benzyloxy-N-(3,5-bis-trifluoromethyl-benzyl)-N-methyl-4-o-tolyl-nicotinamide (Example 112) using 2-(3,5-bis-trifluoromethyl-phenyl)-N-[4-(2-chloro-phenyl)-6-hydroxy-pyridin-3-yl]-N-methyl-isobutyramide (Example 115; 80% purity) instead of N-(3,5-bis-trifluoromethyl-benzyl)-6-hydroxy-N-methyl-4-o-tolyl-nicotinamide.

MS m/e (%): 607 (M+H$^+$, 100).

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula

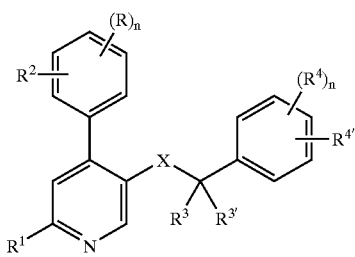

I wherein

R is hydrogen or halogen;

$R^1$ is —(C≡C)$_m$R$^{1'}$ or —(CR'=CR")$_m$R$^{1'}$
   wherein R$^{1'}$ is is a six membered non-aromatic heterocycle of the formula

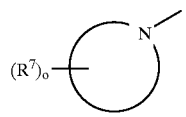

which optionally has one additional heteroatom, selected from N, O or S, $R^7$ is —C(O)—(CH$_2$)$_m$OH or an oxo group;

$R^2$ is hydrogen, lower alkyl, lower alkoxy, halogen or CF$_3$;

$R^3/R^{3'}$ are independently hydrogen, lower alkyl $R^4/R^{4'}$ are hydrogen, halogen, CF$_3$, lower alkyl or lower alkoxy;

X is —C(O)N(R$^8$)—, or —N(R$^8$)C(O)
   wherein R$^8$ is hydrogen or lower alkyl;

n is 1 or 2;

m is 0, and o is 1 or 2;

or a pharmaceutically acceptable acid addition salt thereof.

2. A compound of the formula

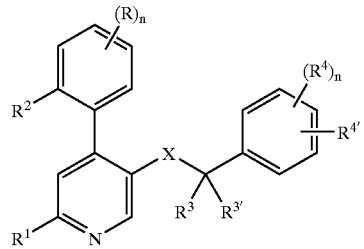

I wherein

R is hydrogen or halogen;

$R^1$ is —(C≡C)$_m$R$^{1'}$ or —(CR'=CR")$_m$R$^{1'}$
   wherein R$^{1'}$ is n) is a six membered non-aromatic heterocycle of the formula

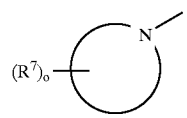

or a six membered non-aromatic heterocycle having one additional heteroatom, selected from N, O or S, $R^7$ is —C(O)—(CH$_2$)$_m$ OH or an oxo group;

$R^2$ is lower alkyl, halogen or CF$_3$;

$R^3/R^{3'}$ are hydrogen, $R^4/R^{4'}$ are hydrogen, halogen, CF$_3$, lower alkyl or lower alkoxy;

X is —C(O)N(R$^8$)—, or —N(R$^8$)C(O)—
   wherein R$^8$ is hydrogen or lower alkyl;

n is 1 or 2;

m is 0 and o is 1 or 2;

or a pharmaceutically acceptable acid addition salt thereof.

3. A compound of formula IA according to claim 1,

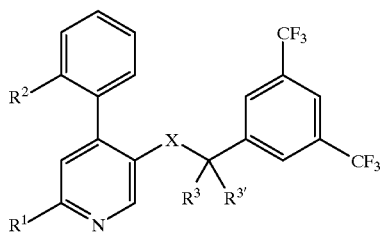

IA wherein $R^1$ is morpholinyl or piperazinyl, substituted by —C(O)—(CH$_2$)$_m$ OH or oxy group(s), R is hydrogen or halogen;

$R^2$ is lower alkyl or halogen;

$R^3/R^{3'}$ are hydrogen or lower alkyl;

X is —C(O)N(R$^8$)—or —N(R$^8$)C(O)—;

$R^8$ is hydrogen or lower alkyl; and m is 0.

4. A compound according to claim 1 having the formula

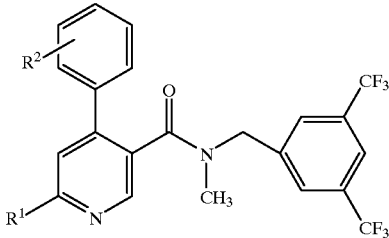

1-100 wherein $R^1$ and $R^2$ are as defined above.

5. A compound according to claim 4, wherein $R^2$ is lower alkyl.

6. A compound according to claim 5 wherein $R^2$ is 2-methyl.

7. A compound according to claim 1 wherein the compound is N-(3,5-Bis-trifluoromethyl-benzyl)-6-(4-hydroxyacetyl-piperazin-1-yl)-N-methyl-4-o-tolyl-nicotinamide.

8. A compound according to claim 1 wherein the compound is 4-o-Tolyl-1',2',3',6'-tetrahydro-[2,4']bipyridinyl-5-carboxylic acid (3,5-bis-trifluoromethyl-benzyl)-methyl-amide.

9. A compound according to claim 1 having the structure

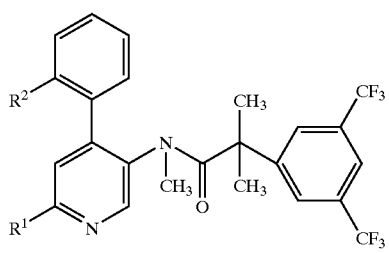

1-101 wherein $R^1$ and $R^2$ are as above.

10. A compound according to claim 9 wherein $R^2$ is halogen.

11. A compound according to claim 10 wherein said halogen is 2-Chloro.

12. A compound according to claim 11 wherein the compound is 2-(3,5-Bis-trifluoromethyl-phenyl)-N-[4-(2-chloro-phenyl)-6-(3-oxo-morpholin-4-yl)-pyridin-3-yl]-N-methyl-isobutyramide.

13. A compound according to claim 9 wherein $R^2$ is lower alkyl.

14. A compound according to claim 13 wherein $R^2$ is methyl.

15. A compound according to claim 1 wherein the compound is 2-(3,5-Bis-trifluoromethyl-phenyl)-N-methyl-N-[6-(3-oxo-morpholin-4-yl)-4-o-tolyl-pyridin-3-yl]-isobutyramide.

16. A pharmaceutical composition comprising a compound of claim 1 and at least one pharmaceutically acceptable carrier.

17. A compound according to claim 1 wherein the compound is 5-[(3,5-Bis-trifluoromethyl-benzyl)-methyl-carbamoyl]-4-o-tolyl-3',6'-dihydro-2'H-[2,4']bipyridinyl-1'-carboxylic acid tert-butyl ester.

18. A compound according to claim 1 wherein the compound is 1'-Cyclopropylmethyl-4-o-tolyl-1',2',3',6'-tetrahydro-[2,4']bipyridinyl-5-carboxylic acid (3,5-bis-trifluoromethyl-benzyl)-methyl-amide.

19. A compound according to claim 1 wherein the compound is 5-{[2-(3,5-Bis-trifluoromethyl-phenyl)-2-methyl-propionyl]-methyl-amino}-4-o-tolyl-3',6'-dihydro-2'H-[2,4']bipyridinyl-1'-carboxylic acid tert-butyl ester.

* * * * *

UNITED STATES PATENT AND TRADEMARK OFFICE
CERTIFICATE OF CORRECTION

PATENT NO. : 6,770,637 B2
DATED : August 3, 2004
INVENTOR(S) : Thierry Godel, Torsten Hoffmann, Patrick Schnider and Heinz Stadler It is certified that error appears in the above-identified patent and that said Letters Patent is hereby corrected as shown below:

Title page,
Item [*] Notice, the asterisk should be corrected to include Terminal disclaimer filed Signed and Sealed this First Day of March, 2005

JON W. DUDAS
*Director of the United States Patent and Trademark Office*